(12) United States Patent
Markovic et al.

(10) Patent No.: US 10,507,243 B2
(45) Date of Patent: *Dec. 17, 2019

(54) NANOPARTICLE COMPLEXES OF RITUXIMAB, ALBUMIN AND PACLTAXEL

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/414,526

(22) Filed: Jan. 24, 2017

(65) Prior Publication Data

US 2017/0128587 A1 May 11, 2017

Related U.S. Application Data

(63) Continuation of application No. 15/202,115, filed on Jul. 5, 2016, now Pat. No. 9,757,453, which is a continuation of application No. 14/432,979, filed as application No. PCT/US2013/062638 on Sep. 30, 2013, now Pat. No. 10,413,606.

(60) Provisional application No. 61/708,575, filed on Oct. 1, 2012, provisional application No. 61/725,293, filed on Nov. 12, 2012.

(51) Int. Cl.
| | |
|---|---|
| *A61K 39/395* | (2006.01) |
| *A61K 39/44* | (2006.01) |
| *C07K 16/32* | (2006.01) |
| *A61K 33/24* | (2019.01) |
| *A61K 31/555* | (2006.01) |
| *A61K 9/51* | (2006.01) |
| *A61K 47/64* | (2017.01) |
| *A61K 47/68* | (2017.01) |
| *A61K 47/69* | (2017.01) |
| *A61K 9/00* | (2006.01) |
| *A61K 41/00* | (2006.01) |
| *A61K 45/06* | (2006.01) |
| *C07K 16/22* | (2006.01) |
| *C07K 16/28* | (2006.01) |
| *A61K 31/337* | (2006.01) |
| *C07K 16/30* | (2006.01) |
| *A61K 31/282* | (2006.01) |
| *A61K 9/14* | (2006.01) |
| *A61K 39/00* | (2006.01) |
| *B82Y 5/00* | (2011.01) |

(52) U.S. Cl.
CPC ...... *A61K 39/39558* (2013.01); *A61K 9/0019* (2013.01); *A61K 9/14* (2013.01); *A61K 9/51* (2013.01); *A61K 9/5169* (2013.01); *A61K 31/282* (2013.01); *A61K 31/337* (2013.01); *A61K 31/555* (2013.01); *A61K 33/24* (2013.01); *A61K 39/395* (2013.01); *A61K 41/0052* (2013.01); *A61K 45/06* (2013.01); *A61K 47/643* (2017.08); *A61K 47/6801* (2017.08); *A61K 47/6803* (2017.08); *A61K 47/6845* (2017.08); *A61K 47/6849* (2017.08); *A61K 47/6851* (2017.08); *A61K 47/6855* (2017.08); *A61K 47/6863* (2017.08); *A61K 47/6865* (2017.08); *A61K 47/6867* (2017.08); *A61K 47/6929* (2017.08); *A61K 47/6931* (2017.08); *C07K 16/22* (2013.01); *C07K 16/2863* (2013.01); *C07K 16/2887* (2013.01); *C07K 16/2893* (2013.01); *C07K 16/3015* (2013.01); *C07K 16/32* (2013.01); *A61K 2039/505* (2013.01); *A61K 2039/545* (2013.01); *A61K 2039/6056* (2013.01); *B82Y 5/00* (2013.01); *C07K 2317/21* (2013.01); *C07K 2317/24* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |

(Continued)

FOREIGN PATENT DOCUMENTS

| | | |
|---|---|---|
| EP | 1 913 947 A1 | 4/2008 |
| JP | S60146833 | 8/1985 |

(Continued)

OTHER PUBLICATIONS

"A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: <URL: https://clinicaltrials.gov/archive/NCT00434252/200703 12>, dated Mar. 12, 2007, 3 pages.

(Continued)

*Primary Examiner* — Christine J Saoud
(74) *Attorney, Agent, or Firm* — Myers Bigel, P.A.

(57) ABSTRACT

Described are stable nanoparticle complexes comprising paclitaxel, albumin and rituximab. The nanoparticle complexes are suitable for the treatment of cancer.

15 Claims, 56 Drawing Sheets

(56) References Cited

U.S. PATENT DOCUMENTS

| | | |
|---|---|---|
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,466,148 B2 | 10/2016 | Gay et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Neil et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |

FOREIGN PATENT DOCUMENTS

| | | |
|---|---|---|
| JP | S6178731 | 4/1986 |
| JP | H04504253 | 7/1992 |
| JP | 2001-072589 | 3/2001 |
| KR | 1020090078330 | 7/2009 |
| RU | 2011133819 | 2/2013 |
| WO | WO-89/10398 A1 | 11/1989 |
| WO | 97/49390 | 12/1997 |
| WO | WO-99/00113 A1 | 1/1999 |
| WO | WO-99/51248 A1 | 10/1999 |
| WO | 2004/022097 | 3/2004 |
| WO | WO-2004/096224 A2 | 11/2004 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | WO-2008/057562 A1 | 5/2008 |
| WO | WO-2008/112987 A1 | 9/2008 |
| WO | WO-2009/043159 A1 | 4/2009 |
| WO | WO-2009/055343 A2 | 4/2009 |
| WO | WO-2010/003057 A2 | 1/2010 |
| WO | WO-2010/017216 A2 | 2/2010 |
| WO | 2010/118365 | 10/2010 |
| WO | 2010/124009 | 10/2010 |
| WO | WO-2012/048223 A1 | 4/2012 |
| WO | WO 2012/088388 A2 | 6/2012 |
| WO | WO-2012/154861 A2 | 11/2012 |
| WO | WO-2014/009774 | 1/2014 |
| WO | 2014/037422 | 3/2014 |
| WO | WO-2014/055415 A1 | 4/2014 |
| WO | WO-2014/123612 | 8/2014 |
| WO | 2015/048520 | 4/2015 |
| WO | WO-2015/191969 A1 | 12/2015 |
| WO | WO-2015/195476 A1 | 12/2015 |
| WO | 2016/059220 | 4/2016 |
| WO | WO-2016/057554 A1 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |

(56) References Cited

FOREIGN PATENT DOCUMENTS

| WO | 2018/045238 | 3/2018 |
|---|---|---|
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

"Concurrent Infusions", J Oncol Pract., 4(4): 171, Jul. 2008.
AACR Presentation, "Targeted nano-immune conjugates to melanoma: Pre-clinical testing of bevacizumab targeted nab-paclitaxel," Mayo Clinic, 2014.
Abraxane® for Injectable Suspension (paclitaxel protein-bound particles for injectable suspension) (albumin-bound), [drug label], 22 pages, Sep. 2009.
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(185):8510 (Abstract).
Allen, TM, "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health, 2007, 4 pages.
Arakawa et al., "Protein-Solvent Interactions in Pharmaceutical Formulations", Pharm. Res., Mar. 1991, vol. 8, Issue 3, pp. 285-291.
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:S11-14.
Atkins, Michael, "Interleukin-2: clinical applications", Semin Oncol., 2002, 29(3 Suppl 7):12-27.
Avastin® Bevacizumab, Roche, [drug label], 24 pages, Sep. 2008.
Bairagi et al., Albumin: A Versatile Drug Carrier, Austin Therapeutics, (Nov. 17, 2015) vol. 2, No. 2, p. 1021 (pp. 1-6), especially abstract, p. 2, Table 2, p. 2 col. 2 para. 2.
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer, K., et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Boasberg et al., Nab-paclitaxel and bevacizumab as first-line therapy in patients with unresectable stage III and IV melanoma, J Clin Oncol., 27:15s, 2009 (suppl; abstr 9061), 2009 ASCO Annual Meeting, Retrieved from the Internet: <URL: http://meetinglibrary.asco.org/print/584876>, 2 pages, 2009.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Celts, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Davis, "Affinity separation of antibody-toxin conjugate from albumin-stabilized formulation", Am Biotechnol Lab., 12(4):60-64, Mar. 1994.
Degrasse, J.A., "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et. al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., 1 Apr. 2008, 31(2):173-181.
Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6):1973-1980.
Ellyard et al., "Th2-mediated anti-tumour immunity: friend or foe?", Tissue Antigens, 2007, 70(1):1-11.
Elsadek et al., "Impact of albumin on drug delivery—New applications on the horizon", J of Controlled Release, 2011, 1-25.
Ferrara et al., "The biology of VEGF and its receptors", Nat. Med., 2003, 9:669-676.

(56) References Cited

OTHER PUBLICATIONS

Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Folkman, J., "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Graells et al., "Overproduction of VEGF16s concomitantly expressed with its receptors promotes growth and survival of melanoma cells through MAPK and P13K signaling", J. Invest. Dermatol., 2004, 123:1151-1161.
Gupta, I., et al., "Ofatumumab, the first human anti-CD20 monoclonal antibody for the treatment of B cell hematologic malignancies," Ann. N.Y. Acad. Sci., 1263, pp. 43-56 (Jul. 25, 2012).
Haley et al., "Nanoparticles for drug delivery in cancer treatment", Urol. Oncol.: Seminars and Original Invest., 2008, 26:57-64.
Harlow & Lane, Antibodies: A Laboratory Manual, Cold Spring Harbor Laboratory, New York, 1988.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phase II trial of ABI-007 in previously treated and previously untreated patients with metastatic malignant melanoma", J. Clin. Oncol., 2005, 23(165):7558 (Abstract).
Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Hood et al., Immunology, 1984, Benjamin, N.Y., 2nd edition.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an anti-digoxin single-chain Fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2012/037137 dated Nov. 12, 2013, 5 pages.
International Preliminary Report on Patentability for Application No. PCT/US2008/057025, dated Sep. 15, 2009, 6 pages.
International Preliminary Report on Patentability for Application No. PCT/US2009/049511, dated Jan. 5, 2011, 6 pages.
International Preliminary Report on Patentability for Application No. PCT/US2013/062638, dated Apr. 16, 2015, 11 pages.
International Preliminary Report on Patentability, PCT/US2015/035505, Mayo Foundation for Medical Education and Research, 10 pages (dated Dec. 22, 2016).
International Preliminary Report on Patentability, PCT/US2015/035515, Mayo Foundation for Medical Education and Research, 18 pages (dated Dec. 29, 2016).
International Search Report and Written Opinion for Application No. PCT/US15/35505 dated Nov. 24, 2015. 17 pages.
International Search Report and Written Opinion for Application No. PCT/US15/35515 dated Sep. 21, 2015. 23 pages.
International Search Report and Written Opinion for Application No. PCT/US16/47641 dated Oct. 31, 2016, 11 pages.
International Search Report and Written Opinion for Application No. PCT/US17/17553 dated Feb. 10, 2017, 13 pages.
International Search Report and Written Opinion for Application No. PCT/US2008/057025, dated Jul. 1, 2008, 11 pages.
International Search Report and Written Opinion for Application No. PCT/US2009/049511, dated Feb. 2, 2010, 8 pages.
International Search Report and Written Opinion for Application No. PCT/US2012/037137 dated Sep. 28, 2012, 5 pages.
International Search Report and Written Opinion for Application No. PCT/US2013/062638 dated Jan. 23, 2014, 19 pages.
International Search Report and Written Opinion for Application No. PCT/US2015/054295 dated Jan. 25, 2016, 15 pages.
Jain et al., "Delivering nanomedicine to solid tumors", Nature Reviews Clinical Oncology, Nov. 2010, 7, pages. 653-664.
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther., (2003), 2:1183-1193.
Jiang et al., "Regulation of Immune Responses by T Cells", N Engl J Med., 2006, 354(11): 1166-1176.
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patients", Lung Cancer, 2008, 59(1):41-47.
Kikuchi et al., "Vascular endothelial growth factor and dendritic cells in human squamous cell carcinoma of the oral cavity", Anticancer Res., 2006, 26(3A):1833-1848.
Kim et al., "A Dual Target-directed Agent against Interleukin-6 Receptor and Tumor Necrosis Factor a ameliorates experimental arthritis", Scientific Reports, 2016, pp. 1-12.
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncology: official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.

(56) References Cited

OTHER PUBLICATIONS

Korman et al., "Tumor immunotherapy: preclinical and clinical activity of anti-CTLA4 antibodies", Curt Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Temozolomide and Bevacizumab or nab-Paclitaxel, Carboplatin, and Bevacizumab in Patients with Unresectable Stage IV Melanoma", Cancer, 2013, vol. 119, Issue 3, pp. 586-592.
Kratz et al., "Serum proteins as drug carriers of anticancer agents: a review", Drug Deliv., 5(4):281-299, 1998.
Kratz, "Albumin as a drug carrier: design of prodrugs, drug conjugates and nanoparticles", J Control Release, 132(3):171-183, Epub May 17, 2008.
Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.
Kukowska-Latallo et al., Nanoparticle Targeting of Anticancer Drug Improves Therapeutic Response in Animal Model of Human Epithelial Cancer, Cancer Res, 2005, 65(12):5317-5324.
Kumar et al., Th1/Th2 cytokine imbalance in meningioma, anaplastic astrocytoma and glioblastoma multiforme patients, Oncol. Rep., 2006, 15(6):1513-1516.
Lanzavecchia et al., "The use of hybrid hybridomas to target human cytotoxic T lymphocytes", Eur. J. Immunol., 1987, 17, pp. 105-111.
Lau et al., Is inhibition of cancer angiogenesis and growth by paclitaxel schedule dependent?, Anti-Cancer Drugs, 2004, 15:871-875.
Lei et al., Comparing cellular uptake and cytotoxicity of targeted drug carriers in cancer cell lines with different drug resistance mechanisms, Nanomed: Nanotech, Biol, and Med., 2011, 7:324-332.
Lev et al., Dacarbazine causes transcriptional up-regulation of interleukin 8 and vascular endothelial growth factor in melanoma cells: a possible escape mechanism from chemotherapy, Mol. Cancer Ther., 2003, 2:753-763.
Lev et al., Exposure of melanoma cells to dacarbazine results in enhanced tumor growth and metastasis in vivo, J. Clin. Oncol., 2004, 22:2092-2100.
Lin, S.Y, "Salmon calcitonin: conformational changes and stabilizer effects", AIMS Biophysics, 2015, 2(4): 695-723.
Lundin et al., Phase 2 Study of Alemtuzumab (anti-CD52 Monoclonal Antibody) in Patients with Advanced Mycosis Fungoides/Sezary Syndrome, Blood. (Jun. 1, 2003) vol. 101, No. 11, pp. 426-772, especially p. 4267 col. 1, para. 1, p. 4267 col. 2, para 2-p. 4268 col. 1, para. 1, p. 4271 col. 1, para. 3.
Marcoval et al., Angiogenesis and malignant melanoma. Angiogenesis is related to the development of vertical (tumorigenic) growth phase, J. Cutan. Pathol., 1997, 24:212-218.
Markovic et al., A phase II study of ABT-510 (thrombospondin-1 analog) for the treatment of metastatic melanoma, Am. J. Clin. Oncol., 2007, 30(3):303-309.
Markovic et al., A reproducible method for the enumeration of functional ( cytokine producing) versus non-functional peptide-specific cytotoxic T lymphocytes in human peripheral blood, Clin. Exo. Immunol., 2006, 145:438-447.
Markovic et al., Peptide vaccination of patients with metastatic melanoma: improved clinical outcome in patients demonstrating effective immunization, Am J Clin Oncol., 2006, 29(4):352-360.
Matejtschuk, P., "Lyophilization of Proteins", Methods in Molecular Biology, Cryopreservation and Freeze-Drying Protocols, Second Edition, Edited by: J. G. Day and G. N. Stacey @ Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.

Mayo Clinic: Paclitaxel Albumin-Stabilized Nanoparticle Formulation and Bevacizumab in Treating Patients With Stage IV Melanoma That Cannot Be Removed by Surgery—Full Text View ClinicalTrials.gov, Dec. 19, 2013, pp. 1-4, Retrieved from the Internet URL:https//clinicaltrials.gov/ct2/show/NCT02020707?term=targeted+nanoparticle+therapy+for+advanced+melanoma&rank=1 [retrieved on Jan. 6, 2016].
McElroy et al., Imaging of Primary and Metastatic Pancreatic Cancer Using a Fluorophore-Conjugated Anti-CA19-9 Antibody for Surgical Navigation, World J Surg., 2008, 32: 1057-1066.
Melcher, Recommendations for influenza and pneumococcal vaccinations in people receiving chemotherapy, Clin Oncol (R Coll Radiol), 2005, 17(1): 12-15.
Merchan et al., Increased endothelial uptake of paclitaxel as a potential mechanism for its antiangiogenic effects: potentiation by Cox-2 inhibition, Int. J. Cancer, 2005, 113, pp. 490-498.
Mezzaroba et al., "New potential therapeutic approach for the treatment of B-Cell malignancies using chlorambucil/Hydroxychloroquine-Loaded Anti-CD20 Nanoparticles", Sep. 2103, PLoS One vol. No. 8, Issue 9 pp. 1-10, e74216.
Middleton et al., Randomized phase III study of temozolomide versus dacarbazine in the treatment of patients with advanced metastatic malignant melanoma, J. Clin. Oncol., 2000, 18, pp. 158-166.
Miller et al. "Paclitaxel plus Bevacizumab versus Paclitaxel Alone for Metastatic Breast Cancer," N Engl. J Med., (2007) vol. 357:2666-2676.
Mimura et al., Vascular endothelial growth factor inhibits the function of human mature dendritic cells mediated by VEGF receptor-2, Cancer Immunol Immunother., 2007, 56(6). pp. 761-770.
Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.
Mocellin et al., Cytokines and immune response in the tumor microenvironment, J Immunother., 2001, 24(5), pp. 392-407.
Motl, S., Bevacizumab in combination chemotherapy for colorectal and other cancers, Am. J. Health-Syst. Pharm 2005, 62:1021-1032.
Ng et al., Influence of formulation vehicle on metronomic taxane chemotherapy: albumin-bound versus cremophor El-based paclitaxel, Clin. Cancer Res., 2006, 12, pp. 4331-4338.
Ng et al., Taxane-mediated antiangiogenesis in vitro: influence of formulation vehicles and binding proteins, Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.
Oku et al., Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts, Cancer Res., 1998, 58, pp. 4185-4192.
Parikh et al., The vascular endothelial growth factor family and its receptors, Hematol. Oncol. Clin. N. Am., 2004, 18, pp. 951-971.
Park et al., Anti-HER2 Immunoliposomes: Enhanced Efficacy Attributable to Targeted Delivery, Clin. Cancer Res., 2002, 8, pp. 1172-1181.
Perez et al., "Phase 2 trial of carboplatin, weekly paclitaxel, and biweekly bevacizumab in patients with unresectable stage IV melanoma," A north central cancer treatment group study, Cancer, 2009, 115(1), pp. 119-127.
Phase II: A Study of Bevacizumab With Carboplatin and Paclitaxel Chemotherapy for the First-Line Treatment of Patients With Metastatic Melanoma (BEAM) Mar 12, 2007, [retrieved Mar. 15, 2010]. Retrieved from the Internet: <URL:http://clinicaltrials.gov/archive/NCT00434252/2007 03 12>, 3 pages.
Pikal, M., Freeze-drying of proteins, Part II: Formulation selection, Biopharm, 1990, 9, pp. 26-30.
Polak et al., Mechanisms of local immunosuppression in cutaneous melanoma, Br J Cancer, 2007, 96(12), pp. 1879-1887.

(56) References Cited

OTHER PUBLICATIONS

Porrata et al., Early lymphocyte recovery predicts superior survival after autologous hematopoietic stem cell transplantation in multiple myeloma or non-Hodgkin lymphoma, Blood, 2001, 98(3), pp. 579-585.
Porrata et al., Timely reconstitution of immune competence affects clinical outcome following autologous stem cell transplantation, Clin Exp Med., 2004, 4(2):78-85.
Powell et al., Adoptive transfer of vaccine-induced peripheral blood mononuclear cells to patients with metastatic melanoma following lymphodepletion, J Immunol., 2006, 177(9), pp. 6527-6539.
Pries et al., Cytokines in head and neck cancer, Cytokine Growth Factor Rev., 2006, 17(3), pp. 141-146.
Ranieri et al., "Vascular endothelial growth factor (VEGF) as a target of bevacizumab in cancer: from the biology to the clinic", Curr. Med. Chem., 2006, 13, 1845-1857.
Rao et al., "Combination of paclitaxel and carboplatin as second-line therapy for patients with metastatic melanoma", Cancer, 2006, 106(2), 375-382.
Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+ T cells in patients with melanoma", J. Immunol., 2005, 175(9), pp. 6169-6176.
Roy et al., "Tumor associated release of interleukin-10 alters the prolactin receptor and down-regulates prolactin responsiveness of immature cortical thymocytes", J Neuroimmunol., 2007, 186(1-2), pp. 112-120.
Rudnicka et al., "Rituximab causes a polarization of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al., "Antibody targeted drugs as cancer therapeutics, Nature Reviews Drug Discovery", Feb. 2006, 5, pp. 147-159.
Sester et al., "Differences in CMV-specific T-cell levels and long-term susceptibility to CMV infection after kidney, heart and lung transplantation", Am J Transplant., 5(6):1483-1489, Jun. 2005.
Srivastava et al., "Angiogenesis in cutaneous melanoma: pathogenesis and clinical implications", Microsc. Res. Tech., 2003, 60:208-224.
Streit et al., "Angiogenesis, lymphangiogenesis, and melanoma metastasis", Oncogene, 2003, 22, pp. 3172-3179.
Taieb et al., "Chemoimmunotherapy of tumors: Cyclophosphamide synergizes with exosome based vaccines", J. Immunol., Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.

Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.
Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications", Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers: Active Targeting Ligands for Cancer Diagnosis and Therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.
Yuan et al., "Vascular Permeability in a Human Tumor Xenograft: Molecular Size Dependence and Cutoff Size", Cancer Research, Sep. 1, 1995, 55, pp. 3752-3756.
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.
Abraxis Bicscience, Inc., "Abraxane: For the adjuvant treatment of node-positive breast cancer administered sequentially to standard doxorubicin-containing combination chemotherapy," Oncologic Drugs Advisory Committee Meeting (availabie to public Aug. 4, 2006).
Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposium, URL: http://sabcs.org/portals/sabcs2016/documents/sabcs-2016-abstracts.pdf?v=5.
Adams et al., "Phase Ib trial of atezolizumab in combination with nab-paclitaxel in patients with metastatic triple-negative breast cancer (mTNBC)" Journal of Clinical Oncology col. 34, No. 15, May 1, 2016, 4 pages.
Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Anonymous, "Atezolizumab Plus Abraxane Promising New Treatment for TripleNeg tive Breast Cancer" UNM Comprehensive Cancer Center, Jan. 7, 2016, pp. 1-2.
U.S. Appl. No. 14/116,619, office action dated Feb. 4, 2015.

(56) References Cited

OTHER PUBLICATIONS

U.S. Appl. No. 14/116,619, office action dated Apr. 28, 2016.
U.S. Appl. No. 14/116,619, office action dated Sep. 10, 2015.
U.S. Appl. No. 14/432,979, office action dated Jan. 7, 2019.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Feb. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Jan. 22, 2019.
U.S. Appl. No. 15/052,336, office action dated Feb. 9, 2016.
U.S. Appl. No. 15/052,336, office action dated Sep. 4, 2018.
U.S. Appl. No. 15/052,623, office action dated Jan. 7, 2019.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623 office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433 office action dated Mar. 21, 2018.
U.S. Appl. No. 15/092,433, office action dated Aug. 10, 2018.
U.S. Appl. No. 15/092,433, office action datd Oct. 11, 2017.
U.S. Appl. No. 15/092,433; office action dated Dec. 12, 2018.
U.S. Appl. No. 15/187,672, office action dated May 31, 2018.
U.S. Appl. No. 15/187,672, office action dated Nov. 28, 2018.
U.S. Appl. No. 15/202,115, office action dated Jan. 20, 2017.
U.S. Appl. No. 15/202,115, office action dated Sep. 26, 2016.
U.S. Appl. No. 16/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/226,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/266,024, office action dated Jan. 6, 2017.
U.S. Appl. No. 15/286,024, office action dated May 19, 2017.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,536; office action dated Oct. 1, 2018.
U.S. Appl. No. 15/412,554, office action dated Sep. 27, 2018.
U.S. Appl. No. 15/412,564, office action dated Jul. 10, 2018.
U.S. Appl. No. 15/412,581; office action dated Nov. 13, 2018.
U.S. Appl. No. 15/412,596, office action dated Sep. 4, 2018.
U.S. Appl. No. 15/412,596, office action dated Dec. 27, 2018.
U.S. Appl. No. 15/412,610, office action dated Jul. 9, 2018.
U.S. Appl. No. 15/413,257; office action dated Sep. 25, 2018.
U.S. Appl. No. 15/414,633; office action dated Nov. 19, 2018.
U.S. Appl. No. 15/414,530; office action dated Oct. 11, 2018.
U.S. Appl. No. 15/452,669, office action dated May 5, 2017.
U.S. Appl. No. 15/452,569, office action dated Nov. 16, 2017.
U.S. Appl. No. 15/452,669, office action dated Nov. 26, 2018.
Armitage et al., "New approach to classifying non-Hodgkin's lymphomas: clinical features of the major histologic subtypes. Non-Hodgkin's Lymphoma Classification Project" J Clin Oncol 16, 2780-2795 (1998).
Baba, Oleo Science 10(1):15-18 (Jan. 2010).
Colman, "Effects of amino acid sequence changes on antibody-antigen interactions," Research in Immunology (145(1):33-36, (1994).

Desai et al., "Enhanced antitumor activity and safety of albumin-bound nab-docetaxel versus polysorbate 80-based docetaxel", Eur. J. Cancer. Suppl.; 18th Symposium on molecular targets and cancer therapeutics; Prague, Czech Republic; Nov. 7-10, 2006. vol. 4, No. 12, Nov. 2006 *Nov. 2006), p. 49.
Edison, "MorphoSys," 16 pages (Aug. 8, 2013).
Elst et al. "Epidermal Growth Factor Receptor Expression and Activity in Acute Myeloid Leukemia", Blood 116:3144 (2010), abstract.
Emens et al.: "(OT1-01-06) A phase III randomized trial of atezolizumab in combination with nab-paclitaxel as firs tline therapy for patienst with metastatic triple-negative breast cancer (mTNBC)", 2015, XP002775313, 2015 San Antonio Breast Cancer Symposium, URL: http://sabcs.org/portals/sabcs2016/documents/sabcs-2015-abstracts.pdf?v=5.
European Application No. 08743903.0, Extended European Search Report dated Jan. 24, 2011.
European Application No. 09774506.1, Extended European Search Report dated Mar. 22, 2012.
European Application No. 12781802.9, Extended European Search Report dated Dec. 18, 2014.
European Application No. 13843209.1, Extended European Search Report dated Sep. 5, 2016.
European Application No. 15806443.6, Extended European Search Report dated Dec. 11, 2017.
European Application No. 16809075.3, extended European Search Report dated Dec. 21, 2017.
Fabi et al, "Prospective study on nanoparticle albumin-bound paclitaael in advanced breast cancer: clinical results and biological observations in taxane-pretreated patients", Drug Design, Development and Therapy vol. 9, Nov. 1, 2015, 7 pages.
Flores et al., "Novel oral taxane therapies: recent Phase I results", Clin. Invest. vol. 3, No. 4, Apr. 1, 2013 (Mar. 1, 2013), pp. 333-341, XP055426571 , UK, ISSN: 2041-6792, DOI: 10.4155/cli.13.18.
Golay et al., "Mechanism of action of therapeutic monoclonal antibodies: promises and pitfalls of in vitro and in vivo assay," Arch. Blochem. Biophys. 526(2):146-163 (2012).
Hamilton et al, "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.
Hara, "What is anti-HER2 antibody tubulin polymerization inhibitor complex T-DM1?," Pharm. Monthly 56(5):734-739 (May 2014).
Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.
Hegde et al. "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Inman, "Afezolizumab/Nab-Paclitaxel Combo Shows High Response Rates in TNBC", OneLive, Dec. 10, 2015, 4 pages.
International Preliminary Report on Patentability for Application No. PCT/US2015/054295 dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Application No. PCT/US2017/023443, dated Oct. 4, 2018.
International Preliminary Report on Patentability for Application PCT/US2016/026267, dated Apr. 10, 2016.
International Preliminary Report on Patentability for Application PCT/US2017/017553, dated Aug. 23, 2018.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.

(56) References Cited

OTHER PUBLICATIONS

International Search Report and Written Opinion for Application No. PCT/US2017/012580, dated Mar. 17, 2017.
International Search Report and Written Opinion for Application No. PCT/US2017/023442, dated Jun. 16, 2017.
International Search Report and Written Opinion for Application No. PCT/US2017/023443, dated Jul. 11, 2017.
International Search Report and Written Opinion for Application No. PCT/US2017/045643, dated Oct. 25, 2017.
International Search Report and Written Opinion for Application No. PCT/US2017/049745, dated Dec. 15, 2017.
International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
International Search Report and Written Opinion for Application No. PCT/US2017/050355 dated Jan. 30, 2018.
Jaime et al., "Paclitaxel antibody conjugates and trehalose for preserving the immunological activity after freeze-drying," Curr Med Chem, 2004, 11(4):439-46 Abstract Only.
Jain et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jin et al., "Paclitaxel-loaded nanoparticles decorated with anti-CD133 antibody: a targeted therapy for liver cancer stem cells," J. Nanopart. Res. 2014, 16:2157 (2014).
Jin et al: "Docetaxel-loaded PEG-albumin nanoparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.
Kelly et al. "Shape-Specific, Monodisperse Nano-Molding of Protein Particles." J. Am, Chem. Soc. 130:5438-5439 (2008).
Lee et al., "The co-delivery of paclitaxel and Herceptin using cationic micellar nanoparticles", Biomaterials vol. 30, No. 5, Feb. 1, 2009, pp. 919-927.
Liang et al., "IFN-alpha regulates NK cell cytotoxicity through STAT1 pathway," Cytokine, Aug. 13, 2003 (Aug. 13, 2013), vol. 23, pp. 190-199.
Lloyd et al. "Modelling the human immune response: performance of a 1011 human antibody repertoire against a broad panel of therapeutically relevant antigens", Protein Eng. , Design & Selection 22(3):159-168 (2009).
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Meadows et al. "Anti-VEGF Therapies in the Clinic," Cold Spring Harbor Perspectives in Medicine, Oct. 1, 2012 (Oct. 1, 2012), vol. 2, pp. 1-27.
Mustacchi et al, "The role of taxanes in triple-negative breast cancer: literature review", Drug Design, Development and Therapy, vol. 9, Aug. 5, 2015, 16 pages.
Nahleh et al, "Swog S0800 (NCI CDR0000636131): addition of bevacizumba to neoadjuvant nab-paclitaxel with dose-dense doxorublcin and cyclophosphamide improves pathologic complete response (pCR) rates in inflammatory or locally advanced breast cancer", Breast Cancer Research and Treatment, vol. 158, No. 3 Jul. 8, 2016, 12 pages.
Nevala et al, "Abstract B77: Targeted nano-immune conjugates to melanoma: Preclinical testing of bevacizumab targeted nab-paclitaxel", Cancer Immunology Research, vol. 3, Oct. 1, 2015, 3 pages.
Nevala et al, "Antibody-targeted paclitaxel loaded nanoparticles for the treatment of CD20 B-cell lymphoma", Scientific Reports, vol. 7, Apr. 5, 2017, 9 pages.

Neval et al, "Antibody-Targeted Chemotherapy for the Treatment of Melanoma", Cancer Research, vol. 76, No. 13, Jul. 1, 2016, pp. 3954-3964.
Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.
Nishida et al, English Translation of "Clinical Trials of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.
Ortaldo et al., "Effects of several species of human leukocyte interferon on cytotoxic activity a fNK cells and monocytes," International Journal of Cancer, Mar. 15, 1983 (Mar. 15, 1983) vol. 31, No. 3, pp. 285-289.
Ouichi, "Antibody delivery—from basics to clinical test—Clinical development of antibody-drug conjugate", Drug Deliv. Sys. 28(5):424-429 (2013).
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Petrelli et al., "Targeted Delivery for Breast Cancer Therapy: the History of Nanoparticle-Albumin-Bound Paclitaxel," Expert Opinion on Pharmacotherapy, Jun. 1, 2010 (Jun. 1, 2010), vol. 11, pp. 1413-1432.
Qu Na et al: "Cabazitaxel-loaded human serum albumin nanoparticles as a therapeutic agent against prostate cancer", International Journal of Nanomedicine, vol. 11, Jul. 26, 2016 (Jul. 26, 2016), pp. 3451-3459.
Rudikoff et al., "Single amino acid substitution altering antigen-binding specificity," Proc Natl Acad Sci USA 1982 vol. 79 pp. 1979-1983.
Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.
Soda et al., "Latest topics of new medicine Albumin-bound paclitaxel," Mol. Respiratory Dis. 17(1):100-103 (Mar. 1, 2013).
Stancovski et al., "Mechanistic aspects of the opposing effects of monoclonal antivodies to the ERBB2 receptor on tumor growth," Proc Natl Acad Sci USA, 88: 8691-8695, (1991).
Terui, English Translation of Molecular-Targeted Therapy for Cancer: Progresses, and Challenges, "Daratumumab, Antibody Drug against Myeloma", Pharma Med., Nov. 10, 2013, vol. 31, No. 11, p. 27-30.
Vishnu et al., "Safety and Efficacy of nab-Paclitaxel in the Treatment of Patients with Breast cancer," Breast Cancer: Basic and Clinical Research. 2011, vol. 5, pp. 53-65.
Volk et al., "Nab-paclitaxel efficacy in the orthotopic model of human breast cancer is significantly enhanced by concurrent anti-vascular endothelial growth factor A therapy," Neoplasia 10(6):613-623 (2008).
Volk-Draper et al, "Novel Model for Sesaloid Triple-negative Breast Cancer: Behavior In Vivo and Response to Therapy", vol. 14, No. 10, Oct. 1, 2012, 18 pages.
Washington University School of Medicine "Phase I/II Study of Abraxane in Recurrent and Refractory Lymphoma", ClinicalTrials. gov, Dec. 6, 2016, 7 pages.
Yu et al., "Interaction between bevacizumab and murine VEGF-A: a reassessment," Invest. Ophthalmol. Visual Sci. 49 (2): 522-527, Feb. 2008.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
U.S. Appl. No. 15/225,428, office action dated Jul. 31, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2019.
U.S. Appl. No. 15/452,669; office action dated Jun. 24, 2019.
U.S. Appl. No. 15/456,377; office action dated Jul. 5, 2019.
U.S. Appl. No. 15/456,382; office action dated Jul. 8, 2019.

(56) References Cited

OTHER PUBLICATIONS

U.S. Appl. No. 15/456,391; office action dated Jul. 24, 2019.
Beers et al. "CD20 as a Target for Therapeutic Type I and II Monoclonal Antibodies", Seminars in Hematology 47 (2):107-114 (2010).
Belldegrun et al. "Human Renal Carcinoma Line Transfected with Interleukin-2 and/or Interferon alpha Gene(s): Implications for Live Cancer Vaccines", J National Cancer Institute 85(3):207-216 (1993).
Buechner "Intralesional interferon alfa-2b in the treatment of basal cell carcinoma", J Am Acad Dermatol 24:731-734 (1991).
Doveil et al. "Adjuvant Therapy of Stage IIIb Melanoma with Interferon Alfa-2b:Clinical and Immunological Relevance", Dermatology 191:234-239 (1995).
European Application No. 17736453.6, Extended European Search Report dated Jul. 8, 2019.
Khallouf et al. "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-alpha acquire mature dendritic and natural killer cell properties as shown by gene expression analysis", J Translated Medicine 5:46 (2007) (11 pages).
Anonymous, "Phase I/II Study of Abraxane in Recurrent and Refractory Lymphoma", NCT01555853, ClinicalTrials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/331,754; office action dated Feb. 22, 2019.
U.S. Appl. No. 15/412,581, office action dated Mar. 8, 2010.
U.S. Appl. No. 15/412,610, office action dated Mar. 14, 2019.
U.S. Appl. No. 15/414,533; office action dated Mar. 8, 2019.
U.S. Appl. No. 15/430,411, office action dated May 1, 2019.
U.S. Appl. No. 15/456,377; office action dated Mar. 19, 2019.
U.S. Appl. No. 15/456,382; office action dated Mar. 18, 2019.
U.S. Appl. No. 15/456,391; office action dated Mar. 15, 2019.
U.S. Appl. No. 15/456,395; office action dated Mar. 28, 2019.
U.S. Appl. No. 15/456,399; office action dated Mar. 28, 2019.
U.S. Appl. No. 15/460,552; office action dated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization, pp. 10-18 (2004).
Cheng et al. Molecularly targeted drugs for metastatic colorectal cancer. Drug Des Devel Ther. Nov. 1, 2013 ;7: 1315-22 (Year: 2013).
Coiffier "The Role of Rituximab in Lymphomas", Rev. Bras. Hematol. Hemoter., 2002, vol. 24, No. 3, ISSN: 1516-8484 (6 pages).
Edwards et al. The Remarkable Flexibility of the Human Antibody Repertoire; Isolation Over One Thousand Different Antibodies to a Single Protein, BLyS, J. Mol. Biol 334:103-118 (2003).
European Application No. 16837869.3, Extended European Search Report dated Apr. 4, 2019.
International Prelmninary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137 dated Mar. 21, 2019.
Iqbal et al. Anti-Cancer Actions of Denosumab. Curr Osteoporos Rep. Dec. 2011;9(4): 173-6. (Year: 2011).
Matthay et al. Promising therapeutic targets in neuroblastoma. Clin Cancer Res. May 15, 2012;18(10):2740-53. (Year: 2012).
Package Insert, Campath® (Alemtuzumab), Millennium and ILEX Partners, LP, 13 pages, available May 2001.
Reck et al. "Ipilimumab in combination with paclitaxel and carboplatin as first-line therapy in extensive-disease-small-cell lung cancer results from randomized, double-blind, multicenter phase 2 trial", Ann Oncol. 24(1):75-83 (2013).
Robak, T. Emerging monoclonal antibodies and related agents for the treatment of chronic lymphocytic leukemia. Future Oneal. Jan. 2013;9(1):69-91. Abstract Only, (Year: 2013).
Verma et al. "Effect of surface properties on nanoparticle-cell interactions", Small, 6(1 ): 12-21. (2010).
U.S. Appl. No. 15/456,395; office action dated Aug. 14, 2019.
U.S. Appl. No. 15/456,399; office action dated Aug. 14, 2019.
U.S. Appl. No. 15/460,552; office action dated Aug. 14, 2019.
U.S. Appl. No. 15/460,699; office action dated Aug. 28, 2019.
U.S. Appl. No. 15/461,288; office action dated Aug. 28, 2019.
International Preliminary Report on Patentability for Application No. PCT/US2017/050134 dated Mar. 21, 2019.
U.S. Appl. No. 15/187,672, office action dated Sep. 11, 2019.
U.S. Appl. No. 15/752,155; office action dated Sep. 25, 2019.
Cirstoiu-Hapca et al, "Benefit of anti-HER2-coated paclitaxel-loaded immuno-nanoparticles in the treatment of disseminated ovarian cancer: Therapeutic efficacy and biodistribution in mice", Journal of Controlled Release 144:324-331 (2010).
Liu et al. "Freeze-Drying of Proteins". In: Walkers W., Oldenhof H. (eds) Cryopreservative and Freeze-Drying Protocols. Methods in Molecular Biology (Methods and Protocols), vol. 1257, Springer, New York, NY; published online Nov. 14, 2014.

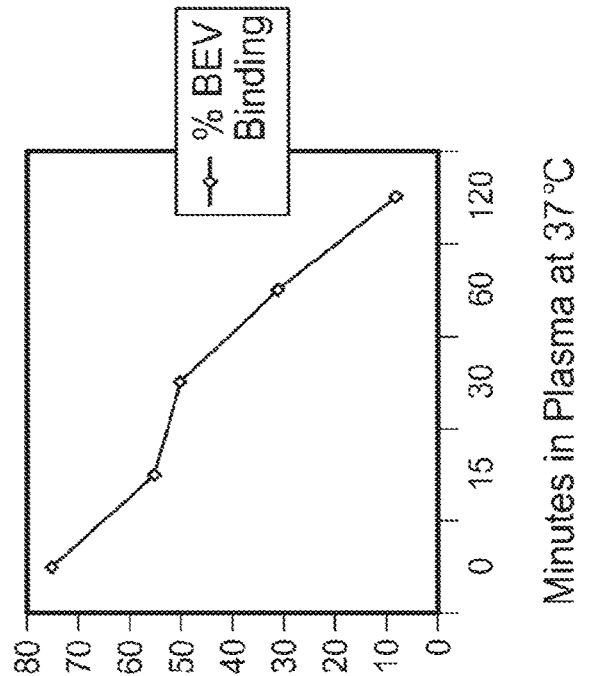
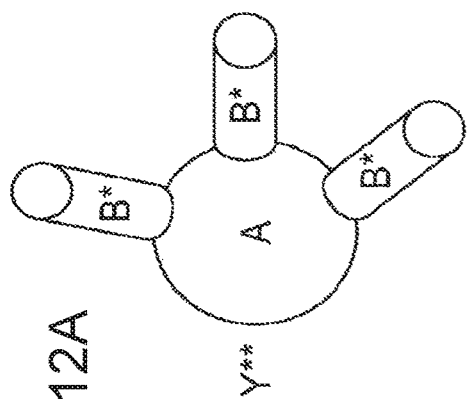
FIG. 12A
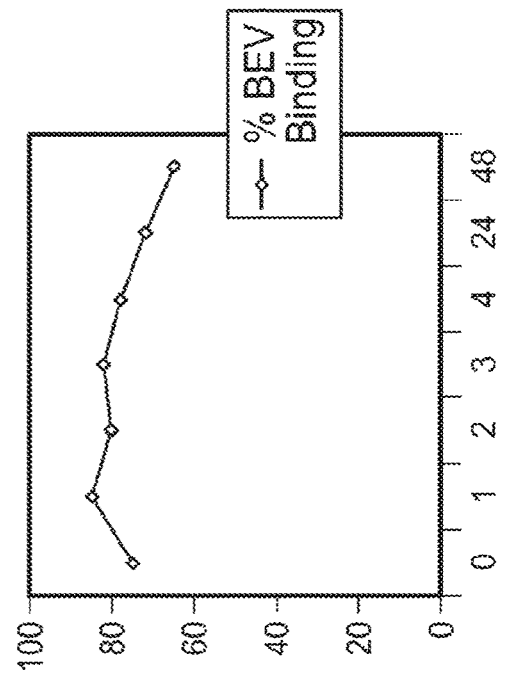
FIG. 12B
FIG. 12C

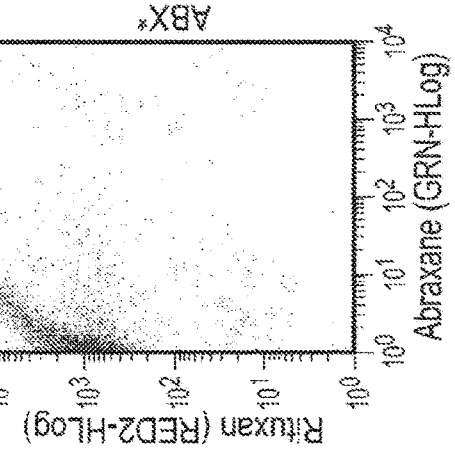
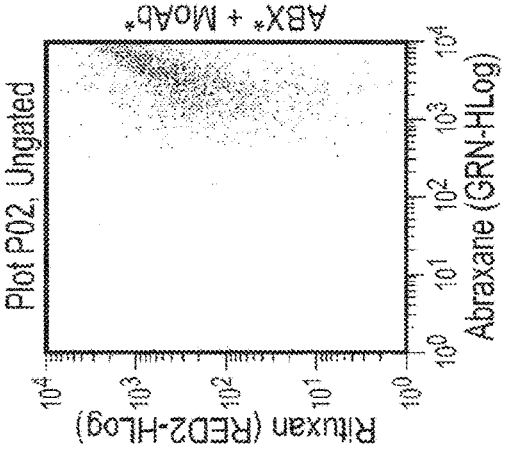
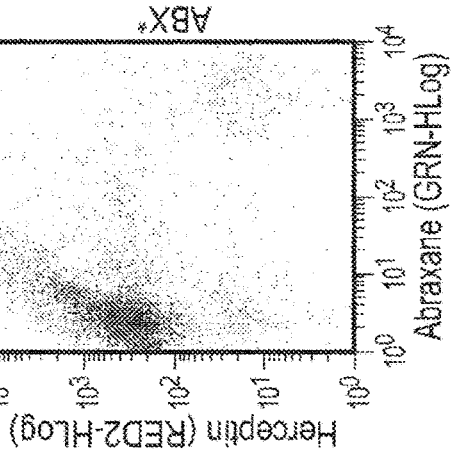
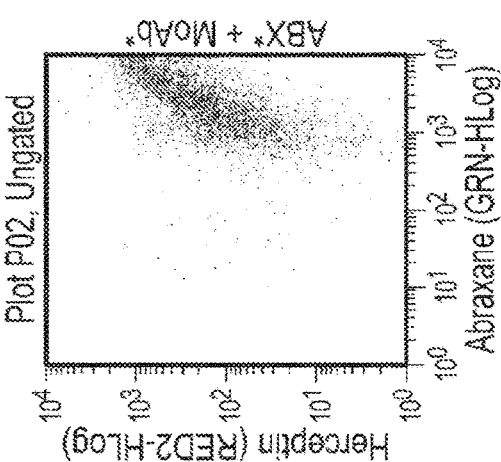
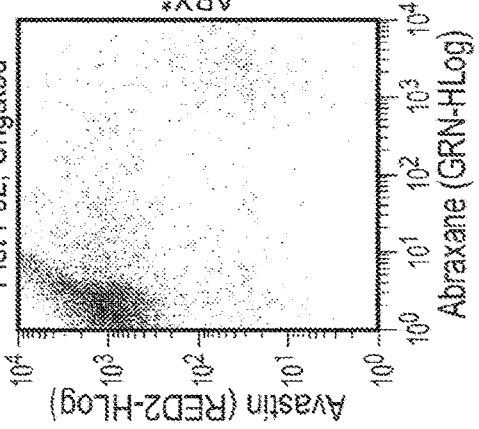
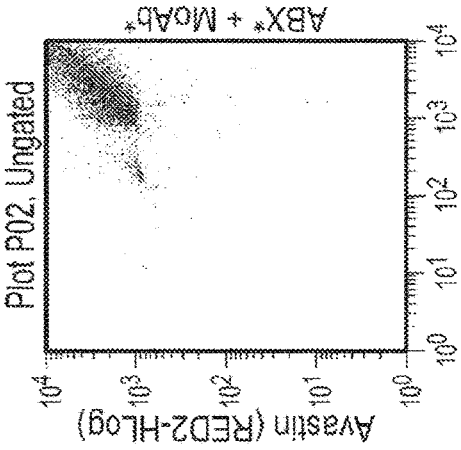

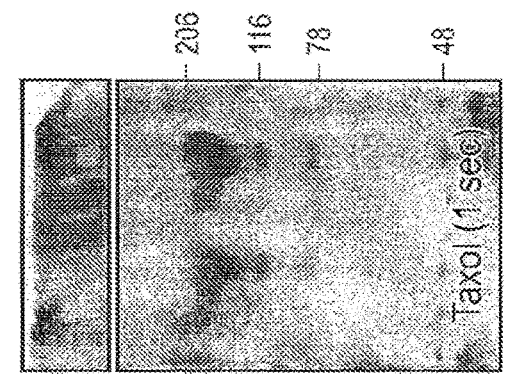
FIG. 15A  FIG. 15B
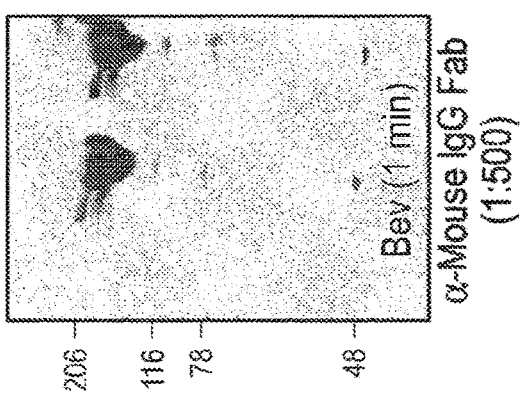
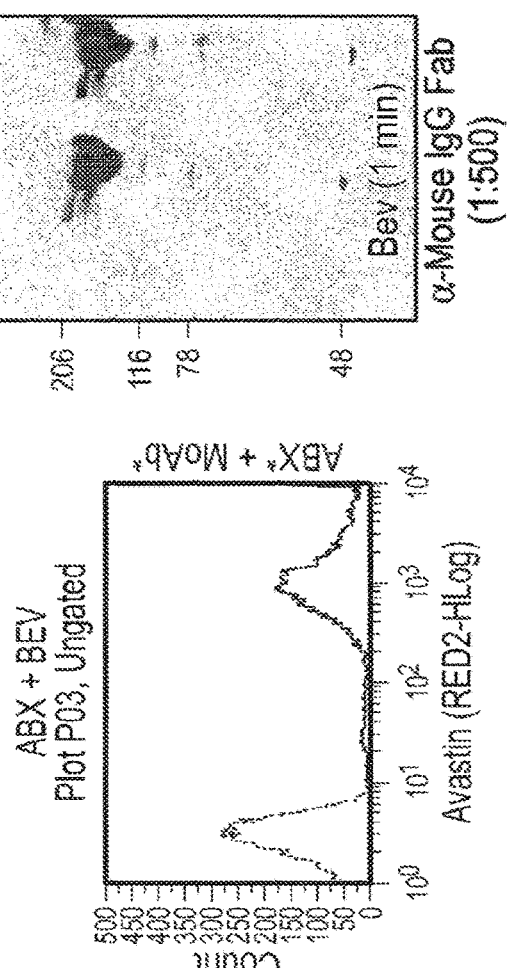
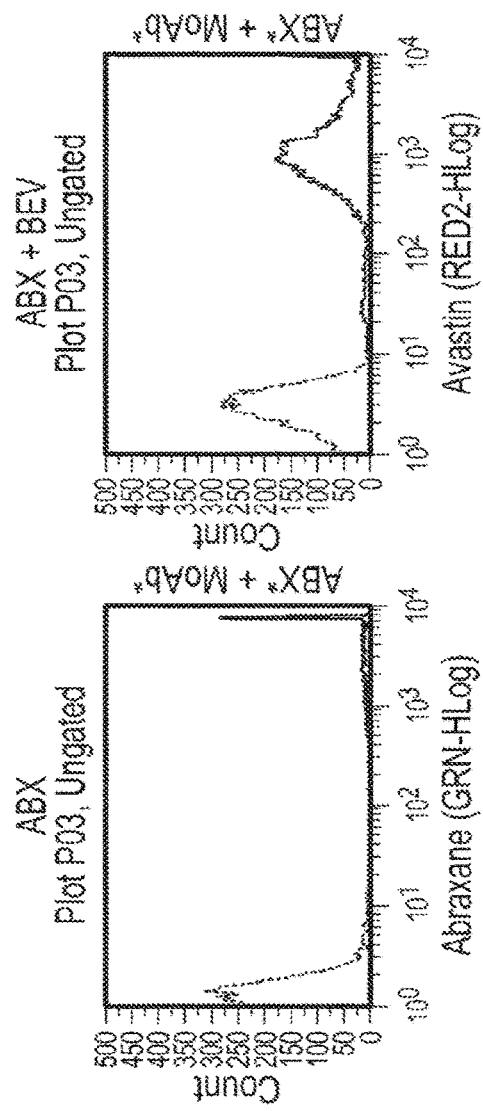
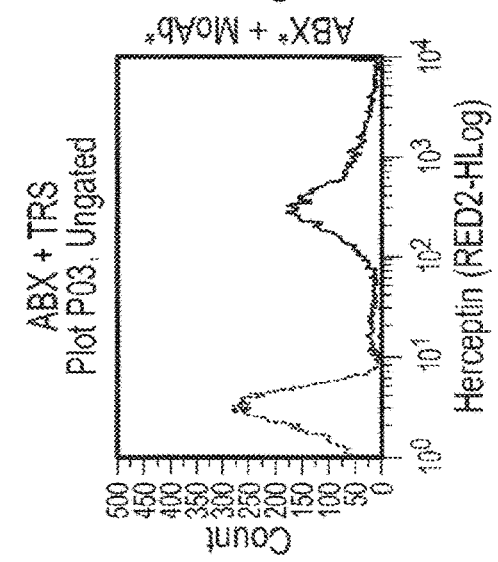

FIG. 16A Particle Size Distribution — ABX 1mg/ml BEV (4 hours)

FIG. 16B Particle Size Distribution — ABX 10 mg/ml BEV (4 hours)

FIG. 16C Particle Size Distribution — ABX:BEV 1mg/ml ON (over night)

FIG. 16D Particle Size Distribution — ABX:BEV 10 mg/ml ON (over night)

Particle Size Distribution

FIG. 17A — ABX:BEV 1mg/ml

Particle Size Distribution

FIG. 17B — ABX:BEV 1mg/ml spun

Particle Size Distribution

FIG. 17C — ABX:BEV 2mg/ml

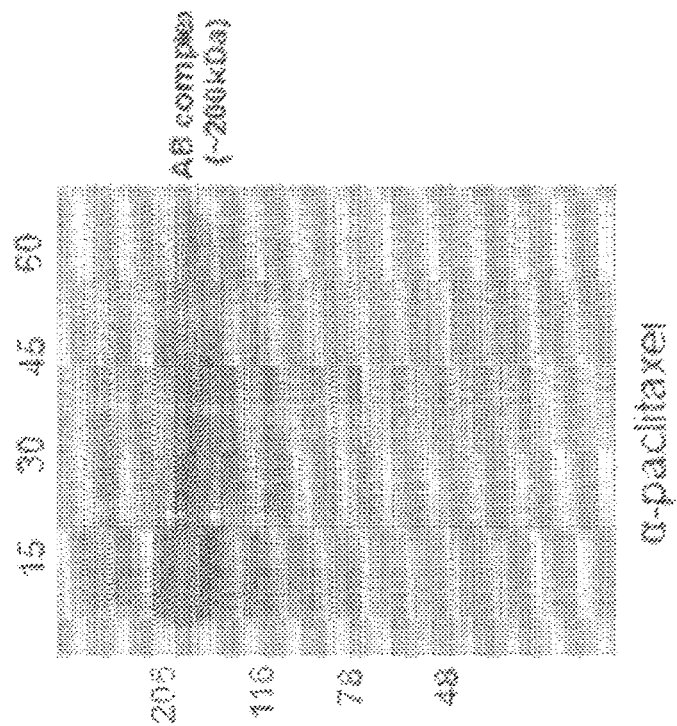
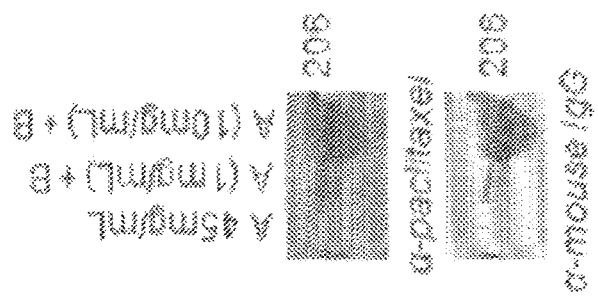
FIG. 21B
FIG. 21A

Abraxane and nanoAB breakdown in plasma at 37 degrees C

Lane 1: Bev (1.25mg)
Lane 2: Plasma + NanoAB (2.5mg) – 30min
Lane 3: Plasma + NanoAB (2.5mg) – 1hr
Lane 4: Plasma + NanoAB (2.5mg) – 1.5hr
Lane 5: Plasma + NanoAB (2.5mg) – 2 hr
Lane 6: Plasma + NanoAB (2.5mg) – 3hr

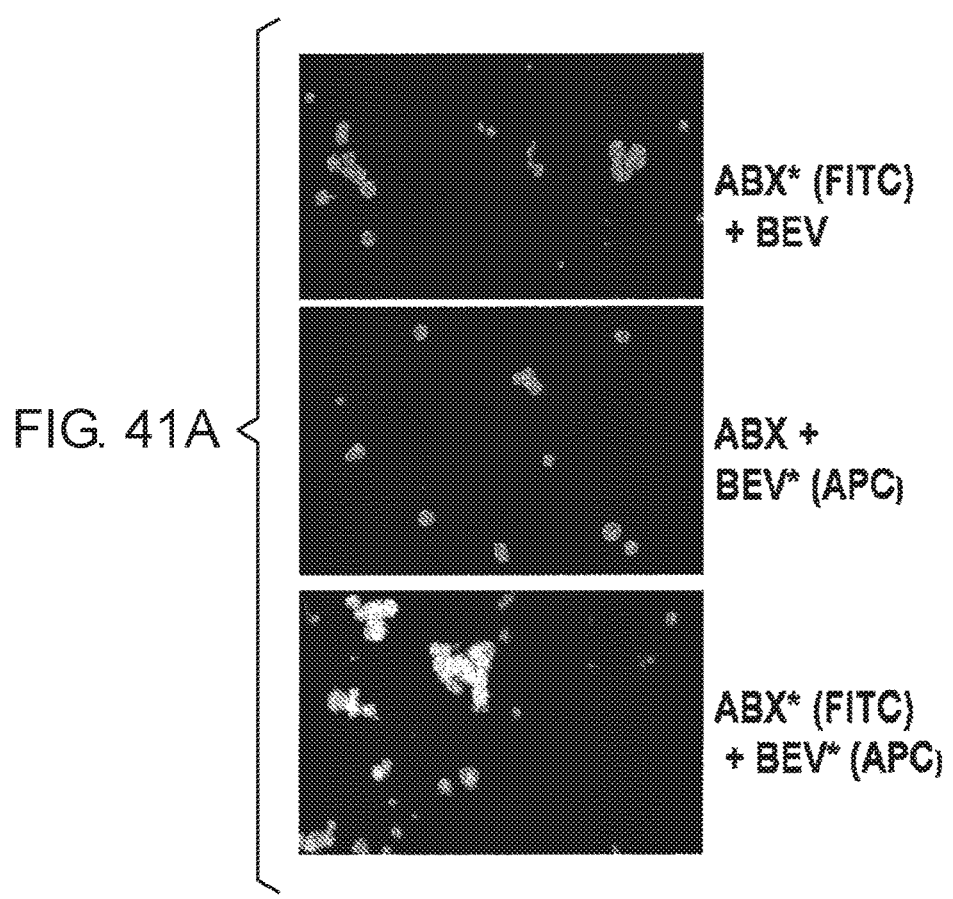

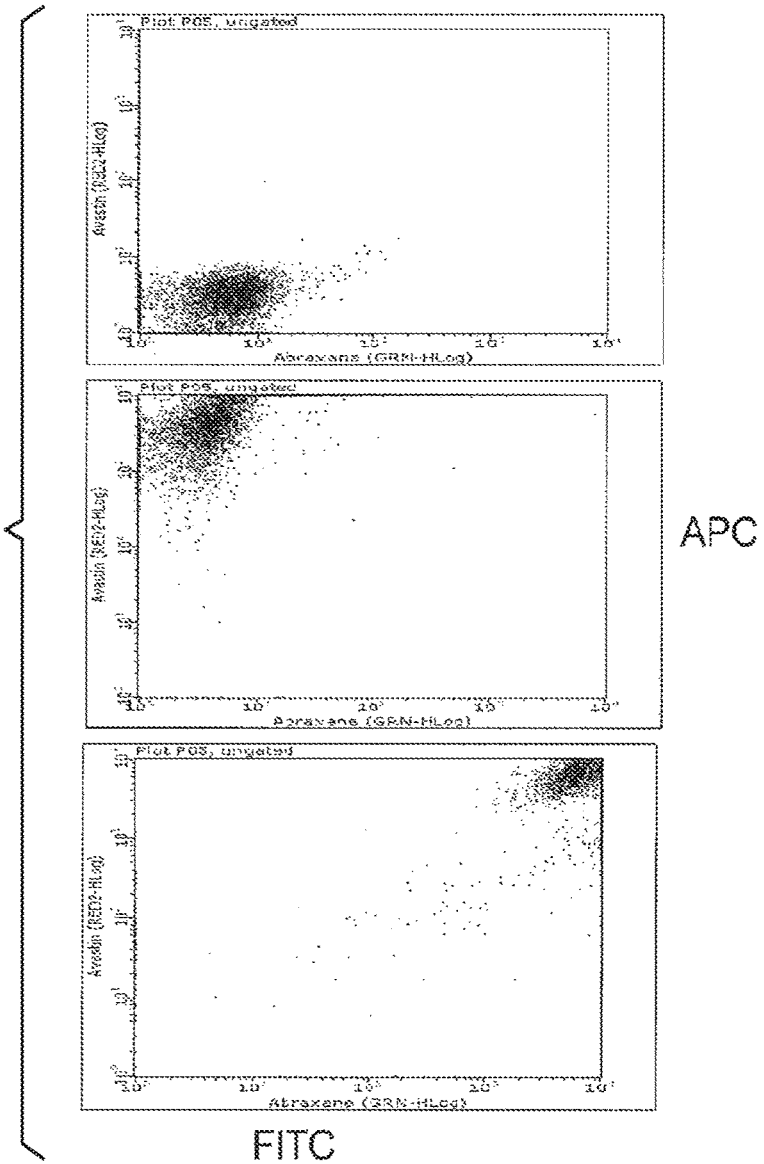

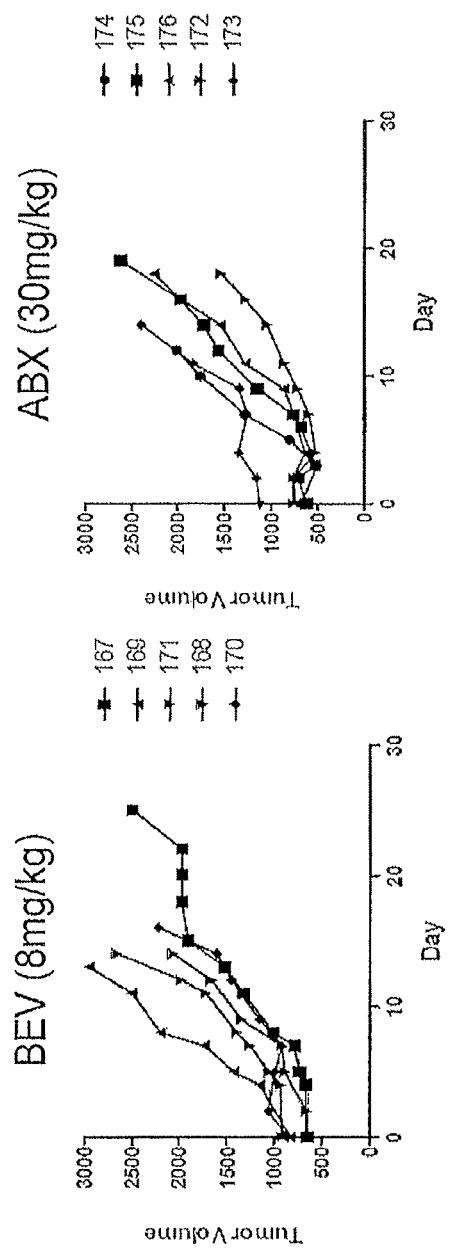

NANOPARTICLE COMPLEXES OF RITUXIMAB, ALBUMIN AND PACLTAXEL

CROSS-REFERENCE TO RELATED APPLICATIONS

This application is a continuation of U.S. application Ser. No. 15/202,115, filed Jul. 5, 2016, which is a continuation of U.S. application Ser. No. 14/432,979, filed Apr. 1, 2015, which is a National Stage Application under 35 U.S.C. § 371 of International Application No. PCT/US2013/062638, having an international filing date of Sep. 30, 2013, which claims the benefit of U.S. Provisional Application Ser. No. 61/708,575, filed Oct. 1, 2012, and U.S. Provisional Application Ser. No. 61/725,293, filed Nov. 12, 2012. The disclosure of the prior applications are considered part of (and are incorporated by reference in) the disclosure of this application.

BACKGROUND

1. Technical Field

This document relates to methods and materials involved in treating cancer (e.g., skin cancers such as melanoma). For example, this document relates to methods and materials involved in using complexes containing albumin-containing nanoparticles (e.g., ABRAXANE® nanoparticles) and antibodies (e.g., anti-VEGF polypeptide antibodies such as AVASTIN® to treat cancer. This document also relates to methods and materials involved in using ABRAXANE® in combination with an anti-VEGF polypeptide antibody (e.g., AVASTIN®) to treat skin cancer.

2. Background Information

Melanoma is the most serious form of skin cancer. It is a malignant tumor that originates in melanocytes, the cells which produce the pigment melanin that colors skin, hair, and eyes and is heavily concentrated in most moles. While it is not the most common type of skin cancer, melanoma underlies the majority of skin cancer-related deaths. About 48,000 deaths worldwide are registered annually as being due to malignant melanoma. Worldwide, there are about 160,000 new cases of melanoma each year. Melanoma is more frequent in white men and is particularly common in white populations living in sunny climates. Other risk factors for developing melanoma include a history of sunburn, excessive sun exposure, living in a sunny climate or at high altitude, having many moles or large moles, and a family or personal history of skin cancer.

Melanomas fall into four major categories. Superficial spreading melanoma can travel along the top layer of the skin before penetrating more deeply. Lentigo maligna typically appears as a flat or mildly elevated mottled tan, brown, or dark brown discoloration and is found most often in the elderly. Nodular melanoma can occur anywhere on the body as a dark, protuberant papule or a plaque that varies from pearl to gray to black. Acral-lentiginous melanoma, although uncommon, is the most common form of melanoma in blacks. It can arise on palmar, plantar, or subungual skin. Metastasis of melanoma occurs via lymphatics and blood vessels. Local metastasis results in the formation of nearby satellite papules or nodules that may or may not be pigmented. Direct metastasis to skin or internal organs can occur.

SUMMARY

This document provides methods and materials involved in treating cancer (e.g., skin cancers such as melanoma). For example, this document provides methods and materials for using complexes containing albumin-containing nanoparticles (e.g., ABRAXANE® nanoparticles) and antibodies (e.g., anti-VEGF polypeptide antibodies such as AVASTIN®) to treat cancer. This document also provides methods and materials involved in using ABRAXANE® in combination with an anti-VEGF polypeptide antibody (e.g., AVASTIN®) to treat skin cancer (e.g., melanoma). ABRAXANE® is available from Celgene Corp. and is a nanoparticle formulation that combines paclitaxel with human albumin. AVASTIN® is also known as bevacizumab and is available from Genentech Corp. and Roche Corp. AVASTIN® is a humanized monoclonal antibody that binds to vascular endothelial growth factor A. As described herein, in vitro mixing of albumin-containing nanoparticles (e.g., ABRAXANE® nanoparticles) and antibodies (e.g., bevacizumab, bevacizumab, trastuzamab, or rituxan) can result in the formation of macromolecular complexes, the characteristics of which (e.g., size, antibody content, or chemotherapeutic drug content) can be customized depending on need. In some cases, such macromolecular complexes can retain antibody mediated target binding specificity, can retain or exhibit enhanced chemotherapeutic tumor cell cytotoxicity, and can exhibit no additional toxicity beyond that of ABRAXANE® nanoparticles alone. As also described herein, contacting ABRAXANE® with an anti-VEGF polypeptide antibody (e.g., AVASTIN®) prior to administration to a human (e.g., a human melanoma cancer patient) can result in a complex that, when administered as a complex, has an increased ability to treat melanoma as compared to a treatment regimen that includes administering ABRAXANE® and the anti-VEGF polypeptide antibody separately in a manner that does not form ABRAXANE®/anti-VEGF polypeptide antibody complexes.

The methods and materials provided herein can be used to increase the progression-free survival rate in skin cancer patients. Increasing progression-free survival can allow skin cancer patients to live longer.

In general, one aspect of this document features a method for treating a mammal having skin cancer. The method comprises, or consists essentially of, administering to the mammal a composition containing ABRAXANE®/anti-VEGF polypeptide antibody complexes (or complexes of (a) an anti-VEGF polypeptide antibody and (b) human albumin-containing nanoparticles having an agent other than paclitaxel) under conditions wherein the length of progression-free survival is increased. The mammal can be a human. The skin cancer can be melanoma. The skin cancer can be stage IV melanoma. In some cases, a composition comprising ABRAXANE®/AVASTIN® complexes can be administered to the mammal. The composition can comprise an alkylating agent. The alkylating agent can be a platinum compound. The platinum compound can be carboplatin. The anti-VEGF polypeptide antibody can be a humanized antibody. The anti-VEGF polypeptide antibody can be bevacizumab. The composition can be administered by injection. The progression-free survival can be increased by 25 percent. The progression-free survival can be increased by 50 percent. The progression-free survival is increased by 75 percent. The progression-free survival can be increased by 100 percent. The composition can be administered under conditions wherein the time to progression is increased.

In another aspect, this document features a method for treating a mammal having cancer. The method comprises, or consists essentially of, administering, to the mammal, a composition comprising albumin-containing nanoparticle/antibody complexes, wherein the average diameter of the complexes is between 0.1 and 0.9 µm. The mammal can be a human. The cancer can be skin cancer. The skin cancer can be melanoma. The skin cancer can be stage IV melanoma. The albumin-containing nanoparticle/antibody complexes can be ABRAXANE®/AVASTIN® complexes. The composition or the albumin-containing nanoparticle/antibody complexes can comprise an alkylating agent. The alkylating agent can be a platinum compound. The platinum compound can be carboplatin. The antibodies of the albumin-containing nanoparticle/antibody complexes can be anti-VEGF polypeptide antibodies. The anti-VEGF polypeptide antibodies can be humanized antibodies. The anti-VEGF polypeptide antibodies can be bevacizumab. The composition can be administered by injection. The administration of the composition can be effective to increase progression-free survival by 25 percent. The administration of the composition can be effective to increase progression-free survival by 50 percent. The administration of the composition can be effective to increase progression-free survival by 75 percent. The administration of the composition can be effective to increase progression-free survival by 100 percent. The administration of the composition can be under conditions wherein the median time to progression for a population of mammals with the cancer is at least 150 days. The administration of the composition can be under conditions wherein the median time to progression for a population of mammals with the cancer is at least 165 days. The administration of the composition can be under conditions wherein the median time to progression for a population of mammals with the cancer is at least 170 days. The average diameter of the complexes can be from 0.1 µm to 0.3 µm. The average diameter of the complexes can be from 0.15 µm to 0.3 µm. The average diameter of the complexes can be from 0.2 µm to 0.5 µm. The average diameter of the complexes can be from 0.3 µm to 0.5 µm. The average diameter of the complexes can be from 0.2 µm to 0.8 µm. The average diameter of the complexes can be from 0.2 µm to 0.7 µm.

In another aspect, this document features a method for treating a mammal having cancer. The method comprises, or consists essentially of, administering, to the mammal, a composition comprising albumin-containing nanoparticle/antibody complexes, wherein the average diameter of at least 5 percent of the complexes of the composition is between 0.1 and 0.9 µm. The mammal can be a human. The cancer can be skin cancer. The skin cancer can be melanoma. The skin cancer can be stage IV melanoma. The albumin-containing nanoparticle/antibody complexes can be ABRAXANE®/AVASTIN® complexes. The composition or the albumin-containing nanoparticle/antibody complexes can comprise an alkylating agent. The alkylating agent can be a platinum compound. The platinum compound can be carboplatin. The antibodies of the albumin-containing nanoparticle/antibody complexes can be anti-VEGF polypeptide antibodies. The anti-VEGF polypeptide antibodies can be humanized antibodies. The anti-VEGF polypeptide antibodies can be bevacizumab. The composition can be administered by injection. The administration of the composition can be effective to increase progression-free survival by 25 percent. The administration of the composition can be effective to increase progression-free survival by 50 percent. The administration of the composition can be effective to increase progression-free survival by 75 percent. The administration of the composition can be effective to increase progression-free survival by 100 percent. The administration of the composition can be under conditions wherein the median time to progression for a population of mammals with the cancer is at least 150 days. The administration of the composition can be under conditions wherein the median time to progression for a population of mammals with the cancer is at least 165 days. The administration of the composition can be under conditions wherein the median time to progression for a population of mammals with the cancer is at least 170 days. The average diameter of at least 5 percent of the complexes of the composition can be from 0.2 µm to 0.9 µm. The average diameter of at least 5 percent of the complexes of the composition can be from 0.2 µm to 0.8 µm. The average diameter of at least 5 percent of the complexes of the composition can be from 0.2 µm to 0.7 µm. The average diameter of at least 5 percent of the complexes of the composition can be from 0.2 µm to 0.6 µm. The average diameter of at least 5 percent of the complexes of the composition can be from 0.2 µm to 0.5 µm. The average diameter of at least 5 percent of the complexes of the composition can be from 0.2 µm to 0.4 µm. The average diameter of at least 10 percent of the complexes of the composition can be between 0.1 and 0.9 µm. The average diameter of at least 50 percent of the complexes of the composition can be between 0.1 and 0.9 µm. The average diameter of at least 75 percent of the complexes of the composition can be between 0.1 and 0.9 µm. The average diameter of at least 90 percent of the complexes of the composition can be between 0.1 and 0.9 µm.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A depicts A alone. FIG. 2B depicts A plus a V*. FIG. 2C depicts A plus B plus a V*. FIG. 2D depicts A plus V plus a V*, or A plus B plus V plus a V*. The labels are as indicated in FIG. 1. These results demonstrate that A and B spontaneously associate and preserve a VEGF polypeptide binding potential.

In FIG. 4, 100 ng VEGF was used to visualize the complex.

FIGS. 12A-C contain graphs plotting the percent BEV binding for ABX:BEV complexes. FIG. 12A depicts a complex of labeled nab-paclitaxel (ABRAXANE®) and labeled bevacizumab. FIG. 12B depicts complexes exposed to 0.9% saline at room temperature. FIG. 12C depicts complexes exposed to human plasma at 37° C. for the indicated times.

FIG. 14A depicts complexes of ABX and bevacizumab. FIG. 14B depicts complexes of ABX and trastuzumab. FIG. 14C depicts complexes of ABX and rituximab. FIG. 14D depicts complexes of ABX and bevacizumab. FIG. 14E depicts complexes of ABX and trastuzumab. FIG. 14F depicts complexes of ABX and rituximab. FIG. 14G depicts ABX alone. FIG. 14H depicts complexes of ABX and bevacizumab. FIG. 14I depicts complexes of ABX and trastuzumab. FIG. 14J depicts complexes of ABX and rituximab.

FIG. 15A contains a photograph of Western blot analyses of the indicated materials assessed for bevacizumab FIG. 15B contains a photograph of Western blot analyses of the indicated materials assessed for taxol.

FIGS. 16A-D contain graphs of the size distributions of the indicated complexes incubated for the indicated time. FIG. 16A is a graph of complexes of ABX 1 mg/ml BEV incubated for 4 hours. FIG. 16B is a graph of complexes of ABX 10 mg/ml BEV incubated for 4 hours. FIG. 16C is a graph of complexes of ABX 1 mg/ml BEV incubated for overnight. FIG. 16D is a graph of complexes of ABX 10 mg/ml BEV incubated for overnight.

FIGS. 17A-F contain graphs of the size distributions of the indicated complexes incubated for one hour at room temperature. FIG. 17A is a graph of complexes of ABX:BEV 1 mg/ml. FIG. 17B is a graph of complexes of ABX:BEV 1 mg/ml spun.

FIG. 17C is a graph of complexes of ABX:BEV 2 mg/ml. FIG. 17D is a graph of complexes of ABX:BEV 3 mg/ml. FIG. 17E is a graph of complexes of ABX:BEV 4 mg/ml. FIG. 17F is a graph of complexes of ABX:BEV 8 mg/ml.

FIG. 20A is a graph of particle size distribution after 1 hr incubation. FIG. 20B is a graph of particle size distribution after 2 hr incubation. FIG. 20C is a graph of particle size distribution after 4 hr incubation.

FIG. 21A. After a 4 hour incubation at room temperature of ABX:BEV complexes (two different concentrations of ABX) in saline, soluble ABX/BEV complexes were detected by Western blot analysis that migrated in the MW range of approximately 200 kD. Identical bands were identified by Western blotting with anti-paclitaxel (α-paclitaxel) and anti-mouse IgG (α-mouse IgG) antibodies. FIG. 21B. Similarly, following incubation of ABX:BEV complexes in heparinized human plasma at 37° C. for 15, 30, 45, or 60 minutes, the majority of the soluble paclitaxel (α-paclitaxel) migrated at a MW of 200 kD.

FIGS. 23A-C contain graphs plotting percent change (A), tumor size (B), and survival (C) for Group 2 mice treated with PBS (day 0 and day 7), Bevacizumab (8 mg/kg; day 0 and day 7), ABRAXANE® (30 mg/kg; day 0 and day 7), Bevacizumb (day 0, 8 mg/kg) followed by ABRAXANE® (day 1, 30 mg/kg), or small nanoAB (complex; day 0 and day 7).

FIGS. 24A-C contain graphs plotting percent change (A), tumor size (B), and survival (C) for Group 3 mice treated with PBS, Bevacizumab (24 mg/kg), ABRAXANE® (30 mg/kg), Bevacizumb (day 0, 24 mg/kg) followed by ABRAXANE® (day 1, 30 mg/kg), small nanoAB (nanoAB), or big nanoAB.

FIG. 41A contains fluorescent microscopy images and FIG. 41B contains scatter plots from a flow cytometry analysis. These studies, using immunofluorescent labeling of BEV and/or ABX, demonstrate dual labeling of the in vitro AB complexes, and suggest binding of BEV and ABX.

FIGS. 44A-44E are series of graphs plotting tumor volume in nude mice bearing human A375 melanoma xenografts, in which tumors were allowed to grow to a size of 1000 mm³ before initiation of therapy. Mice received bevacizumab (BEV, FIG. 44A), nab-paclitaxel (ABX, FIG. 44B), bevacizumab followed by nab-paclitaxel (BEV+ABX, FIG. 44C), AB160 (FIG. 44D) or saline (PBS, FIG. 44E). The absolute dose of nab-paclitaxel and bevacizumab was identical in all treatment cohorts. Each group included at least 5 mice.

FIG. 45A is a graph plotting mouse plasma bevacizumab levels, demonstrating delayed plasma clearance of bevacizumab when administered as part of AB160 vs alone (five mice/cohort). FIG. 45B is a graph plotting the percentage of immunohistochemical staining for paclitaxel of tumor tissues 24 hours after treatment with either saline (S), nab-paclitaxel (ABX) or AB160 (two mice per cohort, 5 random tissue sections), suggesting an approximately 50% increase in the number of paclitaxel positive staining tumor cells after mice were treated with AB160 over that of ABX alone. A similar increase in staining was observed with anti-human Ig IHC detecting human bevacizumab (greater number of cells in the AB160 cohort vs ABX or saline). FIG. 45C is a graph plotting the percentage of paclitaxel and Ig IHC staining for mice treated with ABX or AB160. There was no correlation (R values of 0.0229 and 0.0176 per mouse) between the levels of paclitaxel and Ig IHC staining for mice treated with ABX, but a suggestion of correlation (R values of 0.7445 and 0.5496, per mouse) in mice treated with AB160.

DETAILED DESCRIPTION

Figure 1:
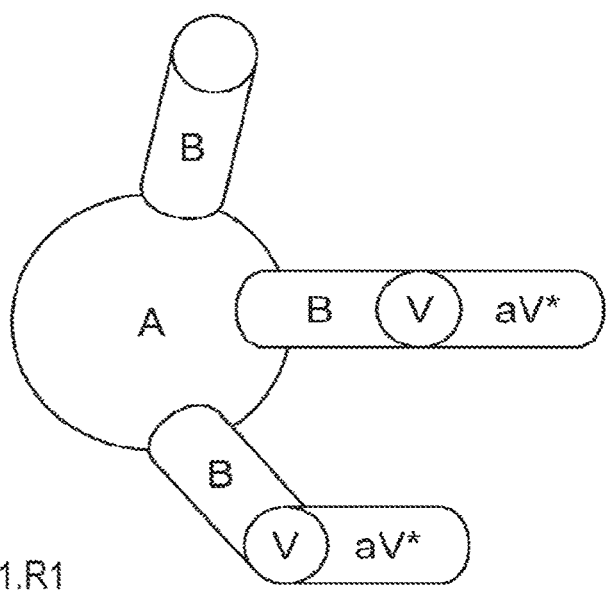
FIG. 1 is a diagram of an ABRAXANE® nanoparticle (labeled A) complexed with an anti-VEGF polypeptide antibody (bevacizumab; labeled B). In two of the three cases, the anti-VEGF polypeptide antibody is shown binding to a VEGF-A polypeptide (labeled V), and a fluorescently-labeled anti-VEGF antibody (labeled aV*) is shown bound to the VEGF-A polypeptide.
Figure 2A:
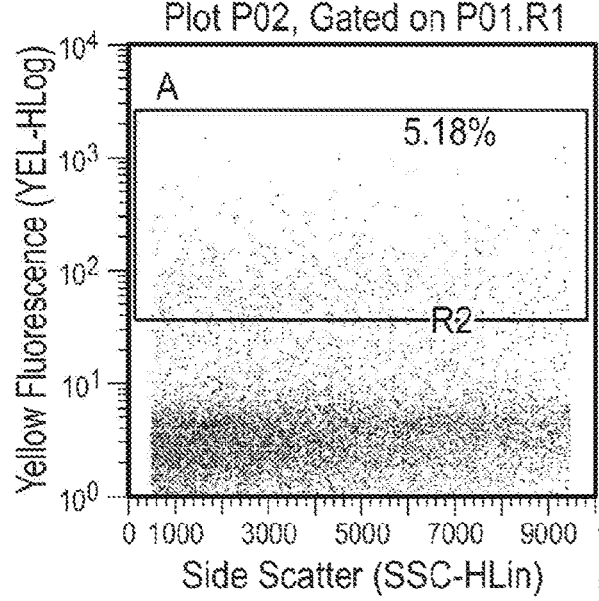
FIGS. 2A-2E contain scatter plots of a flow cytometry analysis plotting the level of yellow fluorescence.
Figure 2B:
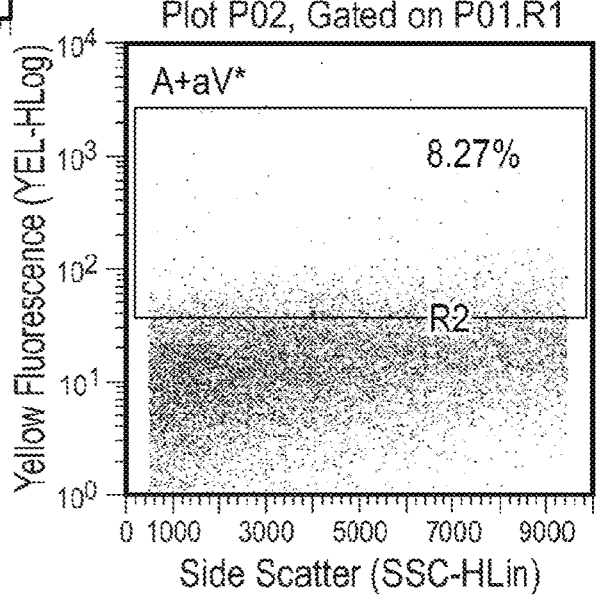
Figures 2C, 2D, 2E:
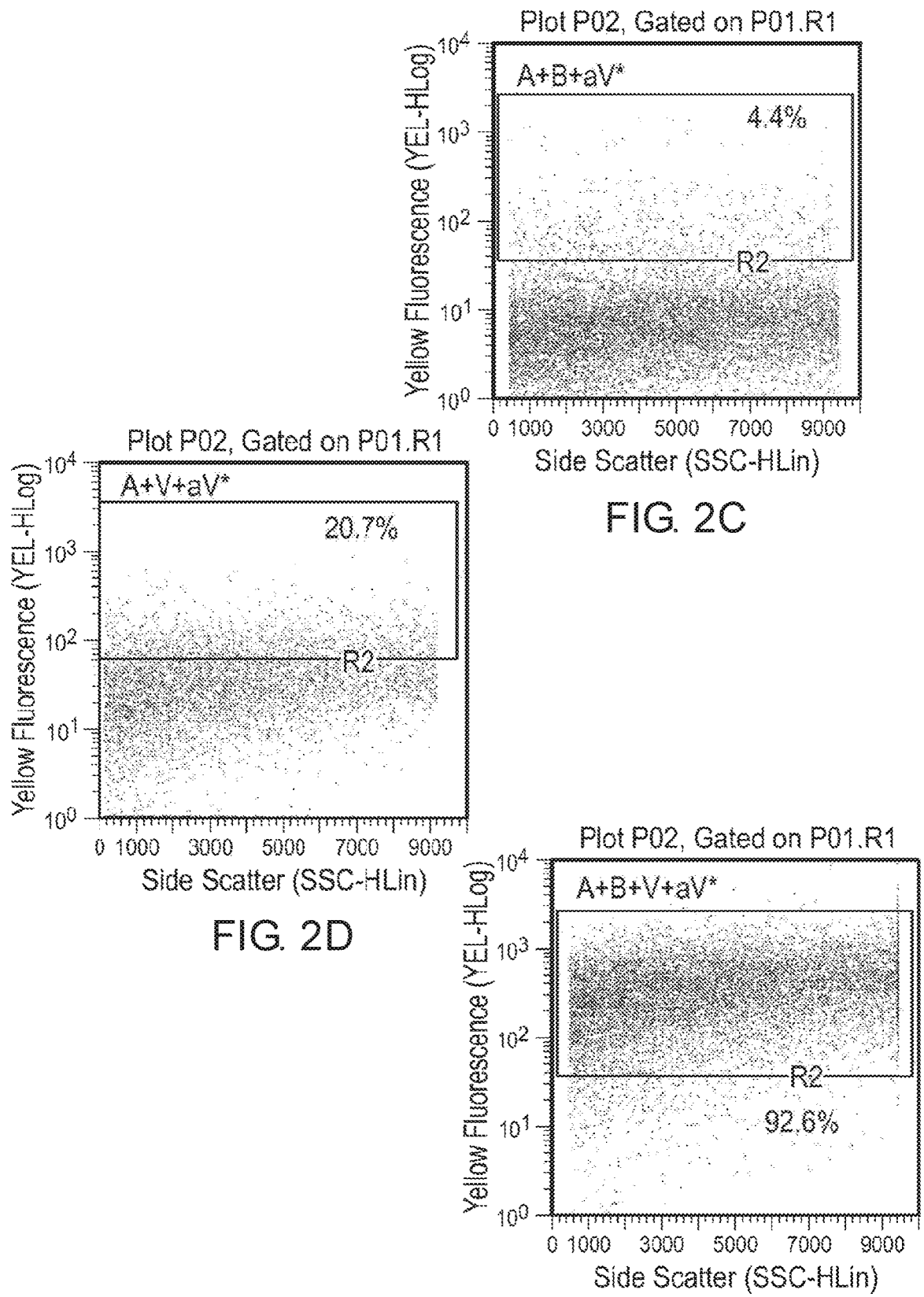
Figure 3:
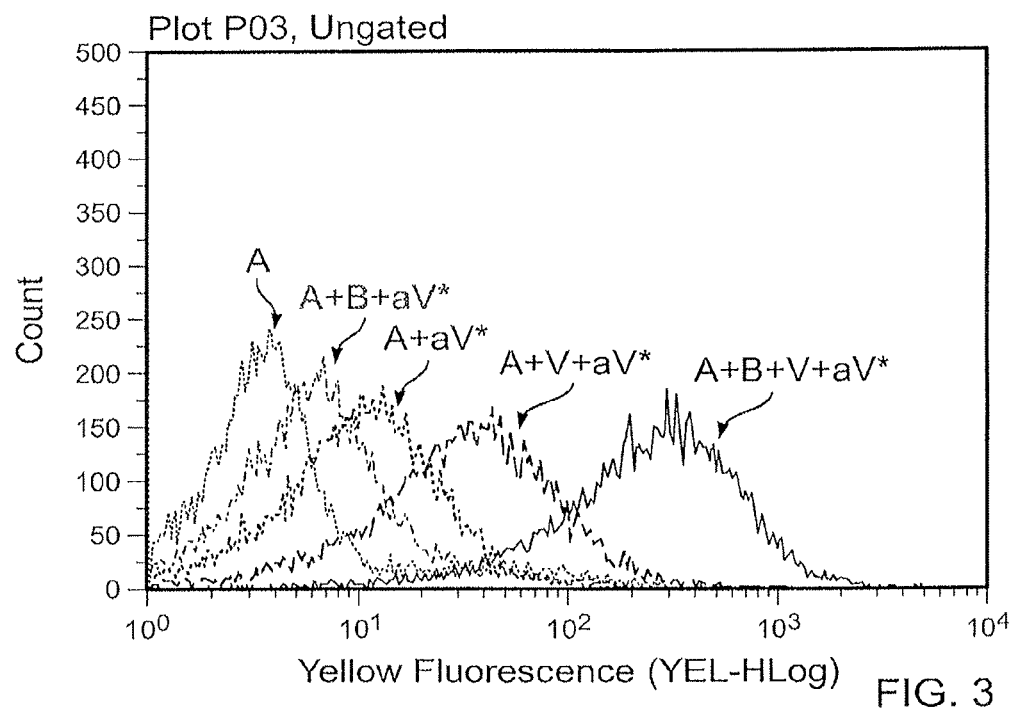
FIG. 3 is graph that contains the flow cytometry data from FIG. 2.
Figure 4:
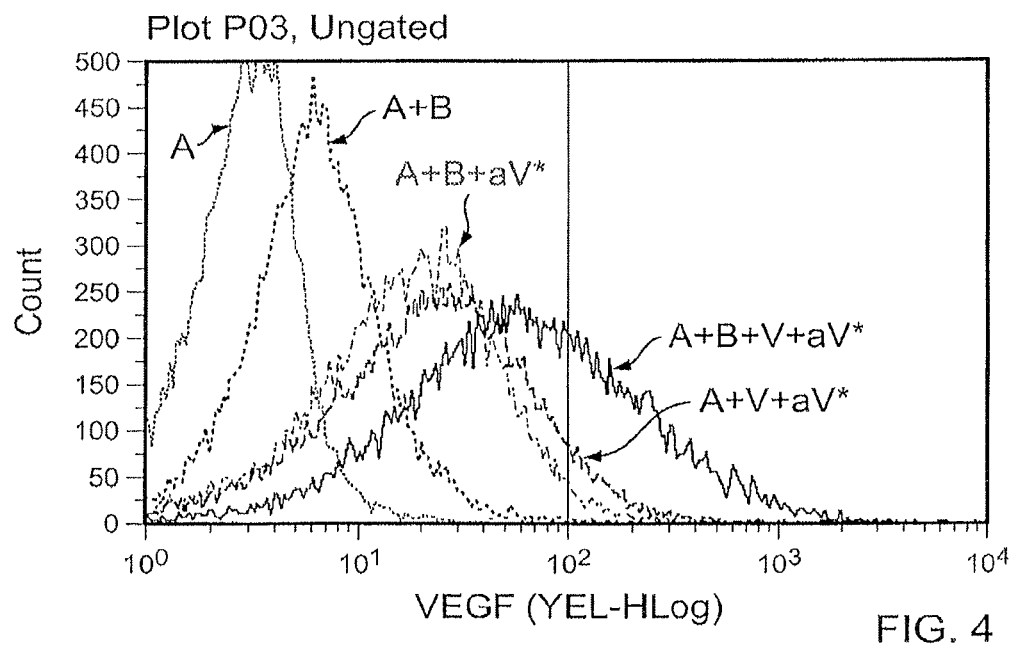
FIG. 4 is a repeat of the experiment of FIG. 3, comparing A alone, A plus aV*, A plus B plus aV*, A plus V plus aV*, or A plus B plus V plus aV*. One difference is in FIG. 3, 500 ng of VEGF was used.
Figure 5:
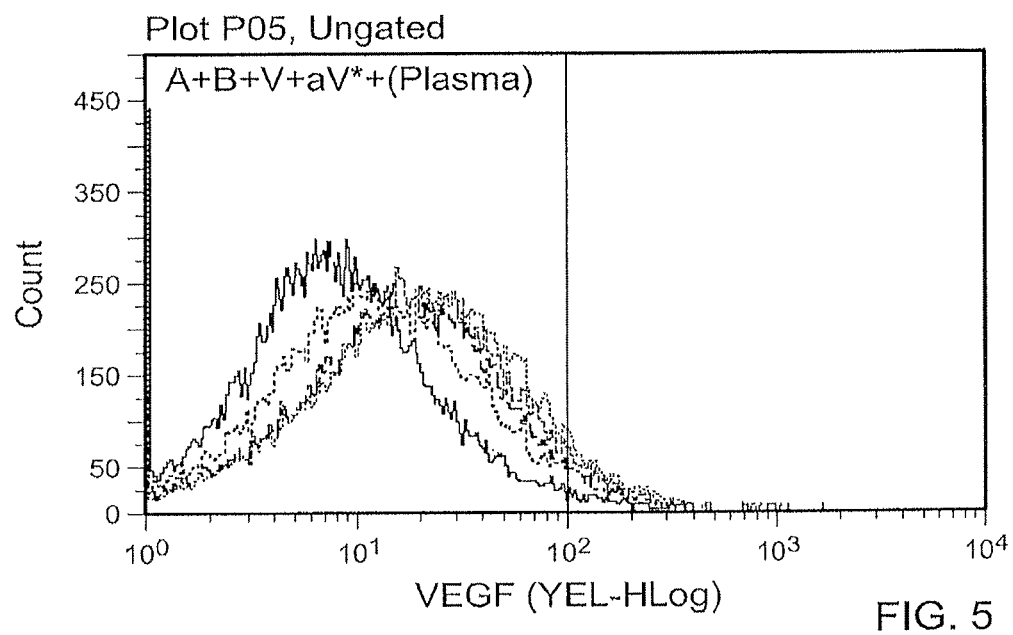
FIG. 5 is a graph plotting flow cytometry data of A plus B incubated in the presence of various concentrations of human plasma (1:1 to 1:16) followed by addition of V and aV*. These results indicate that human plasma diluted in a range of relative volumes (1:1 to 1:16) successfully inhibited the formation of the A+B complex relative to controls.
Figure 6:
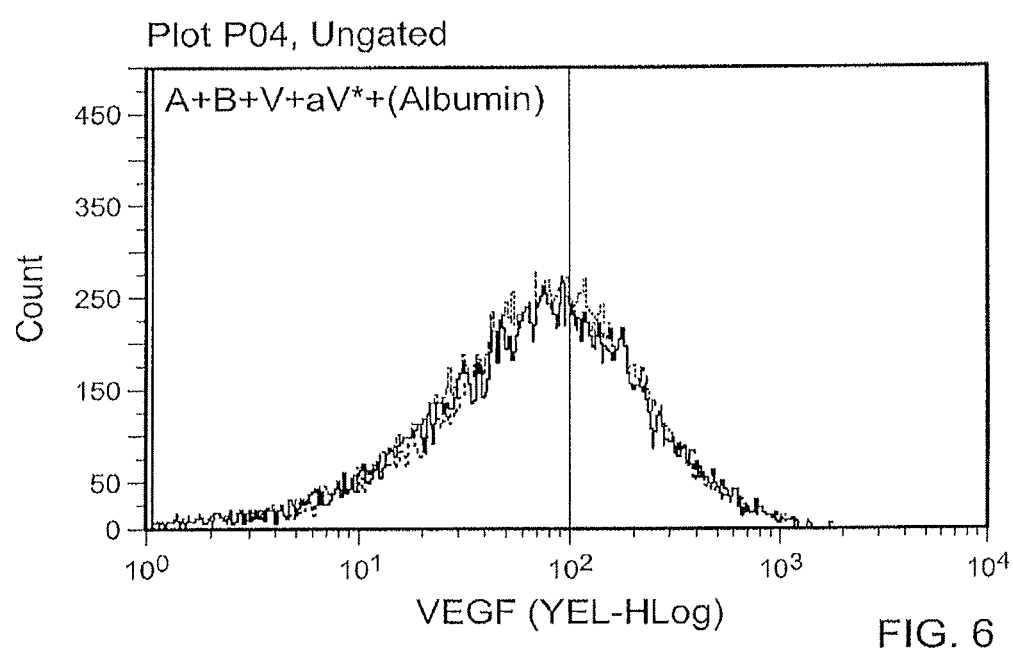
FIG. 6 is a graph plotting flow cytometry data of A plus B incubated in the presence of various concentrations of human serum albumin (500 µg, 50 µg, 5 g, 0.5 µg, and 0.05 µg/mL) followed by addition of V and aV*. These results indicate that incubation with serum albumin (concentrations ranging from 500 µg/mL to 0.05 µg/mL) did not affect the complexing of A and B.
Figure 7:
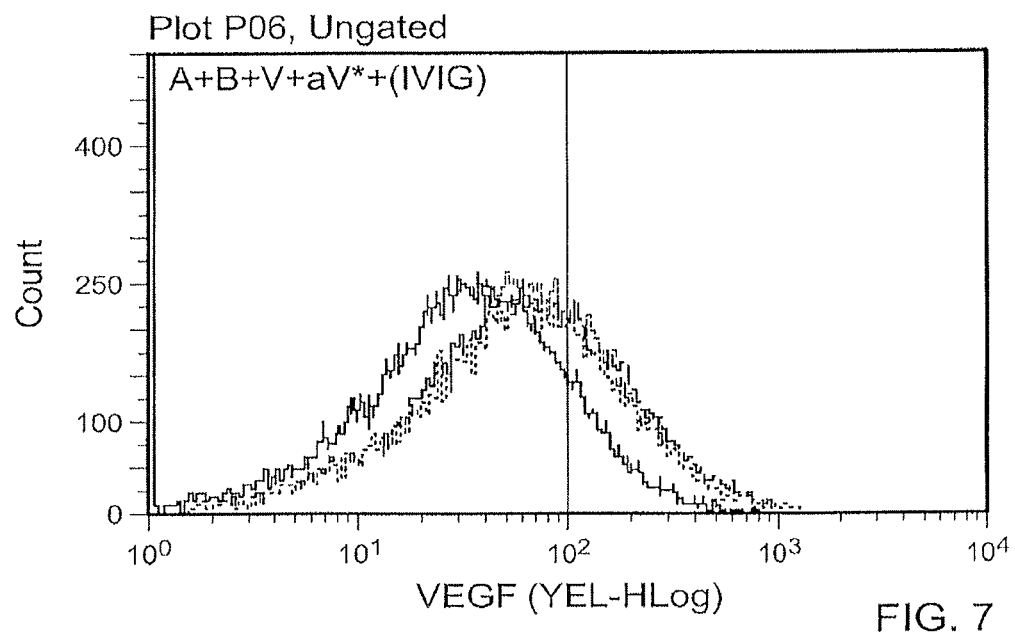
FIG. 7 is a graph plotting flow cytometry data of A plus B incubated in the presence of various concentrations of human polyclonal immunoglobulin (500 µg, 50 µg, 5 µg, 0.5 µg, and 0.05 µg/mL) followed by addition of V and aV*. These results indicate that incubation of A and B with a range of concentrations of human immunoglobulin (IVIG; 500 µg/mL to 0.05 µg/mL) partially inhibited A and B complexing.
Figure 8:
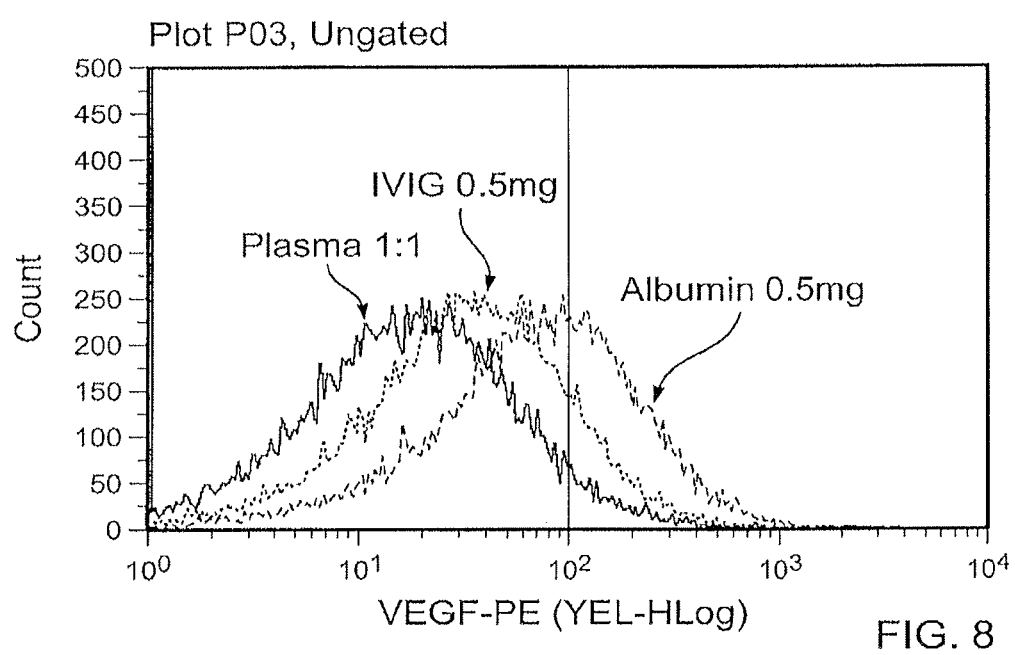
FIG. 8 contain A plus B complexing results in the presence of plasma (1:1), IVIG (0.5 mg/mL), or albumin (0.5 mg/mL). At the highest concentrations of plasma (1:1), IVIG (0.5 mg/mL), or albumin (0.5 mg/mL) tested, the levels of relative inhibition of A plus B complexing differ in diminishing order.

This document provides methods and materials involved in treating cancer (e.g., skin cancers such as melanoma). For example, this document provides methods and materials for using complexes containing albumin-containing nanoparticles (e.g., ABRAXANE® nanoparticles) and antibodies (e.g., anti-VEGF polypeptide antibodies such as AVASTIN®) to treat cancer.

The methods and materials provided herein can be used to treat any type of cancer. For example, the methods and materials provided herein can be used to treat skin cancer (e.g., melanoma) and breast cancer. In some cases, the methods and materials provided herein can be used to treat cancer (e.g., skin cancer) in any type of mammal including, without limitation, mice, rats, dogs, cats, horses, cows, pigs, monkeys, and humans. When treating skin cancer, any type of skin cancer, such as melanoma, can be treated using the methods and materials provided herein. For example, stage 1, stage 11, stage III, or stage IV melanoma can be treated. In some cases, a lymph node positive, a lymph node negative, or a metastatic melanoma can be treated as described herein.

In some cases, complexes containing albumin-containing nanoparticles (e.g., ABRAXANE® nanoparticles) and antibodies (e.g., anti-VEGF polypeptide antibodies such as AVASTIN®) can be designed to have an average diameter that is greater than 1 µm. For example, appropriate concentrations of albumin-containing nanoparticles and antibodies can be used such that complexes having an average diameter that is greater than 1 µm are formed. In some cases, manipulations such as centrifugation can be used to form preparations of albumin-containing nanoparticle/antibody complexes where the average diameter of those complexes is greater than 1 µm. In some cases, the preparations of albumin-containing nanoparticle/antibody complexes provided herein can have an average diameter that is between 1 µm and 5 µm (e.g., between 1.1 µm and 5 µm, between 1.5 µm and 5 µm, between 2 µm and 5 µm, between 2.5 µm and 5 µm, between 3 µm and 5 µm, between 3.5 µm and 5 µm, between 4 µm and 5 µm, between 4.5 µm and 5 µm, between 1.1 µm and 4.5 µm, between 1.1 µm and 4 µm, between 1.1 µm and 3.5 µm, between 1.1 µm and 3 µm, between 1.1 µm and 2.5 µm, between 1.1 µm and 2 µm, or between 1.1 µm and 1.5 µm). Preparations of albumin-containing nanoparticle/antibody complexes provided herein having an average diameter that is between 1 µm and 5 µm can be administered systemically (e.g., intravenously) to treat cancers located within a mammal's body. In some cases, the preparations of albumin-containing nanoparticle/antibody complexes provided herein can have an average diameter that is between 5 pun and 50 µm (e.g., between 6 µm and 50 µm, between 7 µm and 50 µm, between 10 µm and 50 µm, between 15 µm and 50 µm, between 20 µm and 50 µm, between 25 µm and 50 µm, between 30 µm and 50 µm, between 35 µm and 50 pun, between 5 µm and 45 µm, between 5 µm and 40 µm, between 5 µm and 35 µm, between 5 µm and 30 µm, between 5 µm and 25 µm, between 5 µm and 20 µm, between 5 µm and 15 µm, or between 10 µm and 30 µm). Preparations of albumin-containing nanoparticle/antibody complexes provided herein having an average diameter that is between 5 µm and 50 µm can be administered into a tumor (e.g., intratumorally) or in a region of a tumor located within a mammal's body.

In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 1 pun and 5 µm (e.g., between 1.1 µm and 5 µm, between 1.5 µm and 5 µm, between 2 µm and 5 µm, between 2.5 µm and 5 pun, between 3 µm and 5 µm, between 3.5 µm and 5 µm, between 4 µm and 5 µm, between 4.5 pun and 5 µm, between 1.1 µm and 4.5 pun, between 1.1 µm and 4 µm, between 1.1 µm and 3.5 µm, between 1.1 µm and 3 µm, between 1.1 µm and 2.5 µm, between 1.1 pun and 2 µm, or between 1.1 µm and 1.5 µm). Preparation of albumin-containing nanoparticle/antibody complexes provided herein having greater than 60 percent (e.g., greater than 65, 70, 75, 80, 90, 95, or 99 percent) of the complexes with a diameter that is between 1 µm and 5 µm can be administered systemically (e.g., intravenously) to treat cancers located within a mammal's body. In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 5 µm and 50 µm (e.g., between 6 µm and 50 µm, between 7 µm and 50 µm, between 10 µm and 50 µm, between 15 µm and 50 µm, between 20 µm and 50 µm, between 25 µm and 50 µm, between 30 µm and 50 µm, between 35 µm and 50 µm, between 5 µm and 45 µm, between 5 µm and 40 µm, between 5 µm and 35 µm, between 5 µm and 30 µm, between 5 µm and 25 µm, between 5 µm and 20 µm, between 5 µm and 15 µm, or between 10 µm and 30 µm). Preparation of albumin-containing nanoparticle/antibody complexes provided herein having greater than 60 percent (e.g., greater than 65, 70, 75, 80, 90, 95, or 99 percent) of the complexes with a diameter that is between 5 µm and 50 µm can be administered into a tumor (e.g., intratumorally) or in a region of a tumor located within a mammal's body.

In some cases, complexes containing albumin-containing nanoparticles (e.g., ABRAXANE® nanoparticles) and antibodies (e.g., anti-VEGF polypeptide antibodies such as AVASTIN® can be designed to have an average diameter that is less than 1 µm. For example, appropriate concentrations of albumin-containing nanoparticles and antibodies can be used such that complexes having an average diameter that is less than 1 µm are formed. In some cases, the preparations of albumin-containing nanoparticle/antibody complexes provided herein can have an average diameter that is between 0.1 µm and 1 µm (e.g., between 0.1 µm and 0.95 µm, between 0.1 µm and 0.9 µm, between 0.1 µm and 0.8 µm, between 0.1 µm and 0.7 µm, between 0.1 µm and 0.6 µm, between 0.1 µm and 0.5 µm, between 0.1 µm and 0.4 µm, between 0.1 µm and 0.3 µm, between 0.1 µm and 0.2 µm, between 0.2 µm and 1 µm, between 0.3 µm and 1 µm, between 0.4 µm and 1 µm, between 0.5 µm and 1 µm, between 0.2 µm and 0.6 µm, between 0.3 µm and 0.6 µm, between 0.2 µm and 0.5 µm, or between 0.3 pun and 0.5 µm). Preparations of albumin-containing nanoparticle/antibody complexes provided herein having an average diameter that is between 0.1 µm and 0.9 µm can be administered systemically (e.g., intravenously) to treat cancers located within a mammal's body.

In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 0.1 µm and 0.9 µm (e.g., between 0.1 µm and 0.95 µm, between 0.1 µm and 0.9 µm, between 0.1 µm and 0.8 µm, between 0.1 µm and 0.7 µm, between 0.1 µm and 0.6 µm, between 0.1 µm and 0.5 µm, between 0.1 µm and 0.4 µm, between 0.1 µm and 0.3 µm, between 0.1 µm and 0.2 µm, between 0.2 µm and 1 µm, between 0.3 µm and 1 µm, between 0.4 µm and 1 µm, between 0.5 µm and 1 µm, between 0.2 µm and 0.6 µm, between 0.3 µm and 0.6 µm, between 0.2 µm and 0.5 µm, or between 0.3 µm and 0.5 µm). Preparation of albumin-containing nanoparticle/antibody complexes provided herein having greater than 60 percent (e.g., greater than 65, 70, 75, 80, 90, 95, or 99 percent) of the complexes with a diameter that is between 0.1 µm and 0.9 µm can be administered systemically (e.g., intravenously) to treat cancers located within a mammal's body.

In general, albumin-containing nanoparticles such as ABRAXANE® can be contacted with an antibody such as an anti-VEGF polypeptide antibody (e.g., AVASTIN®) prior to administration to a human to form an albumin-containing nanoparticle/antibody complex (e.g., an ABRAXANE®/anti-VEGF polypeptide antibody complex). Any appropriate albumin-containing nanoparticle preparation and any appropriate antibody can be used as described herein. For example, ABRAXANE® nanoparticles can be used as described herein. Examples of antibodies that can be used to form albumin-containing nanoparticle/antibody complexes as described herein include, without limitation, bevacizumab (AVASTIN®), trastuzamab, and rituxan. For example, an appropriate dose of ABRAXANE® and an appropriate dose of AVASTIN® can be mixed together in the same container. This mixture can be incubated at an appropriate temperature (e.g., room temperature, between 15° C. and 30° C., between 15° C. and 25° C., between 20° C. and 30° C., or between 20° C. and 25° C.) for a period of time (e.g., about 30 minutes, or between about 5 minutes and about 60 minutes, between about 5 minutes and about 45 minutes, between about 15 minutes and about 60 minutes, between about 15 minutes and about 45 minutes, between about 20 minutes and about 400 minutes, or between about 25 minutes and about 35 minutes) before being administered to a cancer patient (e.g., a melanoma patient). In some cases, ABRAXANE® can be contacted with an anti-VEGF polypeptide antibody by injecting both ABRAXANE® and the anti-VEGF polypeptide antibody either individually or as a pre-mixed combination into an IV bag containing an IV bag solution.

The contents of the IV bag including ABRAXANE®/anti-VEGF polypeptide antibody complexes can be introduced into the patient to be treated.

In some cases, albumin-containing nanoparticles such as ABRAXANE® can be contacted with an antibody such as an anti-VEGF polypeptide antibody (e.g., AVASTIN®) to form albumin-containing nanoparticle/antibody complexes (e.g., ABRAXANE®/anti-VEGF polypeptide antibody complexes) that are stored prior to being administered to a cancer patient (e.g., a melanoma patient). For example, a composition containing albumin-containing nanoparticle/antibody complexes can be formed as described herein and stored for a period of time (e.g., days or weeks) prior to being administered to a cancer patient.

Any appropriate method can be used to obtain albumin-containing nanoparticles such as ABRAXANE® and an antibody such as an anti-VEGF polypeptide antibody. For example, ABRAXANE® can be obtained from Celgene Corp. or as described elsewhere (U.S. Pat. No. 6,537,579). AVASTIN® can be obtained from Genentech Corp. or Roche Corp. or as described elsewhere (U.S. Pat. No. 6,054,297).

In some cases, the combination of an albumin-containing nanoparticle such as ABRAXANE® and an antibody such as anti-VEGF polypeptide antibody can include one or more other agents such as an alkylating agent (e.g., a platinum compound). Examples of platinum compounds that can be used as an alkylating agent include, without limitation, carboplatin (PARAPLATIN®), cisplatin (PLATINOL®), oxaliplatin (ELOXATIN®), and BBR3464. Examples of other agents that can be included within an albumin-containing nanoparticle/antibody complex provided herein include, without limitation, bendamustine, bortezomib, cabazitaxel, chlorambucil, dasatinib, docetaxel, doxorubicin, epirubicin, erlotinib, etoposide, everolimus, gefitinib, idarubicin, hydroxyurea, imatinib, lapatinib, melphalan, mitoxantrone, nilotinib, oxaliplatin, pazopanib, pemetrexed, romidepsin, sorafenib, sunitinib, teniposide, vinblastine, and vinorelbine.

Any appropriate method can be used to administer an albumin-containing nanoparticle/antibody complex provided herein (e.g., ABRAXANE®/anti-VEGF polypeptide antibody complexes) to a mammal. For example, a composition containing albumin-containing nanoparticle/antibody complexes such as ABRAXANE®/anti-VEGF polypeptide antibody complexes can be administered via injection (e.g., subcutaneous injection, intramuscular injection, intravenous injection, or intrathecal injection).

Before administering a composition containing an albumin-containing nanoparticle/antibody complex provided herein (e.g., ABRAXANE®/anti-VEGF polypeptide antibody complexes) to a mammal, the mammal can be assessed to determine whether or not the mammal has cancer (e.g., skin cancer). Any appropriate method can be used to determine whether or not a mammal has cancer (e.g., skin cancer). For example, a mammal (e.g., human) can be identified as having skin cancer using standard diagnostic techniques. In some cases, a tissue biopsy can be collected and analyzed to determine whether or not a mammal has skin cancer.

After identifying a mammal as having cancer (e.g., skin cancer), the mammal can be administered a composition containing albumin-containing nanoparticle/antibody complexes provided herein (e.g., ABRAXANE®/anti-VEGF polypeptide antibody complexes). For example, a composition containing ABRAXANE®/anti-VEGF polypeptide antibody complexes can be administered prior to or in lieu of surgical resection of a tumor. In some cases, a composition containing albumin-containing nanoparticle/antibody complexes provided herein (e.g., ABRAXANE®/anti-VEGF polypeptide antibody complexes) can be administered following resection of a tumor.

A composition containing albumin-containing nanoparticle/antibody complexes provided herein (e.g., ABRAXANE®/anti-VEGF polypeptide antibody complexes) can be administered to a mammal in any appropriate amount, at any appropriate frequency, and for any appropriate duration effective to achieve a desired outcome (e.g., to increase progression-free survival). In some cases, a composition containing albumin-containing nanoparticle/antibody complexes provided herein (e.g., ABRAXANE®/anti-VEGF polypeptide antibody complexes) can be administered to a mammal having cancer (e.g., skin cancer) to reduce the progression rate of the cancer (e.g., melanoma) by 5, 10, 25, 50, 75, 100, or more percent. For example, the progression rate can be reduced such that no additional cancer progression is detected. Any appropriate method can be used to determine whether or not the progression rate of cancer (e.g., skin cancer) is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer (e.g., skin cancer) after treatment can be determined and compared to the stage before treatment to determine whether or not the progression rate was reduced.

In some cases, a composition containing albumin-containing nanoparticle/antibody complexes provided herein (e.g., ABRAXANE®/anti-VEGF polypeptide antibody complexes) can be administered to a mammal having cancer (e.g., skin cancer) under conditions where progression-free survival is increased (e.g., by 5, 10, 25, 50, 75, 100, or more percent) as compared to the median progression-free survival of corresponding mammals having untreated cancer (e.g., untreated skin cancer) or the median progression-free survival of corresponding mammals having cancer (e.g., skin cancer) treated with ABRAXANE® and an antibody (e.g., an anti-VEGF polypeptide antibody) without forming ABRAXANE®/antibody complexes (e.g., without forming ABRAXANE®/anti-VEGF polypeptide antibody complexes). In some cases, a composition containing albumin-containing nanoparticle/antibody complexes provided herein (e.g., ABRAXANE®/anti-VEGF polypeptide antibody complexes) can be administered to a mammal having cancer (e.g., skin cancer) to increase progression-free survival by 5, 10, 25, 50, 75, 100, or more percent as compared to the median progression-free survival of corresponding mammals having cancer (e.g., skin cancer) and having received ABRAXANE® or an antibody (e.g., an anti-VEGF polypeptide antibody) alone. Progression-free survival can be measured over any length of time (e.g., one month, two months, three months, four months, five months, six months, or longer).

In some cases, a composition containing albumin-containing nanoparticle/antibody complexes provided herein (e.g., ABRAXANE®/anti-VEGF polypeptide antibody complexes) can be administered to a mammal having cancer (e.g., skin cancer) under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing albumin-containing nanoparticle/antibody complexes provided herein (e.g., ABRAXANE®/anti-VEGF polypeptide antibody complexes). In some cases, a composition containing albumin-containing nanoparticle/antibody complexes provided herein (e.g., ABRAXANE®/anti-VEGF polypeptide antibody complexes) can be administered to a mammal having cancer (e.g., skin cancer) under conditions where the median time to progression for a population of mammals is at least 150 days (e.g., at least 155, 160, 163, 165, or 170 days).

An effective amount of a composition containing albumin-containing nanoparticle/antibody complexes provided herein (e.g., ABRAXANE®/anti-VEGF polypeptide antibody complexes) can be any amount that reduces the progression rate of cancer (e.g., skin cancer), increases the progression-free survival rate, or increases the median time to progression without producing significant toxicity to the mammal. Typically, an effective amount of ABRAXANE® can be from about 50 mg/m$^2$ to about 150 mg/m$^2$ (e.g., about 80 mg/m$^2$), and an effective amount of an anti-VEGF polypeptide antibody such as bevacizumab can be from about 5 mg/kg to about 20 mg/kg (e.g., about 10 mg/kg). If a particular mammal fails to respond to a particular amount, then the amount of ABRAXANE® or anti-VEGF polypeptide antibody can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer (e.g., skin cancer) may require an increase or decrease in the actual effective amount administered.

The frequency of administration can be any frequency that reduces the progression rate of cancer (e.g., skin cancer), increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing ABRAXANE®/anti-VEGF polypeptide antibody complexes can include rest periods. For example, a composition containing ABRAXANE®/anti-VEGF polypeptide antibody complexes can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the skin cancer may require an increase or decrease in administration frequency.

An effective duration for administering a composition provided herein can be any duration that reduces the progression rate of cancer (e.g., skin cancer), increases the progression-free survival rate, or increases the median time to progression without producing significant toxicity to the mammal. Thus, the effective duration can vary from several days to several weeks, months, or years. In general, the effective duration for the treatment of skin cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer (e.g., skin cancer).

A composition containing albumin-containing nanoparticle/antibody complexes provided herein (e.g., ABRAXANE®/anti-VEGF polypeptide antibody complexes) can be in any appropriate form. For example, a composition provided herein can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

After administering a composition provided herein to a mammal, the mammal can be monitored to determine whether or not the cancer (e.g., skin cancer) was treated. For example, a mammal can be assessed after treatment to determine whether or not the progression rate of melanoma was reduced (e.g., stopped). As described herein, any method can be used to assess progression and survival rates.

In some cases, a formulation of ABRAXANE®/AVASTIN® complexes described in Example 1 can be administered to a human melanoma patient as described in the methods set forth in Example 10.

In some cases, nanoparticles containing albumin (e.g., nanoparticles with an albumin shell) and an agent other than placitaxel can be used as described herein in place of or in combination with ABRAXANE®. For example, albumin-containing nanoparticles designed to carry a cancer chemotherapeutic agent can be used to form nanoparticle/anti-VEGF polypeptide antibody complexes that can be used as described herein. An example of such a cancer chemotherapeutic agent includes, without limitation, vinblastine.

In some cases, a composition can be formulated to include nanoparticles containing albumin (e.g., nanoparticles with an albumin shell) that are conjugated to an antibody, agent, or combination of antibodies and agents listed in Table 1 to form complexes for treating cancer. For example, albumin nanoparticles can be formulated to include Cetuximab to treat head and neck cancer. In some cases, albumin nanoparticles can be formulated to include Cetuximab and vinblastine as complexes to treat head and neck cancer. In some cases, a composition can be formulated to include nanoparticles containing albumin (e.g., nanoparticles with an albumin shell) that are conjugated to a combination of different antibodies or agents listed in Table 1 to form complexes capable of treating multiple different cancers. For example, albumin nanoparticles can be formulated to include Herceptin, Bevacizumab, and Docetaxel as complexes for treating breast cancer and ovarian cancer.

TABLE 1

List of possible antibodies and agents for forming anti-cancer complexes with albumin.

| Cancer | Antibody | Agent |
| --- | --- | --- |
| Head and neck cancer | Cetuximab | vinblastine |
| Breast cancer | Herceptin | Docetaxel; doxorubicin; epirubicin; Everolimus; gefitinib; lapatinib; |

TABLE 1-continued

List of possible antibodies and agents for forming anti-cancer complexes with albumin.

| Cancer | Antibody | Agent |
| --- | --- | --- |
| | | mitoxantrone; pemetrexed; sunitinib; vinblastine; vinorelbine |
| Colon cancer | Bevacizumab; Cetuximab; Panitumumab | Oxaliplatin; pemetrexed; sunitinib |
| Ovarian cancer | Bevacizumab | Docetaxel; doxorubicin; epirubicin; hydroxyurea; melphalan; oxaliplatin; pazopanib |
| Lung cancer | Bevacizumab | Docetaxel; doxorubicin; epirubicin; erlotinib; etoposide; gefitinib; pazopanib; pemetrexed; sunitinib; vinblastine; vinorelbine |
| Pancreatic cancer | | Erlotinib; sunitinib |
| Bladder cancer | | Doxorubicin; pemetrexed |
| myeloma | | Bortezomib; melphalan |
| CLL/lymphoma | Ofatumumab; Alemtuzumab | Bendamustine; |
| Prostate cancer | | Cabazitaxel; docetaxel |
| CLL | | chlorambucil |
| CML/ALL | | dasatinib |
| Stomach cancer | Herceptin | Doxorubicin; epirubicin |
| Leukemia (AML, ANLL, ALL) | Rituximab | Doxorubicin; idarubicin; imatinib; mitoxantrone; nilotinib; teniposide |
| Hodgkin's disease | | Chlorambucil; doxorubicin; vinblastine |
| non-Hodgkin's lymphoma | | Chlorambucil; doxorubicin; mitoxantrone |
| Thyroid cancer | | Doxorubicin |
| Bone sarcoma | | Doxorubicin |
| Wilms' tumor | | Doxorubicin |
| Kaposi's sarcoma | | Etoposide |
| Ewing's sarcoma | | Etoposide |
| Testicular cancer | | Etoposide; vinblastine |
| Lymphoma | Rituximab | Etoposide; romidepsin |
| renal cell carcinoma | Bevacizumab | Everolimus; pazopanib; sorafenib; sunitinib |
| melanoma | | Hydroxyurea; melphalan |
| gastrointestinal stromal tumors | | Imatinib; sunitinib |
| Soft tissue sarcoma | | pazopanib |
| Cervical cancer | | pemetrexed |
| Hepatocellular carcinoma | | sorafenib |

In some cases, nanoparticles containing albumin (e.g., nanoparticles with an albumin shell) or a complex described herein (e.g., ABRAXANE®/AVASTIN® complexes) can be formulated to include one or more anti-chronic inflammation treatment agents designed to reduce the global state of immune dysfunction and/or chronic inflammation present within a cancer patient. For example, steroidal anti-inflammatory agents (e.g., prednisone), non-steroidal anti-inflammatory agents (e.g., naproxen), lympho-depleting cytotoxic agents (e.g., cyclophosphamide), immune cell and/or cytokine targeting antibodies (e.g., infliximab), or a combination thereof can be incorporated into nanoparticles containing albumin or ABRAXANE®/AVASTIN® complexes. In some cases, anti-IL-4 agents (e.g., anti-IL-4 antibodies), anti-IL-13 agents (e.g., soluble IL-13 receptor), and combinations thereof can be incorporated into nanoparticles containing albumin or ABRAXANE®/AVASTIN® complexes.

Any appropriate method can be used to assess whether or not the global state of immune dysfunction and/or chronic inflammation was reduced following an anti-chronic inflammation treatment. For example, cytokine profiles (e.g., IL-4, IL-13, IL-4, IL-13, IL-5, IL-10, IL-2, and interferon gamma) present in blood can be assessed before and after an anti-chronic inflammation treatment to determine whether or not the global state of immune dysfunction and/or chronic inflammation was reduced.

The invention will be further described in the following examples, which do not limit the scope of the invention described in the claims.

EXAMPLES

Example 1—Contacting ABRAXANE® with AVASTIN® Results in the Formation of ABRAXANE®/AVASTIN® Complexes ABRAXANE® (1 mg/mL) and AVASTIN (25 mg/mL) were stored at 4° C. 10 μg (10 μL) of ABRAXANE® nanoparticles and 500 μg (20 μL) of AVASTIN were mixed in a total volume of 30 μL. The ABRAXANE® and AVASTIN were incubated at room temperature for 30 minutes.

After incubation, the ABRAXANE® nanoparticles were spun and washed three times with 1×PBS to eliminate unbound bevacizumab. The nanoparticles were spun at 5000 rpm for 5 minutes and resuspended in 50 μL of 1×PBS.

100 ng or 500 ng of VEGF was added to each tube for 30 minutes at room temperature, and the washes were repeated to eliminate unbound VEGF. PE anti-human VEGF was added at a 1:50 dilution, and the particles were once again incubated and washed. Visualization was done by flow cytometry, and percentage of PE (VEGF) positive particles was determined (FIGS. 1-4). Various combinations of agents were tested as indicated in the figures. These results demonstrate that ABRAXANE® and bevacizumab spontaneously associate in a manner that preserves VEGF binding potential.

Figure 9:
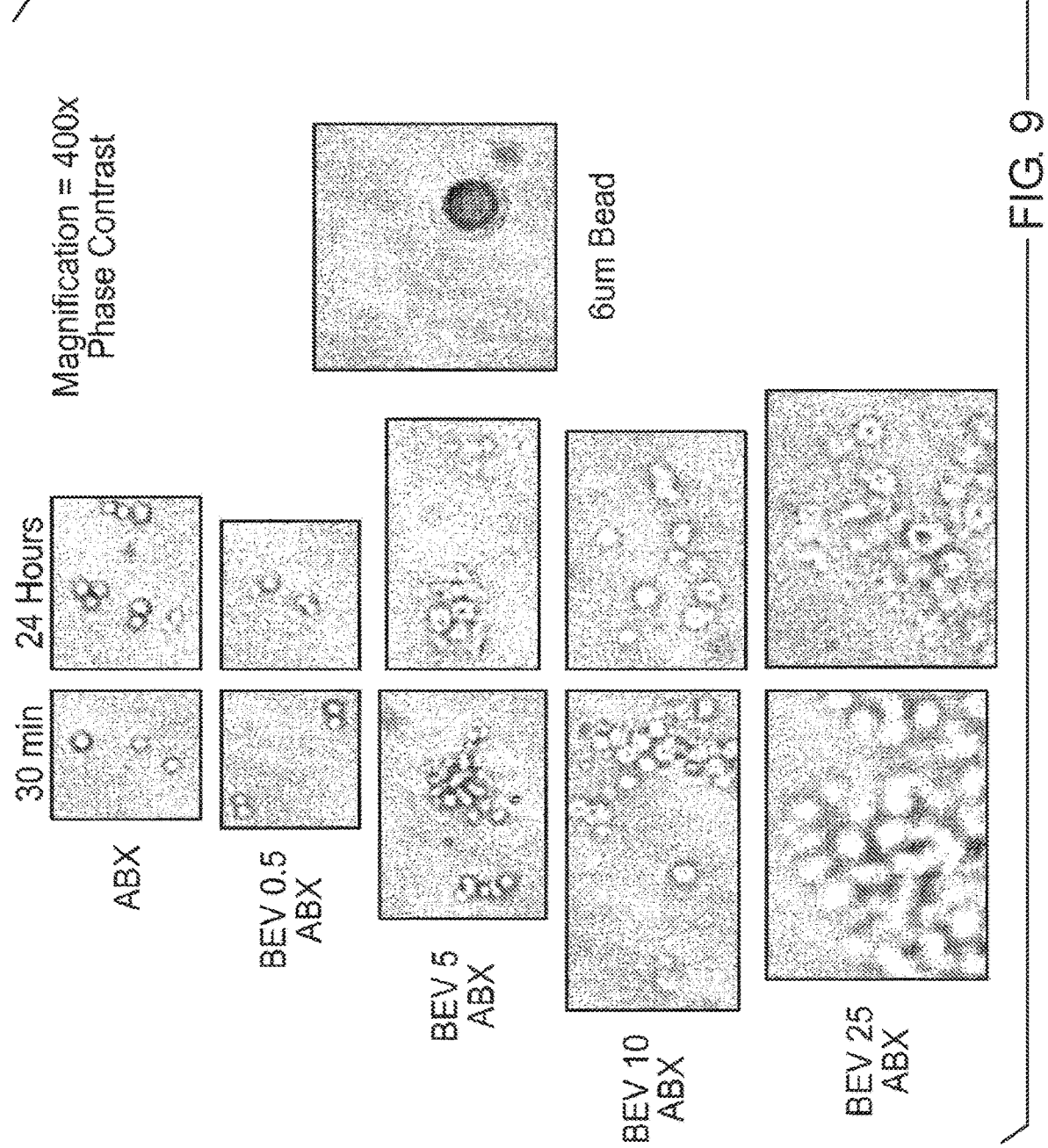
FIG. 9 contains photographs of light microscope images of ABRAXANE® (ABX) or mixtures of ABRAXANE® (ABX) and bevacizumab (BEV; 0.5, 5, 10, or 25 mg/mL) either 4 or 24 hours after mixing.

ABRAXANE® nanoparticles were mixed with varying concentrations of bevacizumab (0.5, 5, 10, and 25 mg/mL). The particles were viewed by light microscopy at 4 and 24 hours after mixing. The macromolecular size of the ABX:BEV complexes was dependent on the concentration of the bevacizumab added and the ABRAXANE® nanoparticles (FIG. 9). Once a maximum size was reached, the ABX:BEV complexes began to break down within about 24 hours (FIG. 9).

Figure 10:
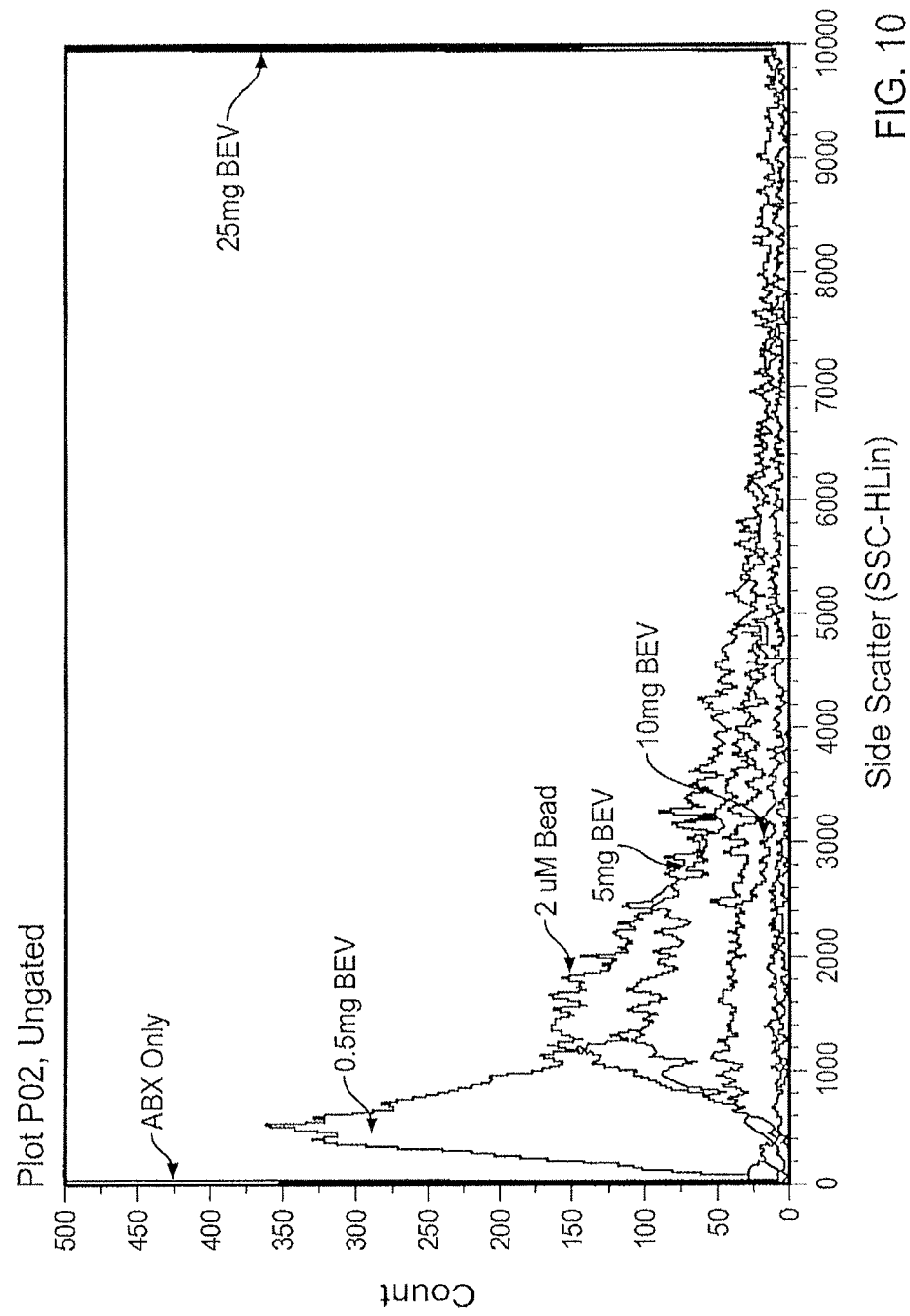
FIG. 10 is a graph plotting flow cytometry results of ABRAXANE® alone, ABX:BEV complexes, and 2 µm standard beads.

Bevacizumab was added to ABRAXANE® nanoparticles in varying concentrations (0.5, 5, 10, 25 mg/mL) and incubated for 30 minutes at room temperature to allow complex formation. ABRAXANE® nanoparticles alone, ABX:BEV complexes, and 2 μm standard beads were visualized by flow cytometry. The complex size increased with increased concentrations of bevacizumab (FIG. 10). The larger the particle-size, the further to the right the peak will be. These results demonstrate that complex size can be manipulated by varying the concentration of bevacizumab added.

In another study, ABRAXANE® nanoparticles and bevacizumab were incubated together for 4 hours and overnight at 1 mg/mL or 10 mg/mL. ABRAXANE® nanoparticles alone were also incubated for 4 hours and overnight as a control. After the allotted time was reached, the complexes were spun down at 7500 RPM for 5 minutes. The supernatants were collected and mixed 1:1 with Laemmli buffer and boiled at 100 degrees for 3 minutes. 20 μL of sample was loaded onto a 7.5% Tris-HCl Criteron gel. A high range molecular weight marker (BioRad) was added for size determination. The gel was run for 3 hours at 75V.

After the gel ran to completion, the gel was placed in a transfer cassette so the proteins could be moved onto a PVDF membrane. The transfer took place overnight at 4° C. running at 20V. The membrane was removed and rocked in TBST containing 5% milk to block for 3 hours at room temperature. The primary antibodies used were Rabbit anti-Taxol (1:500 dilution) and goat anti-mouse IgG-Fab specific-HRP conjugated (1:500 dilution). Antibodies were diluted into 10 mL of TBST with 5% milk. Primary antibodies were allowed to bind overnight at 4° C. while rocking.

Primary antibodies were removed, and the membranes were washed three times for 10 minutes with TBST. The taxol blot was incubated in a1:1000 dilution of secondary anti-rabbit IgG-HRP for 1.5 hours rocking at room temperature. The anti-mouse IgG (Bevacizumab) membrane was incubated in ECL detection reagent (GE Amershem) for 5 minutes before it was exposed to film. Membrane was exposed for 10 seconds, 1 minute, and 5 minutes.

After the incubation in secondary antibody, the taxol blot was washed with TBST for 10 minutes three times. The membrane was then placed in ECL detection reagent for 5 minutes and exposed to film. The exposure times were 1 second, 2 seconds, and 10 seconds.

The IgG blot was specific for the mouse portion of the bevacizumab humanized antibody. A clear concentration dependent increase from complexes mixed at 1 mg/mL to 10 mg/mL was observed (FIG. 15). Taxol is a small molecule around 20 kDa. Free taxol was observed at the bottom of the blot, but it also was observed running at the bevacizumab molecular weight (149 kDa; FIG. 15). These results demonstrate that taxol was bound to the bevacizumab in the supernatant after the large particles were removed by centrifugation.

Figure 17D:
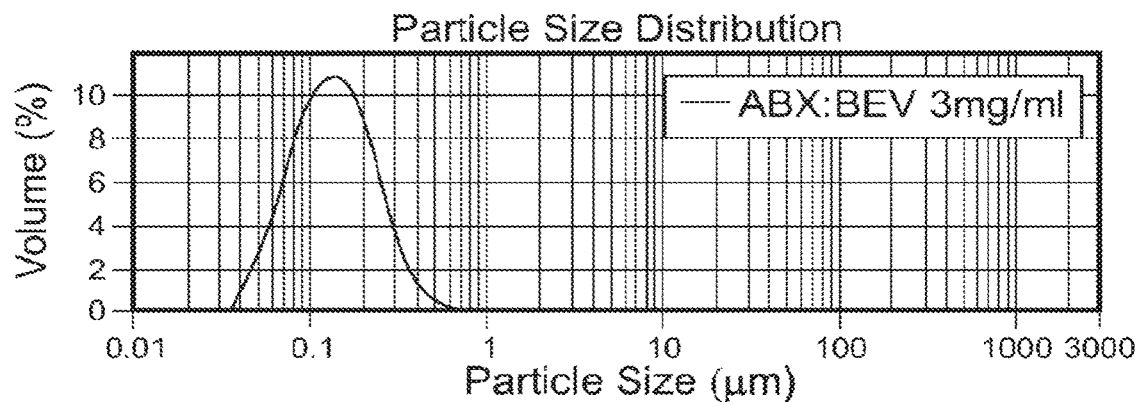
Figure 17E:
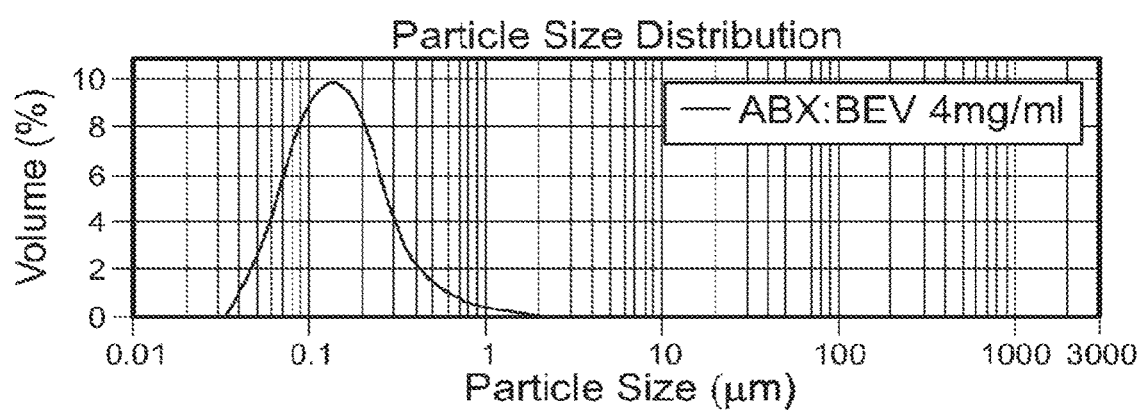
Figure 17F:
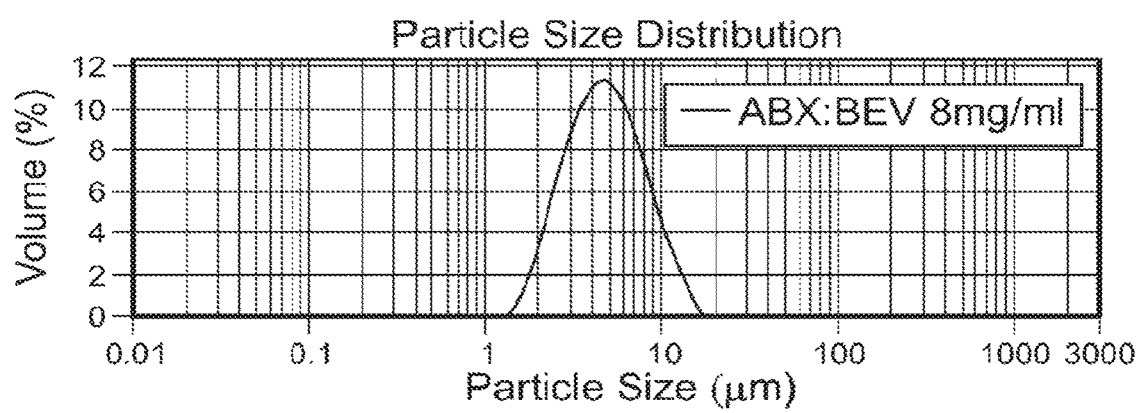

In another study, ABRAXANE® nanoparticles and bevacizumab were incubated for various times (1, 4, and 12 hours), and the particle size distribution of the resulting complexes was determined relative to ABRAXANE® nanoparticles alone using the Malvern Mastersizer 2000E. The size of the complexes generated was a function of antibody concentration and incubation time (FIGS. 16 and 17). In FIGS. 16, 1 and 10 mg/mL of bevacizumab was incubated with ABRAXANE® nanoparticles for 4 hours and overnight. The complexes generated with 10 mg/mL bevacizumab were much larger (8.479 μm) than those with 1 mg/mL bevacizumab (0.165 μm). After an overnight incubation, the larger complexes began to break down.

In FIG. 17, complex size increased with concentration of bevacizumab added when incubated for 1 hour at room temperature. In addition, larger complexes were formed when 1 mg/mL bevacizumab was incubated with ABRAXANE® nanoparticles, spun, and resuspended as compared to the size observed when the same amount (1 mg/mL) of bevacizumab was incubated with ABRAXANE® nanoparticles without spinning the preparation (FIG. 17). These results demonstrate that complex size can be manipulated by altering concentrations, by manual forces (e.g., centrifugation), or by both.

Figure 20A:
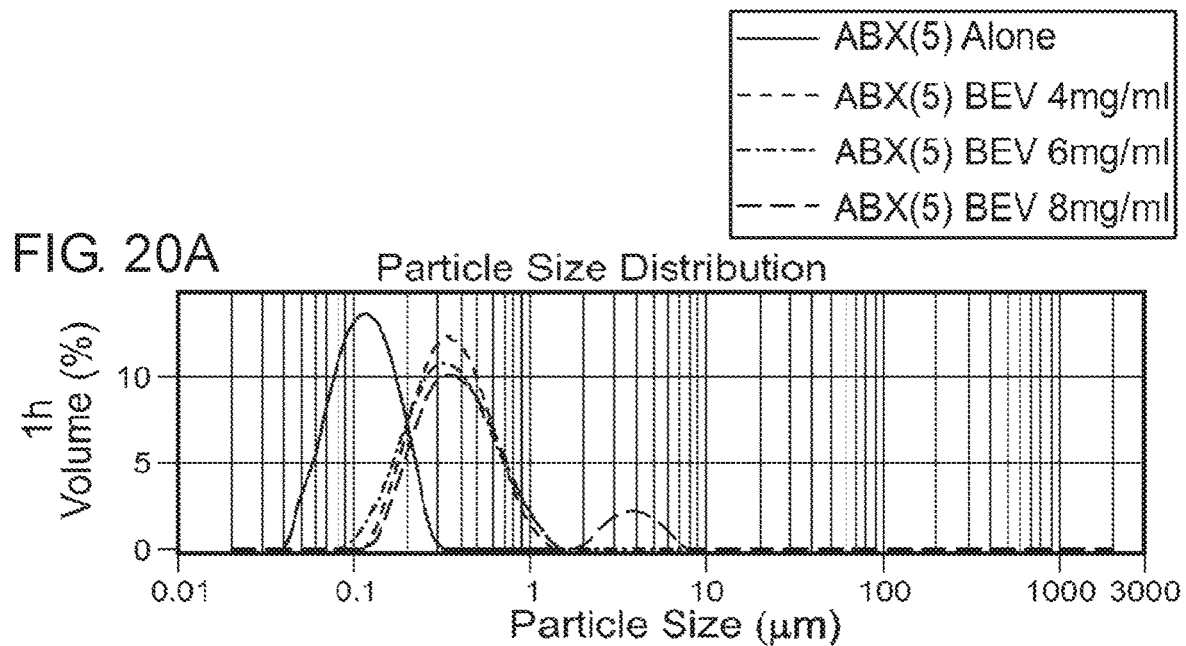
FIGS. 20A-C contain graphs plotting the particle size distribution for ABX:BEV complexes as determined using a Mastersizer 2000E (Malvern Instruments Ltd., Worcestershire, England). ABX (20 mg/mL) and BEV (16, 24, or 32 mg/mL) were incubated for 1, 2, or 4 hours at room temperature. After incubation, the mixtures were diluted 1:4 for a final concentration of ABX (5 mg/mL) and BEV (4, 6, or 8 mg/mL), and the diluted samples analyzed using a Mastersizer 2000E.
Figure 20B:
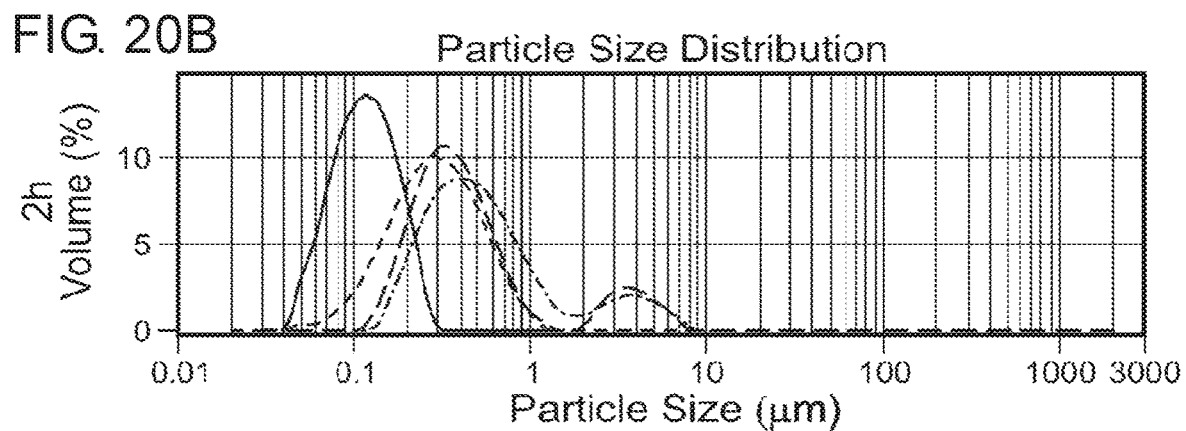
Figure 20C:
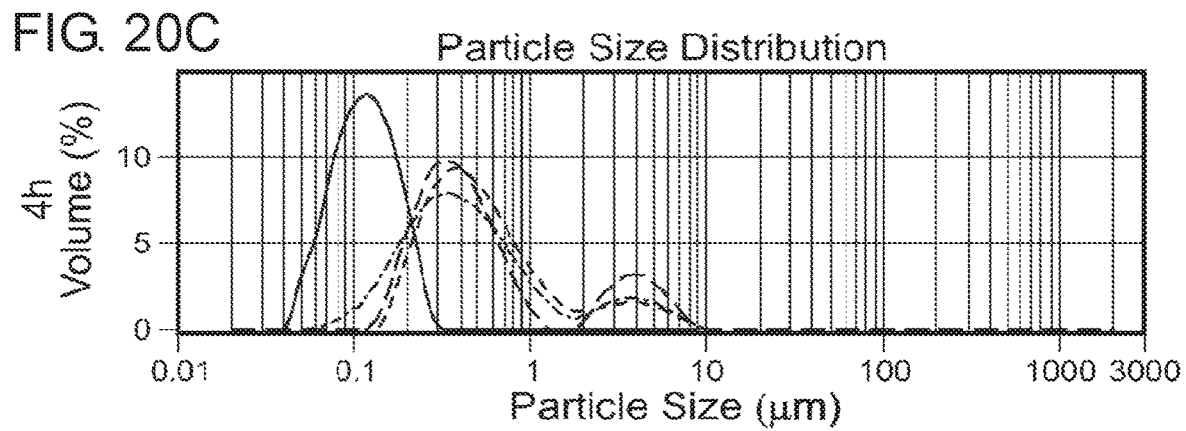
Figure 22A:
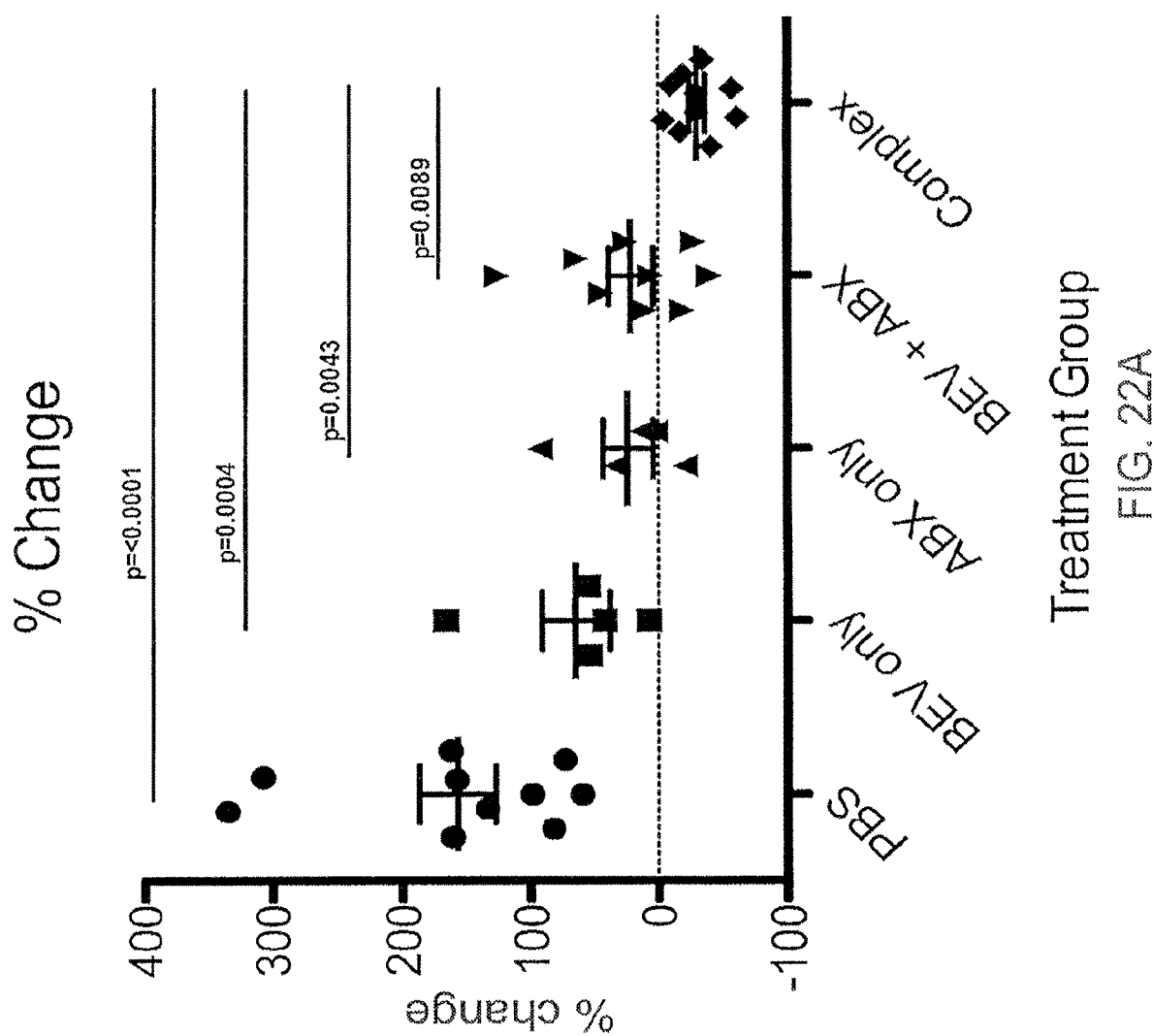
FIGS. 22A-C contain graphs plotting percent change (A), tumor size (B), and survival (C) for Group 1 mice treated with PBS, Bevacizumab (8 mg/kg), ABRAXANE® (30 mg/kg), Bevacizumb (day 0, 8 mg/kg) followed by ABRAXANE® (day 1, 30 mg/kg), or small nanoAB (complex).
Figure 22B:
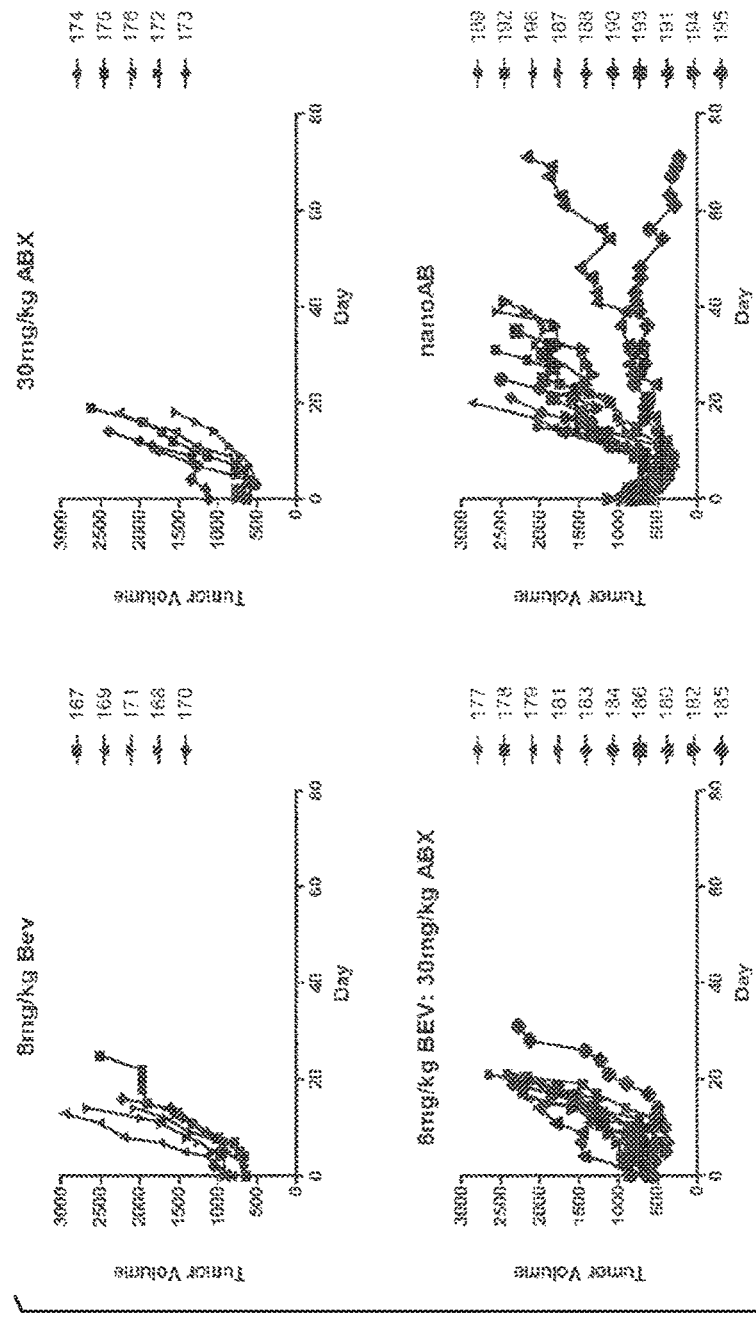
Figure 22C:
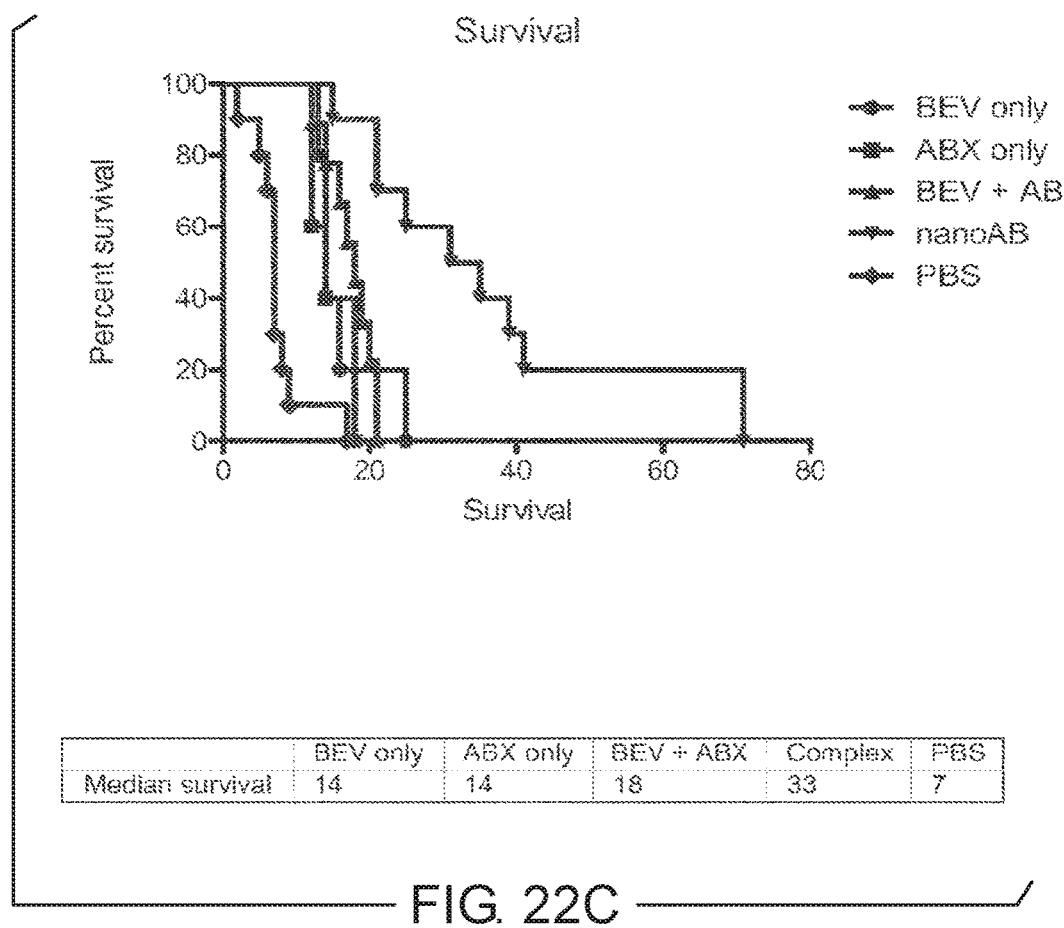

In another study, ABRAXANE® nanoparticles were dissolved at a concentration of 20 mg/mL, and bevacizumab was added at a final concentration of 16, 24, or 32 mg/mL. The mixtures were incubated at room temperature for various times (1, 2, and 4 hours). After this incubation, the mixture was diluted 1:4 (final concentration of ABRAXANE=5 mg/mL; final concentrations of bevacizumab=4, 6, or 8 mg/mL). The particle size distribution of the resulting complexes was determined relative to ABRAXANE® nanoparticles alone using the Malvern Mastersizer 2000E. The size of the complexes generated was a function of antibody concentration and incubation time (FIG. 20).

In another study, 10 mg of ABRAXANE® nanoparticles was reconstituted in 1 mL of bevacizumab at 0, 2, 4, 6, 8, 10, 15, or 25 mg/mL, and the mixture was incubated for 1 hour at room temperature. The particle size distribution of the resulting complexes was determined by light-refraction of unlabeled complexes (Table 2). The size of the complexes generated was a function of antibody concentration (Table 2).

TABLE 2

| ABX (mg/mL) | BEV (mg/mL) | d (0.1) μm | d (0.5) μm | d (0.9) μm |
|---|---|---|---|---|
| 10 | 0 | 0.125 | 0.146 | 0.174 |
| 10 | 2 | 0.122 | 0.157 | 0.196 |
| 10 | 4 | 0.138 | 0.159 | 0.182 |
| 10 | 6 | 0.124 | 0.174 | 0.235 |
| 10 | 8 | 0.171 | 0.226 | 0.278 |

TABLE 2-continued

| ABX (mg/mL) | BEV (mg/mL) | d (0.1) µm | d (0.5) µm | d (0.9) µm |
|---|---|---|---|---|
| 10 | 10 | 0.516 | 0.577 | 0.67 |
| 10 | 15 | 0.981 | 1.129 | 1.31 |
| 10 | 25 | 1.036 | 2.166 | 3.233 |

ABRAXANE® and bevacizmab were mixed and incubated for 30 minutes at room temperature to allow complex formation. Mice were injected with 100 µL of the complexes containing 5 mg of ABRAXANE® and 1 mg of bevacizumab in the dorsal tail vein. Injection of the complexes did not harm any mice.

Example 2—Human Plasma Inhibits the Formation of ABRAXANE®/AVASTIN® Complexes

10 µL (10 g) of ABRAXANE® was added to eppendorf tubes, and 500 µg (25 ALL) of AVASTIN was added and resuspended in a final volume of 50 µL. Human plasma was titrated using 1:2 dilutions (1:2, 1:4, 1:8, or 1:16). 50 µL of plasma and 50 µL of each plasma titration were added to the tubes with ABRAXANE® and AVASTIN. In some cases, human serum albumin (500 µg, 50 µg, 5 µg, 0.5 µg, or 0.05 µg/mL) or human polyclonal immunoglobulin (500 µg, 50 µg, 5 µg, 0.5 µg, and 0.05 µg/mL) was added to the tubes in place of human plasma.

After a 30 minute incubation at room temperature, the ABRAXANE® nanoparticles were washed in 1×PBS twice. 100 ng of VEGF was added to each tube for 30 minutes at room temperature, and the washes were repeated. PE anti-human VEGF was added at a 1:50 dilution, and particles were once again incubated and washed. Visualization was done by flow cytometry, and percentage of PE (VEGF) positive particles was determined (FIG. 5-8).

Figure 11:
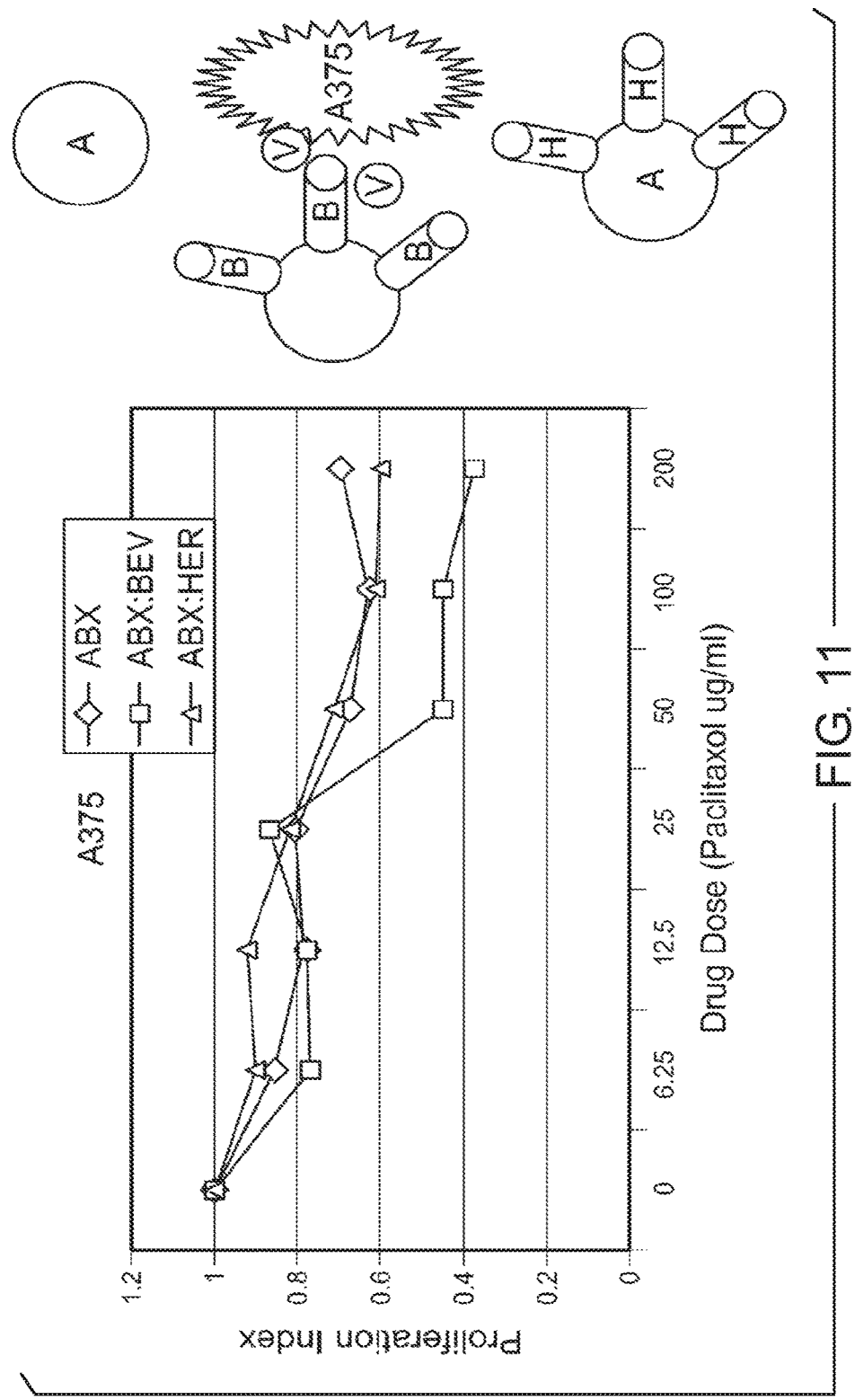
FIG. 11 is graph plotting the proliferation index for A375 cells (a melanoma tumor cell line) exposed to ABRAXANE® (ABX) only, ABRAXANE®:Herceptin (non-VEGF targeting) complexes, or ABRAXANE®:Bevacizumab (VEGF targeting) complexes at the indicated dose.

Example 3—ABRAXANE®/AVASTIN® Complexes have a Higher Level of Cell Toxicity than ABRAXANE® Alone or ABRAXANE®/Herceptin Complexes The VEGF producing melanoma tumor cell line, A375, was incubated overnight in the presence of ABRAXANE® nanoparticles only, ABRAXANE®/Herceptin (non-VEGF targeting) complexes, and ABRAXANE®/AVASTIN® (ABX:BEV; VEGF targeting) complexes. Increasing doses of drug were added to the cells to give 6.25, 12.5, 25, 50, 100, and 200 µg/mL of taxol. After the overnight incubation, cell proliferation was determined by measuring the level of DNA synthesis. A higher level of cell toxicity (less DNA synthesis) of cells incubated with the VEGF targeting complexes (ABX:BEV) relative the ABX alone and non-VEGF targeted complexes (ABX:HER) (FIG. 11).

Example 4—Stability of ABRAXANE®/AVASTIN® Complexes

ABRAXANE®/AVASTIN® complexes were fluorescently labeled such that both the albumin of the ABRAXANE® and the bevacizumab were directly labeled with a fluorescent marker. The complexes were visualized by flow cytometry after 0, 1, 2, 3, 4, 24, and 48 hours in 0.9% saline at room temperature and after 0, 15, 30, 60, and 120 minutes in human plasma at 37° C. The complexes were stable in saline at room temperature with only about 10% loss at 24 hours (FIG. 12). In human plasma at 37° C., the complexes began to break down in about 15 minutes and were completely undetectable by 120 minutes.

Example 5—ABRAXANE®/Cisplatin Complexes

Figure 13A:
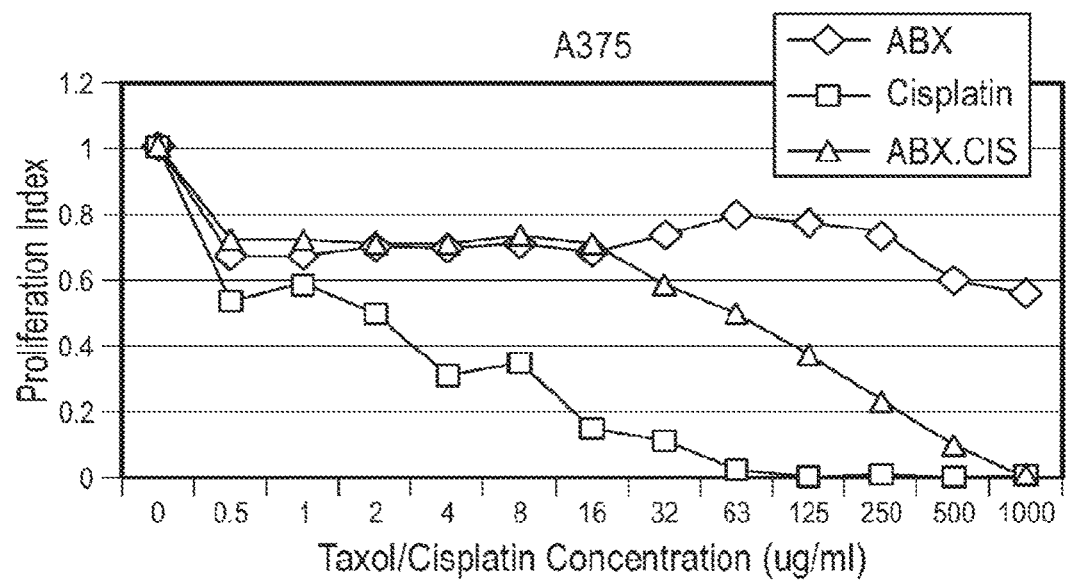
FIG. 13A contains a line graph plotting the proliferation index for A375 cells exposed to ABRAXANE® (ABX) only, cisplatin only, or ABRAXANE®:cisplatin complexes at the indicated dose and contains a bar graph plotting demonstrating that 30% of cisplatin (CDDP) remained unbound after ABX:cisplatin were mixed and incubated for 30 minutes.
Figure 13B:
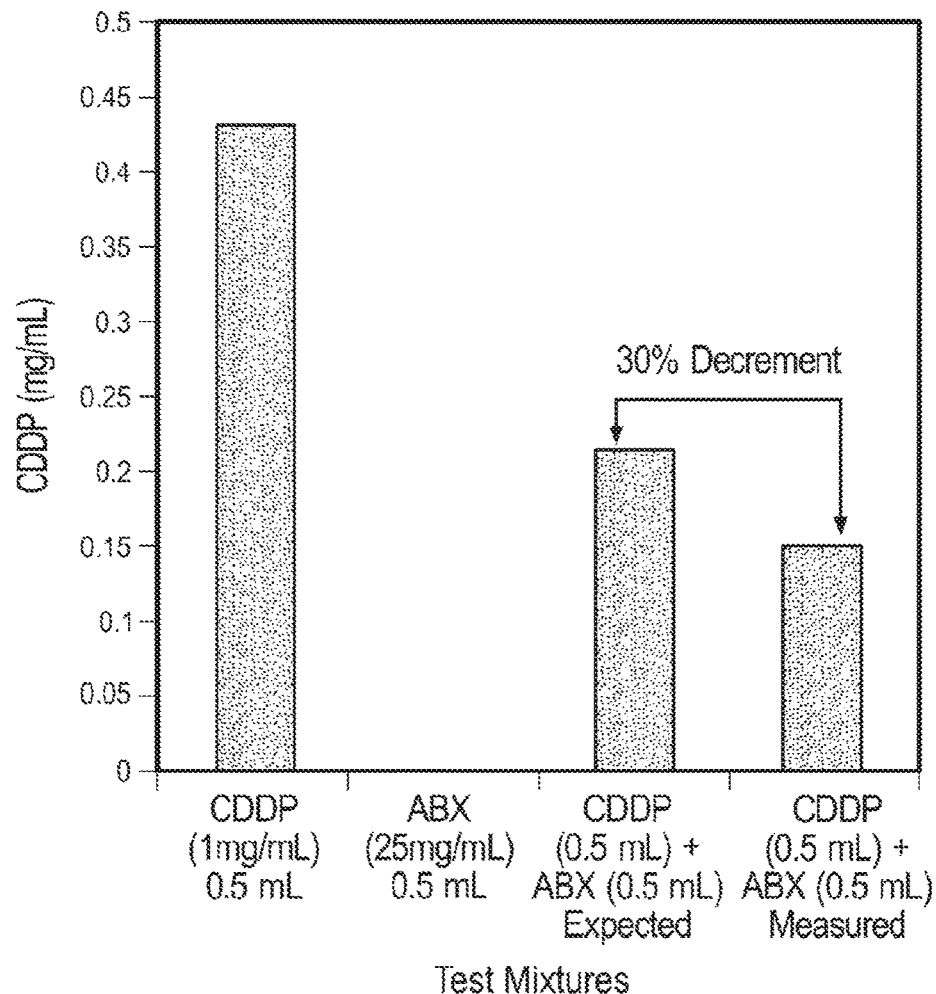
FIG. 13B depicts the amount of cisplatin remaining in suspension after the 30 minute incubation with the ABX nanoparticles was only about 30% of the original concentration FIGS. 14 A-J contains scatter plots of a flow cytometry analysis of the indicated complexes containing ABRAXANE®.

ABRAXANE® nanoparticles were incubated with cisplatin (cisplatinum or cis-diamminedichloroplatinum(II) (CDDP)) for 30 minutes at 37° C. The particles were spun, and the supernatant was tested by HPLC to determine how much free cisplatin was in suspension. Cisplatin spontaneously bound to the ABRAXANE® nanoparticles, and the amount remaining in suspension after the 30 minute incubation with the ABRAXANE® nanoparticles was only about 30% of the original concentration (FIG. 13). These results demonstrate that about 70% of the cisplatin bound to the ABRAXANE® nanoparticles.

In another experiment, ABRAXANE®/cisplatin complexes were generated as described above and added to A375 tumor cells. After an overnight incubation, proliferation of the cells was measured by determining the level of DNA synthesis. The toxicity of the ABRAXANE®/cisplatin complexes was measured relative to the two drugs individually. The ABRAXANE®/cisplatin complexes were more toxic to cells (lower level of DNA synthesis) than ABRAXANE® alone but less toxic than cisplatin alone (FIG. 13). These results demonstrate that cisplatin can be bound to ABRAXANE® nanoparticles and delivered to tumors without the highly toxic side effects of cisplatin alone.

Example 6—ABRAXANE®/Antibody Complexes

Three therapeutic monoclonal antibodies (bevacizumab, trastuzamab, and rituxan) were fluorescently labeled and incubated with fluorescently labeled ABRAXANE® nanoparticles. The particles were spun down, washed, and visualized by flow cytometry. All three of these recombinant therapeutic antibodies spontaneously formed complexes with ABRAXANE® nanoparticles (FIG. 14). These results demonstrate that albumin-containing nanoparticles can be used to form larger complexes not only with bevacizumab antibodies but also with other antibodies such as trastuzamab and rituxan.

Taken together, the results provided herein demonstrate that in vitro mixing of albumin-containing nanoparticles (e.g., ABRAXANE® nanoparticles) and antibodies (e.g., bevacizumab, trastuzamab, or rituxan) leads to macromolecular complex formation, the characteristics of which (e.g., size, antibody content, or chemotherapeutic drug content) can be customized depending on need. These results also demonstrate that the macromolecular complexes retain antibody mediated target binding specificity, retain or exhibit enhanced chemotherapeutic tumor cell cytotoxicity, and exhibit no additional toxicity beyond that of ABRAXANE® nanoparticles alone.

Example 7—ABRAXANE®/AVASTIN® Complexes Disassociate in Serum

The following was performed to determine what happens to ABRAXANE®/AVASTIN® complexes in serum over time. 6 mg or 8 mg of AVASTIN® were bound to ABRAXANE® for 30 minutes at room temperature. The complexes were incubated with serum for 15, 30, 45, or 60 minutes. After this incubation, the serum/complex solution was spun down at 10,000 rpm for 10 minutes at 4° C. The supernatants were collected, separated using gel electrophoresis, and analyzed via Western blotting with an anti-paclitaxel antibody and an HRP-conjugated secondary antibody.

Figure 18:
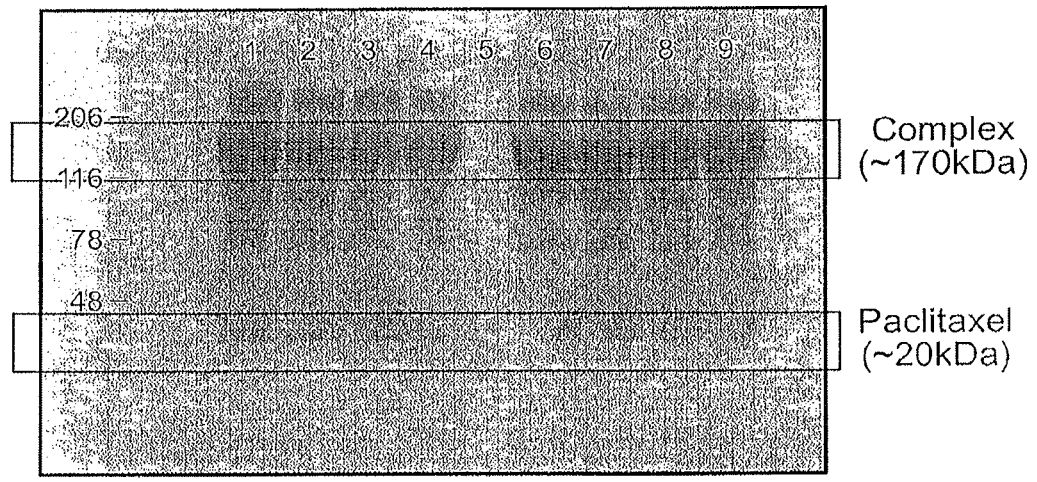
FIG. 18 is a photograph of a Western blot analysis of ABX:BEV complexes exposed to serum for 15, 30, 45, or 60 minutes. The ABX:BEV complexes were formed by incubating either 6 mg or 8 mg of BEV with ABX for 30 minutes at room temperature. The primary antibody used for the Western blot was an anti-paclitaxel antibody. Lane 1: ABX:BEV (6 mg) exposed to serum for 15 minutes; Lane 2: ABX:BEV (6 mg) exposed to serum for 30 minutes; Lane 3: ABX:BEV (6 mg) exposed to serum for 45 minutes; Lane 4: ABX:BEV (6 mg) exposed to serum for 60 minutes; Lane 5: blank; Lane 6: ABX:BEV (8 mg) exposed to serum for 15 minutes; Lane 7: ABX:BEV (8 mg) exposed to serum for 30 minutes; Lane 8: ABX:BEV (8 mg) exposed to serum for 45 minutes; Lane 9: ABX:BEV (8 mg) exposed to serum for 60 minutes.

Incubation in the presence of serum resulted in complex disassociation, not disintegration (FIG. 18).

In another experiment, ABRAXANE®/AVASTIN® complexes (in saline or plasma) appeared to dissociate primarily into ABX/BEV complexes (FIG. 21). Results appeared to suggest that the ABRAXANE®/AVASTIN® association is mediated via albumin binding to the Fc fragment of AVASTIN®.

Example 8—Bevacizumab does not Bind Free Paclitaxel

The following was performed to determine if bevacizumab binds free paclitaxel. 4 mg of bevacizumab was incubated with paclitaxel (0.1, 0.5, 1, or 2 mg) for 30 minutes at room temperature. After this incubation, the mixtures were separated using gel electrophoresis and analyzed via Western blotting with an anti-paclitaxel antibody and an HRP-conjugated secondary antibody.

Figure 19:
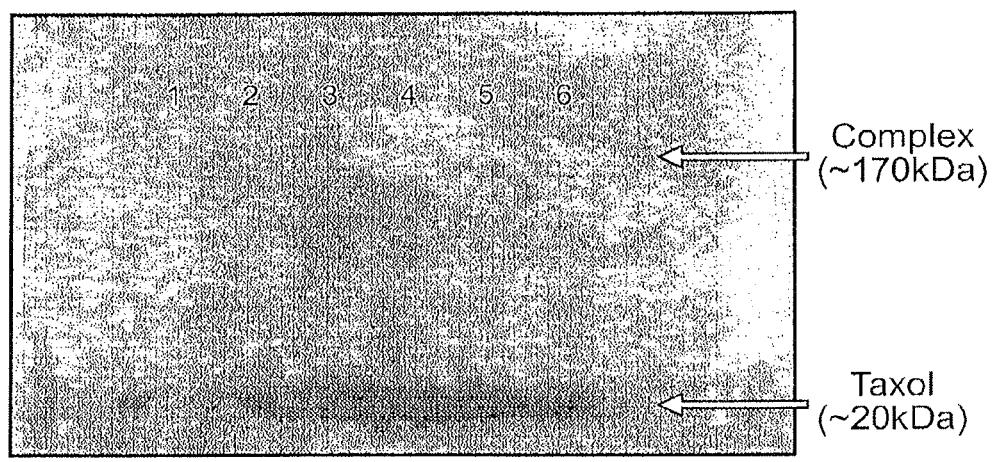
FIG. 19 is a photograph of a Western blot analysis of mixtures of paclitaxel (0.1, 0.5, 1, or 2 mg) and BEV (4 mg) incubated together for 30 minutes at room temperature. The primary antibody used for the Western blot was an anti-paclitaxel antibody. Lane 1: Bev (4 mg); Lane 2: Taxol (2 mg); Lane 3: Taxol (2 mg)+Bev (4 mg); Lane 4: Taxol (1 mg)+Bev (4 mg); Lane 5: Taxol (0.5 mg)+Bev (4 mg); Lane 6: Taxol (0.1 mg)+Bev (4 mg).

Bevacizumab did not bind free paclitaxel (FIG. 19).

Example 9—ABRAXANE®/AVASTIN® Complexes Inhibit Tumor Growth More Effectively than ABRAXANE® Alone. AVASTIN® Alone, and the Sequential Use of ABRAXANE® and AVASTIN®

Female athymic nude mice were injected with $1\times10^6$ A375 melanoma cells. Tumors were allowed to grow, and treatments were administered when tumors were between 600 and 1000 mm$^3$. Mice were treated with (a) 100 µL PBS, (b) Bevacizumab (8 mg/kg for Group I and II; 24 mg/kg for Group III), (c) ABRAXANE® (30 mg/kg), (d) Bevacizumb (day 0, 8 mg/kg for Group I and II; 24 mg/kg for Group III) followed by ABRAXANE® (day 1, 30 mg/kg), (e) small nanoAB (Group I, II, and III), or (f) big nanoAB (Group III). Mice were treated one time for Groups I and III and two times (day 0 and day 7) for Group II. Tumor size was monitored 2-3 times per week. Mice were sacrificed when tumors reached 2000-2500 mm$^3$. Percent change from baseline was calculated by [(tumor size on day 7 (Group I and III) or day 21 (Group II)–tumor size on day of treatment)/tumor size on day of treatment]*100.

Small nanoAB (also nanoAB or Complex in Group I and II when only one size nanoparticle was tested) was produced as follows. 10 mg ABRAXANE® was reconstituted in 3.6 mg of Bevacizumab in 500 µL 0.9% saline and incubated for 1 hour at room temperature. After incubation, nanoAB was brought to 1 mL with 0.9% saline. NanoAB was further diluted, and 100 µL was administered to mice for an 8 mg/kg bevacizumab and 30 mg/kg ABRAXANE® dose. Average particle size for small nanoAB was 0.149 µm.

Big nanoAB was produced as follows. 10 mg ABRAXANE® was reconstituted in 8 mg of Bevacizumab in 500 µL 0.9% saline and incubated for 1 hour at room temperature. After incubation, big nanoAB was brought to 1 mL with 0.9% saline. Big nanoAB was further diluted, and 100 µL was administered to mice for a 24 mg/kg bevacizumab and 30 mg/kg ABRAXANE® dose. Average particle size for big nanoAB was 0.226 µm.

Figure 23A:
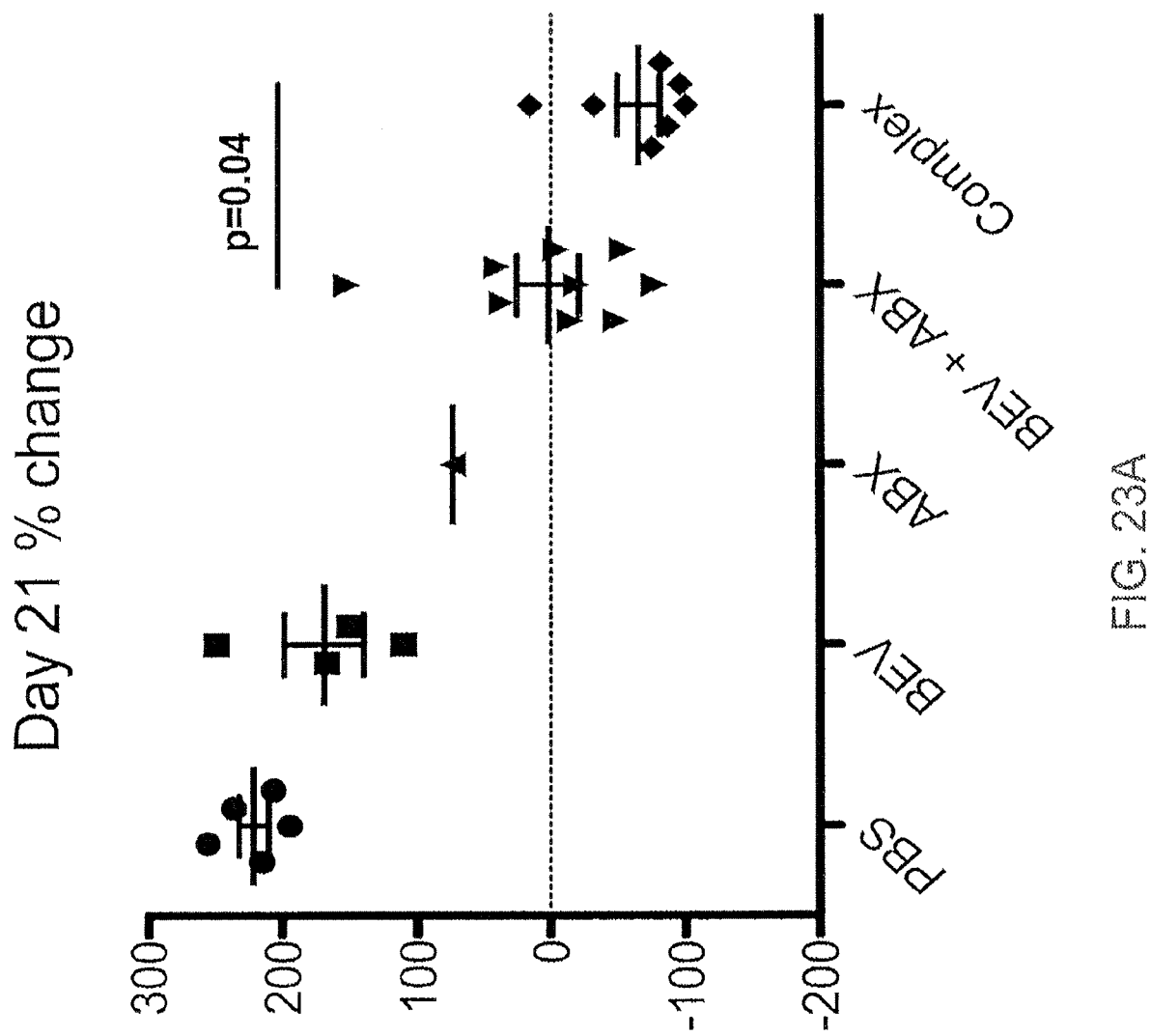
Figure 23B:
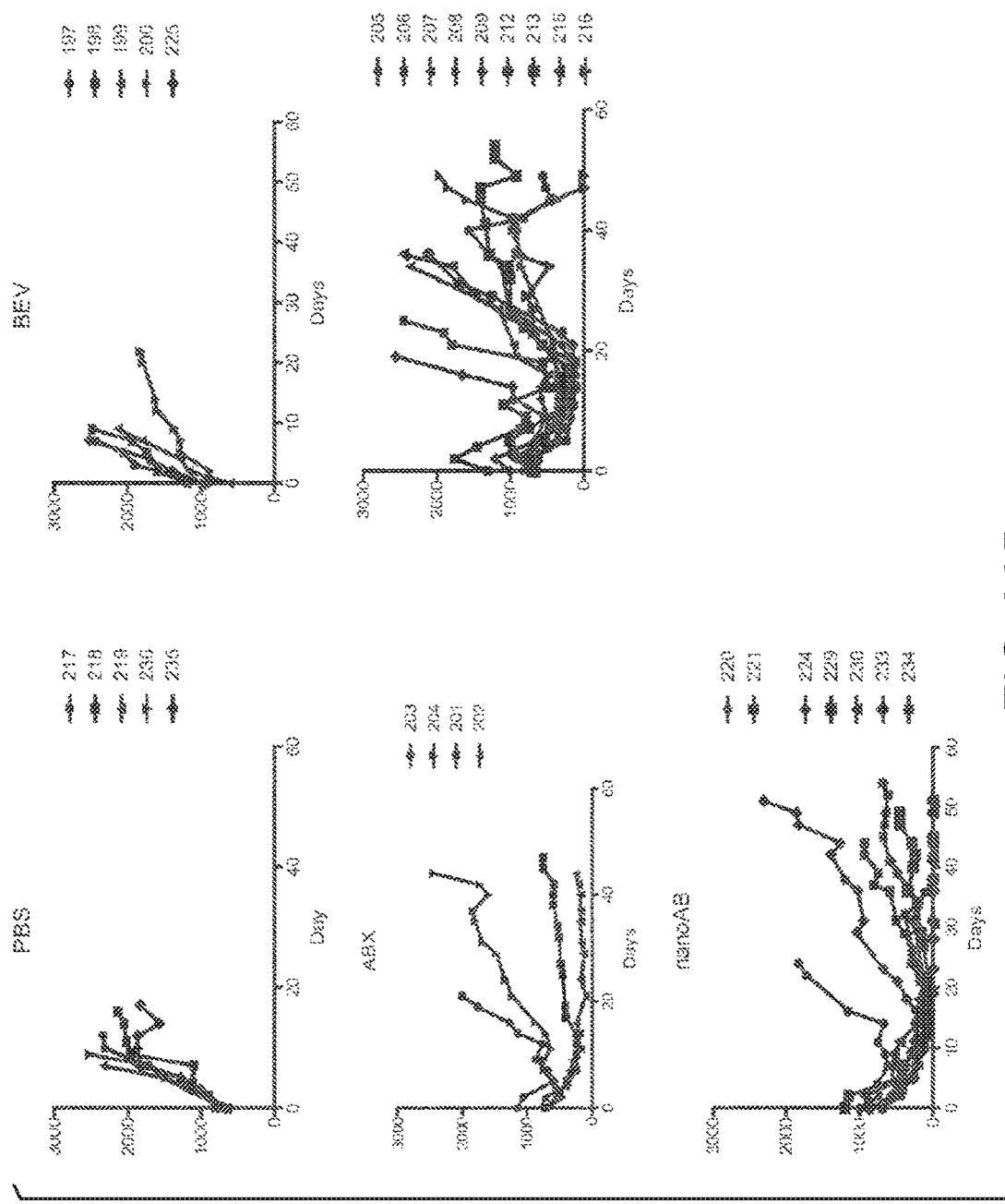
Figure 24A:
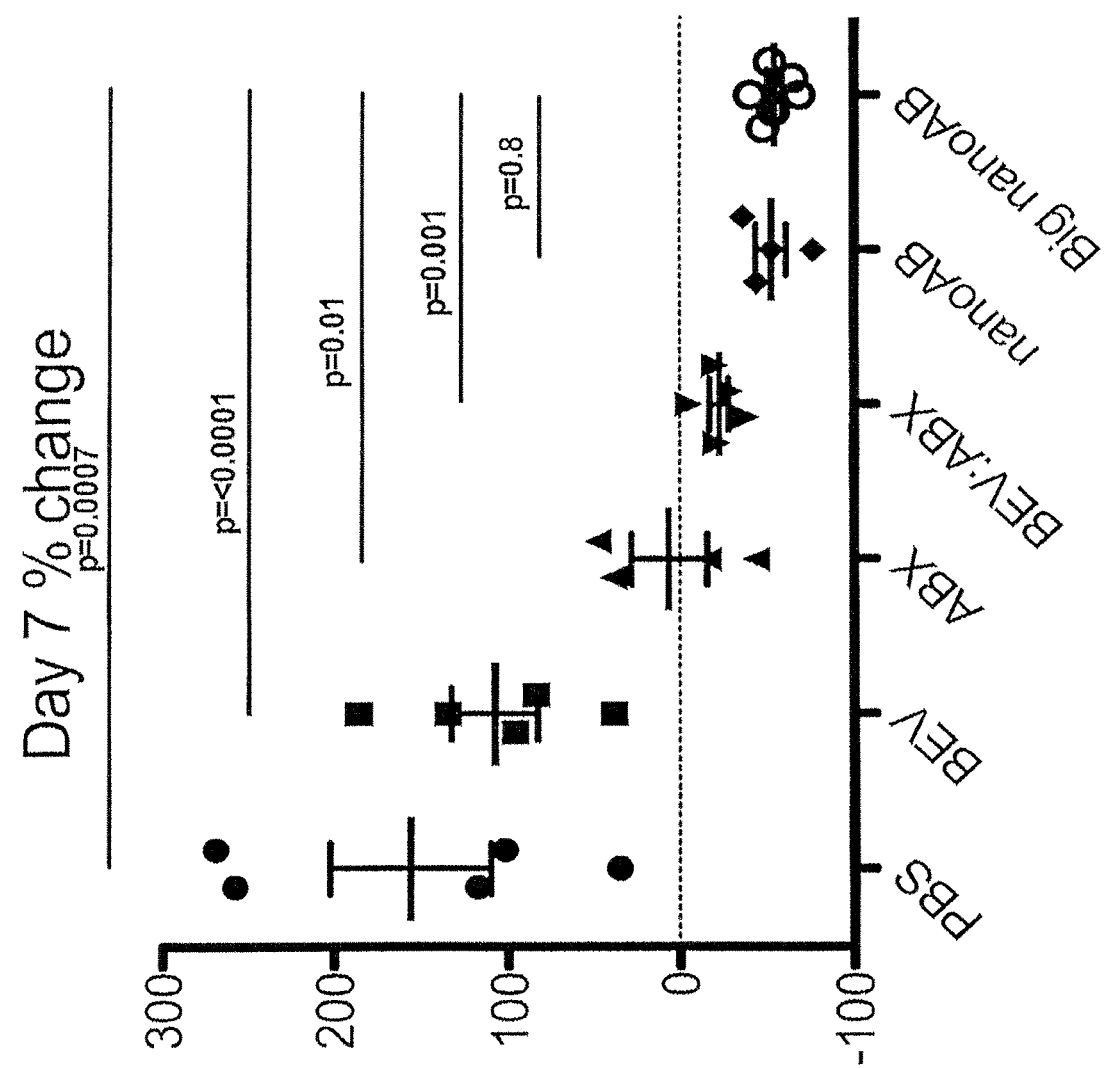
Figure 24B:
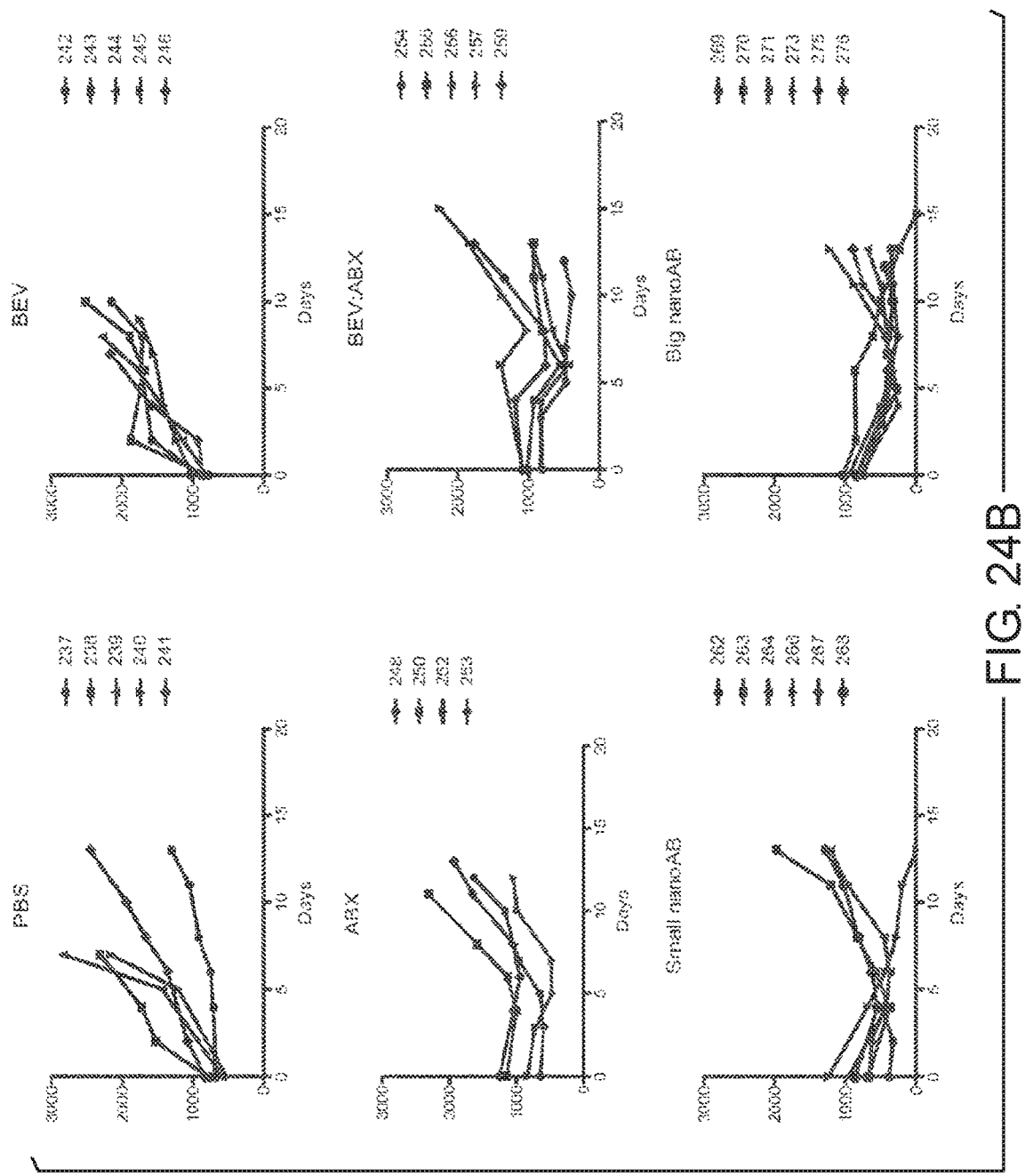

Anti-tumor outcomes were statistically superior in mice treated with nanoAB (small and big nanoAB) from the standpoint of tumor volume reduction and survival (FIGS. 23A-C for Group I, 24A-C for Group II, and 25A-C for Group II). In addition, histologic (formalin fixed paraffin embedded) analysis of necropsied organs in mice receiving nanoAB therapy did not reveal any unusual toxicities.

In another experiment, female athymic nude mice were injected with $1\times10^6$ A375 melanoma cells. Tumors were allowed to grow, and treatments were administered when tumors were between 600 and 1000 mm$^3$. Mice were treated intravenously with (a) 100 µL PBS, (b) Bevacizumab (24 mg/kg) only, (c) ABRAXANE® (30 mg/kg) only, (d) Bevacizumb (24 mg/kg) followed the next day by ABRAXANE® (30 mg/kg) (BEV+ABX), (e) ABRAXANE® (30 mg/kg) followed the next day by Bevacizumb (24 mg/kg) (ABX+BEV), or (f) ABRAXANE®/AVASTIN® complexes with an average diameter of about 0.225 µm, in which ABRAXANE® (10 mg/mL) was premixed with Bevacizumb (8 mg/mL) and incubated for 30 minutes before injection (big nanoAB). The percent change is tumor size at seven days was calculated as follows: [(size on day 7–size on day of treatment)/size on day of treatment]*100. In addition, mice were sacrificed when tumors were 2500 mm$^3$ or at 60 days if tumor size never reached 2500 mm.

Figure 28:
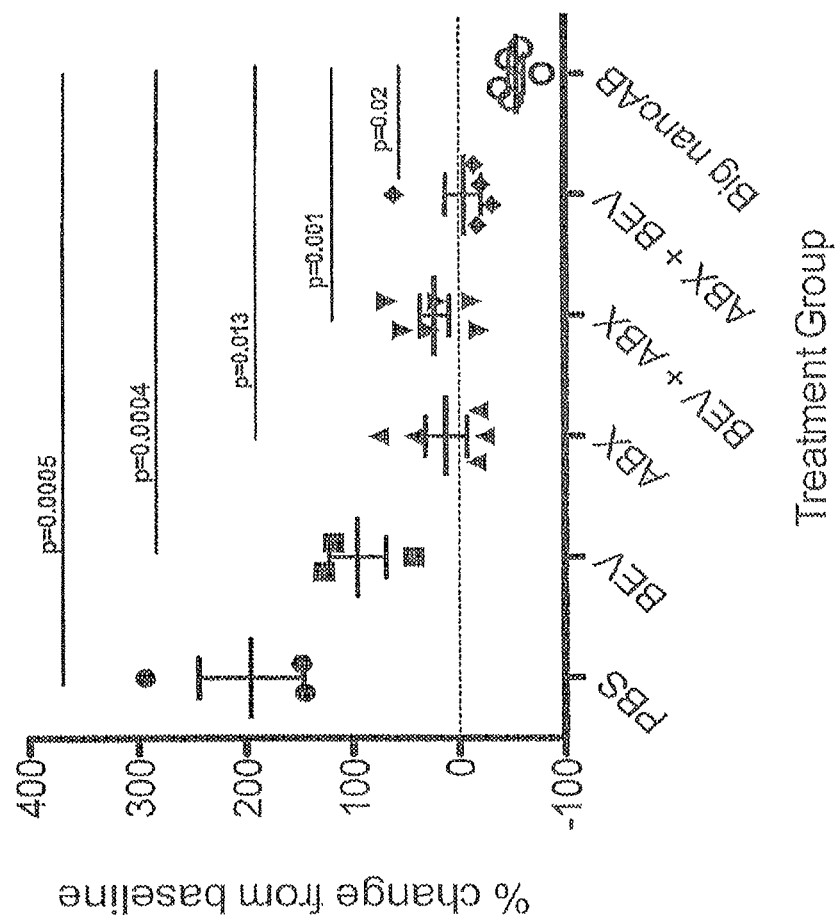
FIG. 28 is a graph plotting percent change at seven days in tumor size from baseline of A375 tumor bearing nude mice treated with PBS, Bevacizumab (24 mg/kg) only, ABRAXANE® (30 mg/kg) only, Bevacizumb (24 mg/kg) followed the next day by ABRAXANE® (30 mg/kg) (BEV+ABX), ABRAXANE® (30 mg/kg) followed the next day by Bevacizumb (24 mg/kg) (ABX+BEV), and big nanoAB complexes (0.225 µm; big nanoAB), in which ABRAXANE® (10 mg/mL) was premixed with 8 mg/mL Bevacizumb and incubated for 30 minutes before injection.
Figure 29:
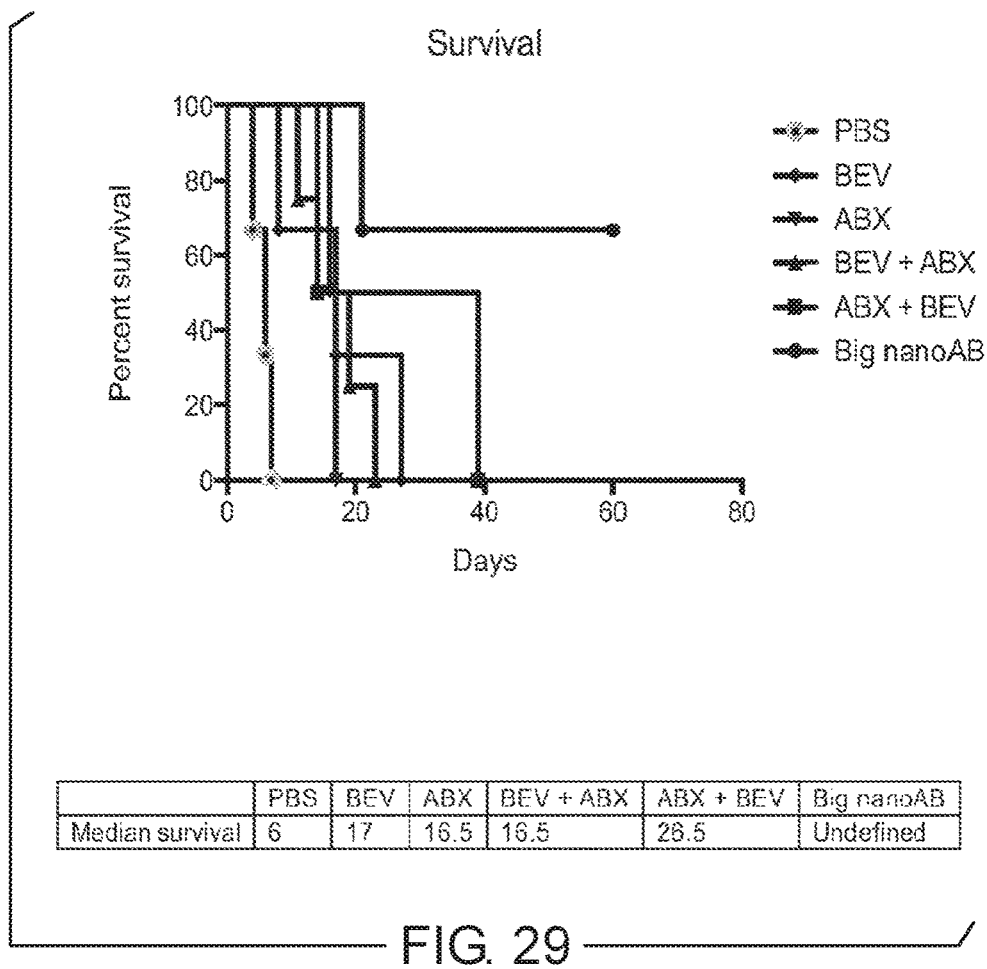
FIG. 29 is a Kaplan Meier graph plotting survival of A375 tumor bearing nude mice treated with PBS, Bevacizumab (24 mg/kg) only, ABRAXANE® (30 mg/kg) only, Bevacizumb (24 mg/kg) followed the next day by ABRAXANE® (30 mg/kg) (BEV+ABX), ABRAXANE® (30 mg/kg) followed the next day by Bevacizumb (24 mg/kg) (ABX+BEV), and big nanoAB complexes (0.225 µm; big nanoAB), in which ABRAXANE® (10 mg/mL) was premixed with 8 mg/mL Bevacizumb and incubated for 30 minutes before injection.

No significant difference was observed between the BEV+ABX and ABX+BEV groups (FIGS. 28-29). These results suggest that the order of drug administration does not impact tumor response seven days after treatment. The mice treated with ABRAXANE®/AVASTIN® complexes, however, exhibited significant differences as compared to the other treatment arms with profound tumor response in all mice at day 7 after treatment (FIGS. 28-29). These results demonstrate that ABRAXANE®/AVASTIN® complexes with an average diameter between about 0.15 µm and about 0.3 µm can be used successfully to reduce the number of cancer cells within a mammal.

In another experiment, female athymic nude mice were injected with $1\times10^6$ A375 melanoma cells. Tumors were allowed to grow, and treatments were administered when tumors were between 600 and 1000 mm$^3$. Mice were treated intravenously with (a) 100 µL PBS, (b) Bevacizumab (45 mg/kg) only, (c) ABRAXANE® (30 mg/kg) only, (d) Bevacizumb (45 mg/kg) followed the next day by ABRAXANE® (30 mg/kg) (BEV+ABX), (e) ABRAXANE® (30 mg/kg) followed the next day by Bevacizumb (45 mg/kg) (ABX+BEV), or (f) ABRAXANE®/AVASTIN® complexes with an average diameter of about 0.160 µm (nanoAB 160), 0.225 µm (nanoAB 225), 0.560 µm (nanoAB 560), or 1.130 µm (nanoAB 1130). The nanoAB 160 complexes were prepared by incubating 10 mg of ABRAXANE® in 4 mg/mL of AVASTIN®; the nanoAB 225 complexes were prepared by incubating 10 mg of ABRAXANE® in 8 mg/mL of AVASTIN®; the nanoAB 560 complexes were prepared by incubating 10 mg of ABRAXANE® in 10 mg/mL of AVASTIN®; and the nanoAB 1130 complexes were prepared by incubating 10 mg of ABRAXANE® in 15 mg/mL of AVASTIN®. The mixtures incubated for 60 minutes at room temperature and diluted prior to injection. The percent change is tumor size at seven days was calculated as follows: [(size on day 7–size on day of treatment)/size on day of treatment]*100. In addition, mice were sacrificed when tumors were 2500 mm$^3$ or at 60 days if tumor size never reached 2500 mm$^3$.

Figure 30:
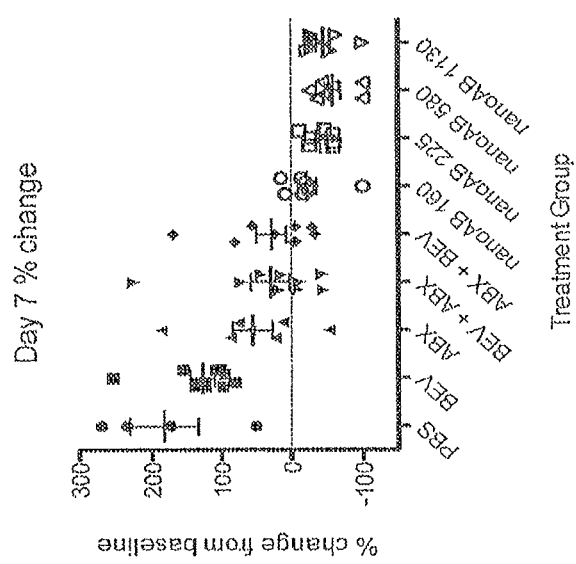
FIG. 30 is a graph plotting percent change at seven days in tumor size from baseline of A375 tumor bearing nude mice treated intravenously with PBS, Bevacizumab (45 mg/kg) only, ABRAXANE® (30 mg/kg) only, Bevacizumb (45 mg/kg) followed the next day by ABRAXANE® (30 mg/kg) (BEV+ABX), ABRAXANE® (30 mg/kg) followed the next day by Bevacizumb (45 mg/kg) (ABX+BEV), and nanoAB complexes of increasing sizes (0.16 µm, 0.225 µm, 0.58 µm, and 1.13 µm).

On day 7 post treatment, the mice treated with nanoAB 225, 560, or 1130 exhibited tumors with significantly smaller tumor size as compared to all the other treatment groups (FIG. 30). The nanoAB 160 treatment group was significantly different than the PBS, BEV only, and ABX only groups, but not statistically different from the sequential administration groups, BEV+ABX and ABX+BEV. There were no significant differences between the different nanoAB groups, although the nanoAB 1130 group and the nanoAB 160 group approached significance (p=0.0952). All mice in the nanoAB 225, 580 and 1130 groups exhibited tumor regression at day 7 post treatment (FIG. 30). The nanoAB 160 group had 5 of 7 mice exhibit tumor regression at day 7.

These results demonstrate that ABRAXANE®/AVASTIN® complexes with a larger average diameter (e.g., greater than 0.2 µm such as between 0.2 µm and 0.9 µm or between 0.2 µm and 1.5 µm) can be more effective than ABRAXANE®/AVASTIN® complexes with a smaller average diameter (e.g., less than 0.2 µm such as between 0.05 µm and 0.190 µm or between 0.1 µm and 0.190 µm) at seven days post treatment.

Figure 31:
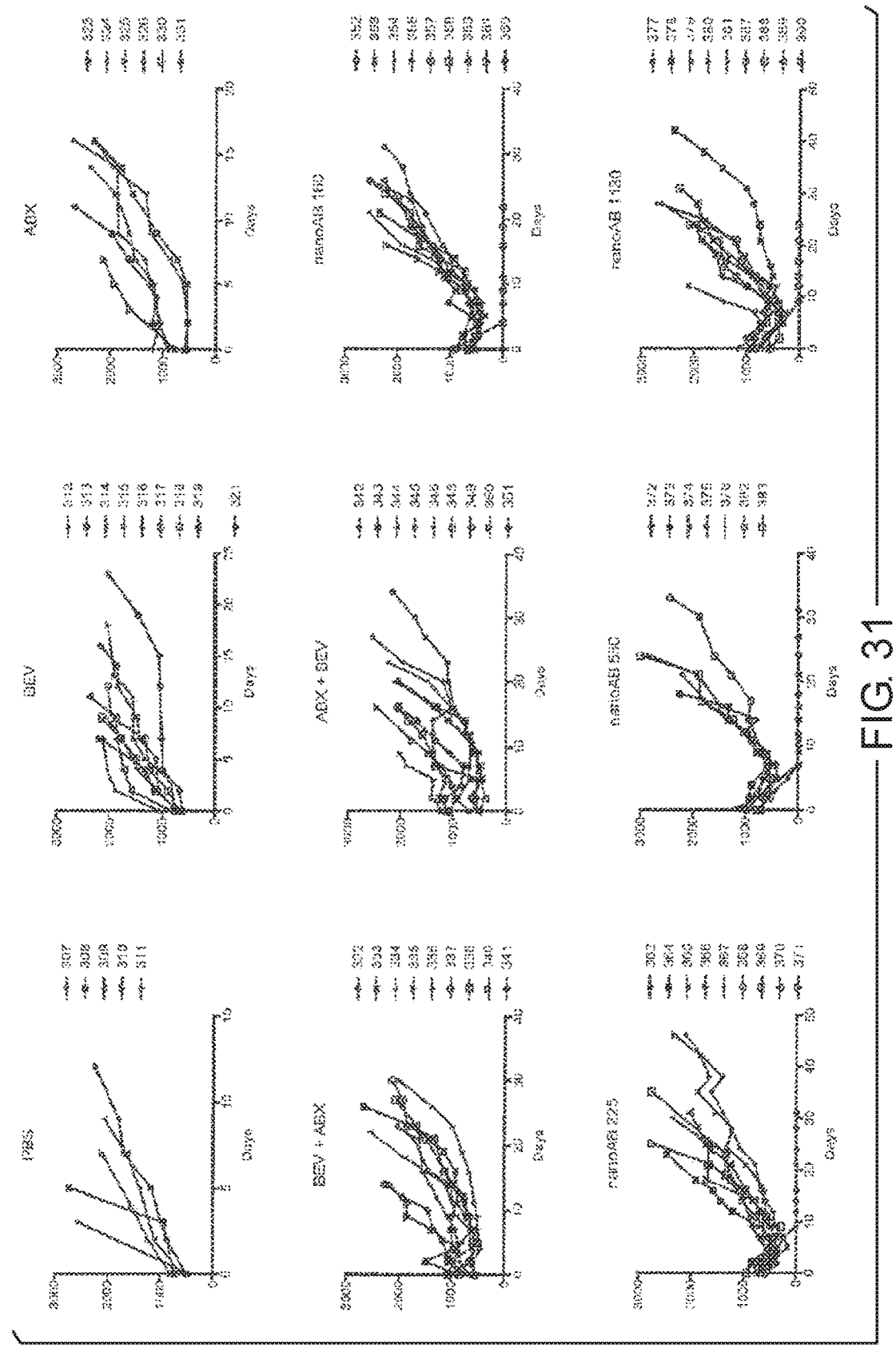
FIG. 31 is a graph plotting tumor size of A375 tumors within nude mice treated intravenously with PBS, Bevacizumab (45 mg/kg) only, ABRAXANE® (30 mg/kg) only, Bevacizumab (45 mg/kg) followed the next day by ABRAXANE® (30 mg/kg) (BEV+ABX), ABRAXANE® (30 mg/kg) followed the next day by Bevacizumab (45 mg/kg) (ABX+BEV), and nanoAB complexes of increasing sizes (0.16 µm, 0.225 µm, 0.58 µm, and 1.13 µm).
Figure 32:
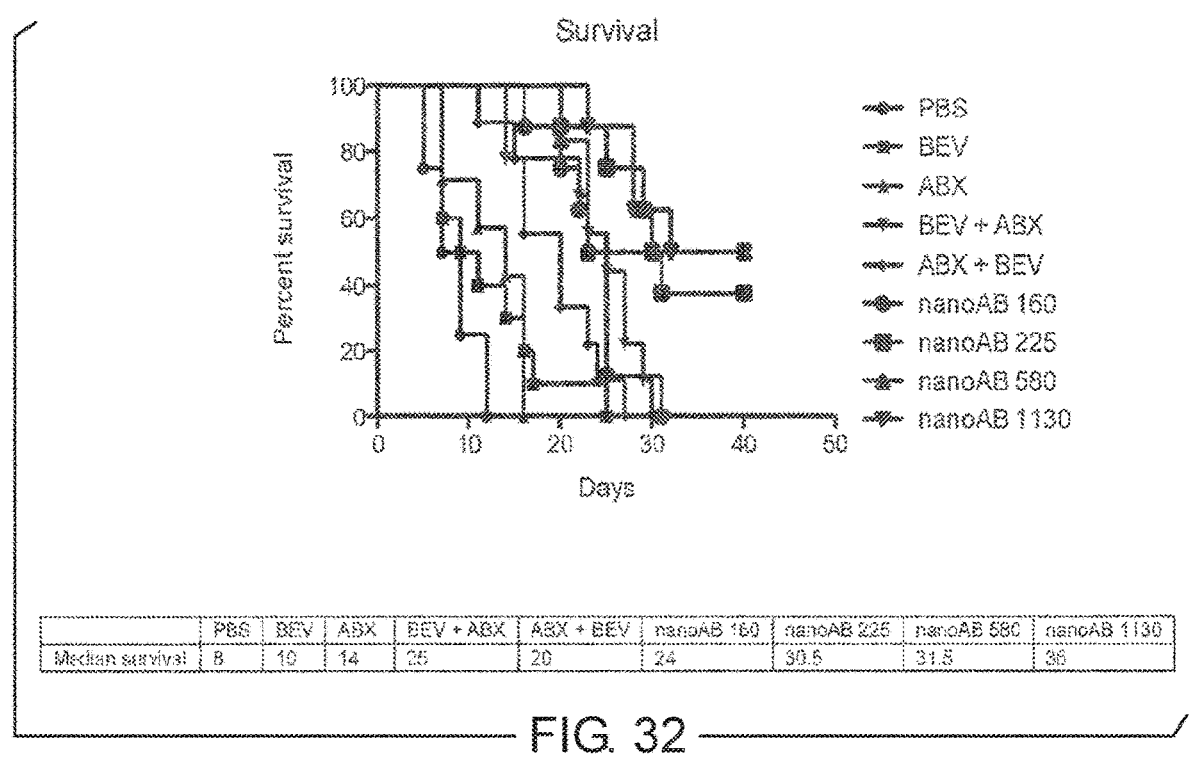
FIG. 32 is a Kaplan Meier graph plotting survival of A375 tumor bearing nude mice treated intravenously with PBS, Bevacizumab (45 mg/kg) only, ABRAXANE® (30 mg/kg) only, Bevacizumab (45 mg/kg) followed the next day by ABRAXANE® (30 mg/kg) (BEV+ABX), ABRAXANE® (30 mg/kg) followed the next day by Bevacizumab (45 mg/kg) (ABX+BEV), and nanoAB complexes of increasing sizes (0.16 µm, 0.225 µm, 0.58 µm, and 1.13 µm).

Tumor size over time was also assessed (FIG. 31). A delay in tumor growth was observed in all mice treated with nanoAB particles, and several mice treated with nanoAB particles experienced complete tumor regression (FIG. 31). Survival data also revealed an improvement for mice treated with ABRAXANE®/AVASTIN® complexes (FIG. 32). In this experiment, while there was no survival advantage for mice treated with nanoAB 160, the remaining nanoAB treatment groups exhibited increased survival as the average particle six of the nanoAB particles increased with nanoAB median survival being 30.5, 31.5, and 36 days for nanoAB 225, 580, and 1130, respectively. In addition, these survival data demonstrate a survival advantage for mice treated with BEV+ABX (25 days) as opposed to ABX+BEV (20 days). These results also suggest that larger ABRAXANE®/AVASTIN® complexes may last longer in circulation or result in a higher deposition of drug in the tumor, thereby resulting in increased tumor regression.

Example 10—ABRAXANE®/AVASTIN® Complexes as Targeted Therapy for Melanoma

Patient Eligibility

The following items are used as inclusion criteria: age ≥18 years, histologic proof of surgically unresectable stage IV malignant melanoma, at least one prior systematic therapy in the metastatic setting that is not an angiogenesis inhibitor, and measurable disease defined as at least one lesion whose longest diameter can be accurately measured as ≥2.0 cm with chest x-ray or as ≥1.0 cm with CT scan, MRI scan, or CT component of a PET/CT. Disease that is measurable by physical examination only is not eligible. Additional inclusion criteria are the following laboratory values obtained ≤14 days prior to registration: hemoglobin >9.0 gm/dL (patients may be transfused to meet Hgb requirement), ANC≥1500/mm, PLT≥100,000/mm$^3$, total bilirubin ≤1.5 upper limit of normal (ULN), SGOT (AST) ≤2.5×ULN Creatinine ≤1.5×ULN, Creatinine ≤1.5×ULN, and an absence of proteinuria at screening as demonstrated by urine protein/creatinine (UPC) ratio <1.0 at screening or urine dipstick for proteinuria <2+. Patients discovered to have ≥2+proteinuria on dipstick urinalysis at baseline should undergo a 24 hour urine collection and demonstrate ≤1 g of protein in 24 hours to be eligible. Additional inclusion criteria are the following: an ECOG Performance Status (PS) of 0, 1, or 2, the ability to understand and the willingness to sign a written informed consent document, a willingness to return to enrolling institution for follow-up (during the active monitoring phase of the study), a life expectancy ≥84 days (3 months), a willingness to provide tissue and blood samples for correlative research purposes, and a negative pregnancy test done ≤7 days prior to registration, for women of childbearing potential only.

Exclusion criteria include a known standard therapy for the patient's disease that is potentially curative or definitely capable of extending life expectancy, prior therapy with an angiogenesis inhibitor, any anti-cancer therapy or investigational agents ≤4 weeks prior to registration, uncontrolled intercurrent illness including, but not limited to, ongoing or active infection, symptomatic congestive heart failure, unstable angina pectoris, cardiac arrhythmia, or psychiatric illness/social situations that would limit compliance with study requirements, a failure to fully recover from acute, reversible effects of prior chemotherapy regardless of interval since last treatment, or brain metastases per MRI or CT at any time prior to registration (patients that have had primary therapy for brain metastasis, i.e., surgical resection, whole brain radiation, or SRT even if stable, are not eligible). Exclusion criteria also include any of the following: pregnant women, nursing women, and men or women of childbearing potential who are unwilling to employ adequate contraception. Exclusion criteria also include co-morbid systemic illnesses or other severe concurrent disease which, in the judgment of the investigator, would make the patient inappropriate for entry into this study or interfere significantly with the proper assessment of safety and toxicity of the prescribed regimens, other active malignancy ≤3 years prior to registration (exceptions: non-melanotic skin cancer or carcinoma-in-situ of the cervix. If there is a history or prior malignancy, they must not be receiving other specific treatment for their cancer), other medical conditions including, but not limited to, history of liver disease such as cirrhosis, chronic active hepatitis, chronic persistent hepatitis or hepatitis B or C; active infection requiring parenteral antibiotics; immunocompromised patients and patients known to be HIV positive and currently receiving antiretroviral therapy (Patients known to be HIV positive, but without clinical evidence of an immunocompromised state, are eligible for this trial); New York Heart Association class II-IV congestive heart failure (Serious cardiac arrhythmia requiring medication); myocardial infarction or unstable angina ≤6 months prior to registration; congestive heart failure requiring use of ongoing maintenance therapy for life-threatening ventricular arrhythmias; clinically significant peripheral vascular disease; history of CNS disease (e.g., primary brain tumor, vascular abnormalities, etc.), clinically significant stroke or TIA≤6 months prior to registration, seizures not controlled with standard medical therapy; or history of hypertensive crisis or hypertensive encephalopathy.

The test schedule is performed as set forth in Table 3.

TABLE 3

Test Schedule

| | Active Monitoring Phase | | | | |
|---|---|---|---|---|---|
| Tests and procedures | ≤21 days prior to registration | ≤14 days prior to registration | Cycle 1 Day 1 | Day 8 | Day 15 | Prior to each subsequent cycle |
| History and exam, wt, PS | | X | | | | X |
| Height | | X | | | | |
| Adverse event assessment | | X | X | X | | X |

TABLE 3-continued

Test Schedule

| Tests and procedures | Active Monitoring Phase | | | | |
|---|---|---|---|---|---|
| | ≤21 days prior to registration | ≤14 days prior to registration | Cycle 1 | | Prior to each subsequent cycle |
| | | | Day 1 | Day 8 | Day 15 | |
| Hematology group WBC ANC Hgb PLT | | X | | | | X |
| Chemistry group (AST, total bili, Alk Phos, Creatinine, potassium, sodium, LDH) | | X | | X | X | X |
| Serum pregnancy test[1] | | X | | | | |
| Tumor Measurement/ Evaluation of indicator lesion (CT, MRI, etc.) | X | | | | | X [2] |
| Mandatory blood specimens | | | X [3] | | | |
| Mandatory tissue specimens, post dose 1/cycle 1 only | | | X [4] | | | |

[1] For women of childbearing potential only. Must be done ≤7 days prior to registration.
[2] Evaluations are performed on day 28 (+/−3 days) of cycles 2, 4, 6, . . . until disease progression. The same imaging modality is used throughout the study.
[3] Blood specimens for PK studies (cycle 1 dose 1, only) are collected in an inpatient facility prior to treatment with ABRAXANE ®/AVASTIN ® complexes, immediately after treatment, and every 4 hours for a total of 48 hours. At 24 and 48 hours, patients also undergo a CBC and chemistry group blood test to asses for toxicity. Study blood tests for PK analysis are collected prior to each treatment with ABRAXANE ®/AVASTIN ® complexes during cycle #1 (day 8 and 15).
[4] Study tissue specimens are collected between 20 and 26 hours after dose 1/cycle 1 of therapy with ABRAXANE ®/AVASTIN ® complexes while the patients are hospitalized in an in-patient facility. Patients undergo ultrasound or CT guided (radiologist's discretion) 18 g core needle biopsy (3 passes). One core is collected and processed for paraffin embedding (FFPE); the other 2 cores are snap frozen for paclitaxel quantification.

Protocol Treatment with ABRAXANE®/AVASTIN® Complexes

Actual weight or estimated dry weight if fluid retention is used. The treatment schedule for ABRAXANE®/AVASTIN® complexes is repeated each month (every 28 days+/−3 days) or until disease progression, patient refusal, or unacceptable toxicity (Table 4) with the indicated dose escalation scheme (Table 5) and dose limiting toxicities (Table 6).

TABLE 4

| Agent | Dose | Route | Days | ReRx |
|---|---|---|---|---|
| ABRAXANE ®/ AVASTIN ® complexes | assigned at time of registration | IV over 60 minutes (only 1$^{st}$ dose; subsequent doses infused over 30 minutes) | 1, 8 and 15 | Every 28 days* |

TABLE 5

Dose Escalation Scheme.

| Dose Level | Dose (ABX) | Dose (BEV) |
|---|---|---|
| −2 | 75 mg/m$^2$ | 30 mg/m$^2$ |
| −1 | 100 mg/m$^2$ | 40 mg/m$^2$ |
| 1* | 125 mg/m$^2$ | 50 mg/m$^2$ |
| 2 | 150 mg/m$^2$ | 60 mg/m$^2$ |
| 3 | 175 mg/m$^2$ | 70 mg/m$^2$ |

*Starting dose.

TABLE 6

Dose Limiting Toxicities (DLT).

| Toxicity | DLT Definition |
|---|---|
| Hematologic | Grade 4 ANC, Grade 4 Hgb, or PLT <25,000 |
| Renal | Serum creatinine ≥2 times baseline |

TABLE 6-continued

Dose Limiting Toxicities (DLT).

| Toxicity | DLT Definition |
|---|---|
| Other nonhematologic | ≥ grade 3 as per NCI Common Terminology Criteria for Adverse Events (CTCAE) version 4.0 |

Determination of Maximum Tolerated Dose (MTD)

The maximum tolerated dose is defined as the highest dose level among those tested where at most one out of six patients develops a DLT prior to the start of their second cycle of treatment and the next highest dose level is such that two out of a maximum of six patients treated at this dose level developed a DLT prior to the start of their second cycle of treatment.

Enrollment and Determination of MTD

A minimum of two or a maximum of six patients are accrued to a given dose level. For dose level 1 (and if accrued to, dose levels −1 & −2), enrollment is temporarily halted after each patient has been enrolled in order to gather acute adverse event data over the first cycle of their treatment. For dose levels 2 & 3, patients are accrued to these dose levels so that at any given time no more than two patients are receiving their first cycle of treatment and acute adverse event data over the first treatment cycle for all other patients treated at the current dose level is known. If, at any time in the enrollment process, two patients treated at the current dose level develop a DLT during the first cycle of treatment, enrollment is closed to that dose level. Enrollment is re-opened to the next lower dose level if fewer than six patients have been treated at that dose level. If none of the first three patients treated at a given dose level develops a DLT during the first cycle of treatment, enrollment to the dose level is closed and enrollment is reopen at next higher dose level. If there are no other higher dose levels to be tested, three additional patients are enrolled at the current dose level to confirm MTD. If one of the first three patients treated at a given dose level develops a DLT during the first cycle of treatment, three additional patients are enrolled (sequentially) onto the current dose level. If, at any time in the enrollment of these three additional patients, a patient develops a DLT, enrollment is closed to this dose level. Enrollment is re-opened to the next lower dose level if fewer than six patients are treated at that dose level. If none of these three additional patients develops a DLT during the first cycle of treatment, enrollment to this dose level is closed and enrollment is reopened at next higher dose level. If there are no other higher dose levels to be tested, this is considered the MTD.

For this protocol, the patient returns for evaluation and retreatment (at least every 28+/−3 days) according to the schedule. If a patient fails to complete the first cycle of treatment for reasons other than toxicity, an additional patient is enrolled to replace this patient.

Dosage Modification Based on Adverse Events

The modifications in Table 7 are strictly followed until individual treatment tolerance is ascertained. If multiple adverse events (Table 8) are seen, dose is administered based on greatest reduction required for any single adverse event observed. Dose modifications apply to the treatment given in the preceding cycle and are based on adverse events observed since the prior dose.

TABLE 7

Dose Levels Based on Adverse Events.

| | ABRAXANE ®/AVASTIN ® complexes - Both drugs are reduced | |
|---|---|---|
| Dose Level | ABX dose | Accompanying BEV dose (40% of ABX dose) |
| 2 | 175 mg/m$^2$ | 70 mg/m$^2$ |
| −1 | 150 mg/m$^2$ | 60 mg/m$^2$ |
| 1 | 125 mg/m$^2$ | 50 mg/m$^2$ |
| −2 | 100 mg/m$^2$ | 40 mg/m$^2$ |
| −2 | 75 mg/m$^2$ | 30 mg/m$^2$ |

TABLE 8

Use Common Terminology Criteria for Adverse Events (CTCAE) v. 4.0* unless otherwise specified

| CTCAE Category | Adverse Event | Dose Reduction |
|---|---|---|
| Investigations | ANC <1000 or PLT <75,000 | Day 1: Hold until counts above these levels. Day 8: Omit dose that day and retreat at same dose level on day 15 if counts have recovered. Day 15: Omit dose that day. NOTE: if two consecutive cycles of therapy require omission of a dose, subsequent treatment cycles should begin (day 1) at next lower dose. |
| | AST or Alkaline Phosphatase ≥Grade 2 | Day 1: Hold until resolved to <Grade 2 then reduce dose by ONE dose level. If treatment needs to be held >4 weeks, discontinue study treatment and go to event monitoring. |
| Neurology disorders | Neuropathy ≥Grade 2 | Day 1: Hold until resolved to <Grade 2 then reduce dose by ONE dose level. Day 8 OR 15 - Omit dose that day. If resolved to <Grade 2 by next scheduled dose, then dose reduce by one level If treatment needs to be held >4 weeks, discontinue study treatment and go to Event Monitoring |
| All other non-hematologic adverse events | ≥Grade 3 | Day 1: Hold until resolved to ≤ Grade 2 then reduce dose by ONE dose level. Day 8: Omit dose that day. If resolved to ≤ Grade 2 by day 15, then dose reduce by one level and retreat. Day 15: Omit dose that day. NOTE: if two consecutive cycles of therapy require omission of a dose, subsequent treatment cycles should begin (day 1) at next lower dose. If treatment needs to be held >4 weeks, discontinue study treatment and go to Event Monitoring |
| Gastrointestinal Disorders | Bowel perforation | Discontinue all study treatment and proceed to Event Monitoring |
| | Bowel Obstruction Grade 1 | Continue patient on study for partial bowel obstruction NOT requiring medical intervention. Hold for partial obstruction requiring medical |

TABLE 8-continued

Use Common Terminology Criteria for Adverse Events (CTCAE) v. 4.0*
unless otherwise specified

| CTCAE Category | Adverse Event | Dose Reduction |
|---|---|---|
| | Grade 2<br>Grade 3 or 4 | intervention. If resolved to Grade 0 within 4 weeks, treatment may be restarted. If treatment needs to be held >4 weeks, discontinue all study treatment and go to Event Monitoring.<br>For complete bowel obstruction, discontinue study treatment and proceed to Event Monitoring |
| Cardiac Disorders | Hypertension ≥Grade 3 | Hypertension should be treated as per general practice. If hypertension (≥150/100) persists despite treatment, hold treatment until blood pressure is below this level<br>If treatment needs to be held >4 weeks due to uncontrolled hypertension, discontinue study treatment and go to Event Monitoring. |
| | Left ventricular systolic function- Grade 3<br>Grade 4 | Hold until resolution to Grade ≤1. If treatment needs to be held >4 weeks, discontinue all study treatment and go to Event Monitoring.<br>Discontinue treatment and proceed to Event Monitoring |
| Respiratory, thoracic and mediastinal disorders | Bronchopulmonary Hemorrhage ≥ Grade 2 | Discontinue all study treatment and proceed to Event Monitoring |
| Coagulation | Hemorrhage Grade 3<br>Grade 4 | Hold until ALL of the following criteria are met:<br>1. Bleeding has resolved and Hb is stable.<br>2. There is no bleeding diathesis that would increase the risk of therapy.<br>3. There is no anatomic or pathologic condition that could increase the risk of hemorrhage recurrence.<br>If treatment needs to be held >4 weeks, discontinue study treatment and go to Event Monitoring<br>Patients who experience a recurrence of Grade 3 hemorrhage are to discontinue all study treatment and proceed to Event Monitoring.<br>Discontinue study treatment and proceed to Event Monitoring |
| | Bleeding diathesis Grade 3 or 4 | Discontinue study treatment and proceed to Event Monitoring |
| Vascular disorders | Venous thrombosis Grade 3 or asymptomatic Grade 4 Symptomatic Grade 4 | Hold treatment. If the planned duration of full-dose anticoagulation is <2 weeks, treatment should be held until the full-dose anticoagulation period is over.<br>If the planned duration of full-dose anticoagulation is >2 weeks, treatment may be resumed during the period of full-dose anticoagulation IF all of the criteria below are met:<br>The subject must have an in-range INR (usually 2-3) on a stable dose of warfarin, or on stable dose of heparin prior to restarting treatment.<br>The subject must not have pathological conditions that carry high risk of bleeding (e.g. tumor involving major vessels or other conditions)<br>The subject must not have had hemorrhagic events while on study<br>If thromboemboli worsen/recur upon resumption of study therapy, discontinue treatment.<br>Discontinue treatment and proceed to Event Monitoring |
| | Arterial thrombosis (Angina, myocardial infarction, transient ischemic attack, cerebrovascular accident, or any other arterial thromboembolic events) ANY Grade | Discontinue treatment and proceed to Event Monitoring |

Ancillary Treatment/Supportive Care

Routine use of colony-stimulating factors (G-CSF or GM-CSF) is not recommended. Prophylactic use of colony-stimulating factors during the study is not allowed. Therapeutic use in patients with serious neutropenic complications such as tissue infection, sepsis syndrome, fungal infection, etc., may be considered at physician discretion. Recombinant erythropoietin to maintain adequate hemoglobin levels and avoid packed red blood cell transfusions is allowed.

Patients should receive full supportive care while on this study. This includes blood product support, antibiotic treatment and treatment of other newly diagnosed or concurrent medical conditions. All blood products and concomitant medications such as antidiarrheals, analgesics, and antiemetics received from the first administration of study drugs until 30 days after the final dose are to be recorded in the medical record. Patients participating in phase I program clinical trials are not to be considered for enrollment in any other study involving a pharmacologic agent-(drugs, biologics, immunotherapy approaches, gene therapy) whether for symptom control or therapeutic intent.

Hypersensitivity Reactions

Patients do not require premedication prior to administration of ABRAXANE®/AVASTIN® complexes. In the unlikely event of a hypersensitivity reaction, treatment with antihistamines, H2 blockers, and corticosteroids is recommended. Patients should be pre-medicated with the typical regimen for paclitaxel regimens for subsequent cycles. In the unlikely event of a mild hypersensitivity reaction, premedication may be administered using the premedication regimen the institution typically uses for solvent-based paclitaxel.

ABRAXANE®/AVASTIN® Complexes ABRAXANE®/AVASTIN® complexes are prepared as a hazardous low risk product. ABRAXANE® is supplied as a white to off-white lyophilized powder containing 100 mg of paclitaxel and approximately 900 mg Albumin Human USP (HA) as a stabilizer in a 50 mL, single-use vial. Each vial of the lyophilized product is reconstituted as set forth below. Unreconstituted ABRAXANE® is stored at controlled room temperature in its carton. Reconstituted ABRAXANE® is used immediately. AVASTIN® (bevacizumab) is classified as an anti-VEGF monoclonal antibody and a vascular endothelial growth factor (VEGF) inhibitor. AVASTIN® is supplied in 100 mg (4 mL) glass vials, with a concentration of 25 mg/mL. Vials contain AVASTIN® typically with phosphate, trehalose, polysorbate 20, and sterile water for injection (SWFI), USP. Vials contain no preservative and are suitable for single use only. AVASTIN® vials are stored in a refrigerator at 2° C.-8° C. AVASTIN® vials are kept in the outer carton due to light sensitivity. They are not frozen or shaken.

Chemical and physical in-use stability of AVASTIN® is acceptable for 48 hours at 2° C.-30° C. in 0.9% sodium chloride solution. AVASTIN® is not administered or mixed with dextrose solution. AVASTIN® is further diluted as set forth below.

The ABRAXANE®/AVASTIN® complexes are prepared as a hazardous low risk product. The dose appropriate number of 4 mL vials of 25 mg/mL AVASTIN® (bevacizumab) are obtained, and each vial is further diluted per the following directions to 4 mg/mL. The dose appropriate number of ABRAXANE® (paclitaxel) 100 mg vials is obtained and each vial is reconstituted per the following directions to a final concentration containing 10 mg/mL nanoparticle albumin-bound (nab) paclitaxel. It is not a requirement to use filter needles in the preparation of, or in-line filters during administration. In addition, filters of pore-size less than 15 micrometers are to be avoided.

As with other cytotoxic anticancer drugs, caution is exercised in handling ABRAXANE®. The use of gloves is recommended.

Using a sterile 3 mL syringe, 1.6 mL (40 mg) of AVASTIN® 25 mg/mL is withdraw and slowly injected, over a minimum of 1 minute, onto the inside wall of each of the vials containing 100 mg of ABRAXANE®. Unused AVASTIN® left in the 25 mg/mL vial is discarded, as the product contains no preservatives. Injecting the AVASTIN solution directly onto the lyophilized cake is avoided as this will result in foaming. Using a sterile 12 mL sterile syringe, 8.4 mL of 0.9% Sodium Chloride Injection, USP, is withdraw and slowly injected, over a minimum of 1 minute, onto the inside wall of each vial containing ABRAXANE® 100 mg and AVASTIN® 40 mg. Once the addition of AVASTIN® 1.6 mL and 0.9% Sodium Chloride Injection, USP 8.4 mL is complete in each vial, each vial is gently swirled and/or inverted slowly for at least 2 minutes until complete dissolution of any cake/powder occurs. The generation of foam is avoided. The concentration of each vial is 100 mg/10 mL ABRAXANE® and 40 mg/10 mL AVASTIN®. The vials containing the ABRAXANE® and AVASTIN® are allowed to sit for 60 minutes. The vial(s) are gently swirled and/or inverted every 10 minutes to continue to mix the complexes. After 60 minutes is elapsed, a sterile 60- to 100-mL syringe (appropriate size for the volume being administered) is used to withdraw the calculated dosing volume of ABRAXANE® and AVASTIN® from each vial. A sufficient quantity of 0.9% Sodium Chloride Injection, USP is added to make the final concentration of ABRAXANE® 5 mg/mL and AVASTIN® 2 mg/mL. The syringe is gently swirled and/or inverted slowly for 1 minute to mix. The storage and stability is for up to 4 hours at room temperature following final dilution.

Administration

The IV initial complex dose is infused over 60 minutes via syringe pump. The infusion may be shortened to 30 minutes if the initial infusion is well tolerated. Infusion is monitored closely during the infusion process for signs/symptoms of an infusion reaction. The patient's line is flushed after administration with 20 mL 0.9% Sodium Chloride. An example calculation and preparation is as follows:

Dose level 1: ABRAXANE® 125 mg/m$^2$/AVASTIN® 50 mg/m$^2$ BSA=2 m$^2$

Doses required: ABRAXANE® 250 mg/AVASTIN® 100 mg Obtain three 100 mg vials of ABRAXANE®.

Obtain one 100 mg vial of AVASTIN® 25 mg/mL.

Withdraw 1.6 mL (40 mg) of AVASTIN® 25 mg/mL and slowly inject over 1 minute onto the inside wall of one of the 100 mg ABRAXANE® vials. Repeat this procedure for each of the remaining two ABRAXANE® 100 mg vials.

Add 8.4 mL 0.9% Sodium Chloride Injection, USP onto the inside wall of one of the vials containing ABRAXANE® and AVASTIN®. Repeat this procedure for each of the remaining two ABRAXANE® and AVASTIN® vials.

Let mixture sit for 60 minutes (swirling every 10 minutes). The final concentration of each vial should be 100 mg ABRAXANE®/10 mL and 40 mg AVASTIN®/10 mL.

Withdraw 25 mL from the ABRAXANE® and AVASTIN® containing vial and place in a 100 mL sterile syringe. Add 25 mL 0.9% Sodium Chloride Injection, USP for a final ABRAXANE® concentration of 5 mg/mL and AVASTIN® concentration of 2 mg/mL. Infuse via syringe pump over 60 minutes (first dose, 30 minutes subsequent doses).

Response to ABRAXANE®/AVASTIN® complex treatment

Each patient's response to treatment with a ABRAXANE®/AVASTIN® complex formulation is monitored.

Example 11—Making ABRAXANE®/AVASTIN® Complexes

Figure 25:
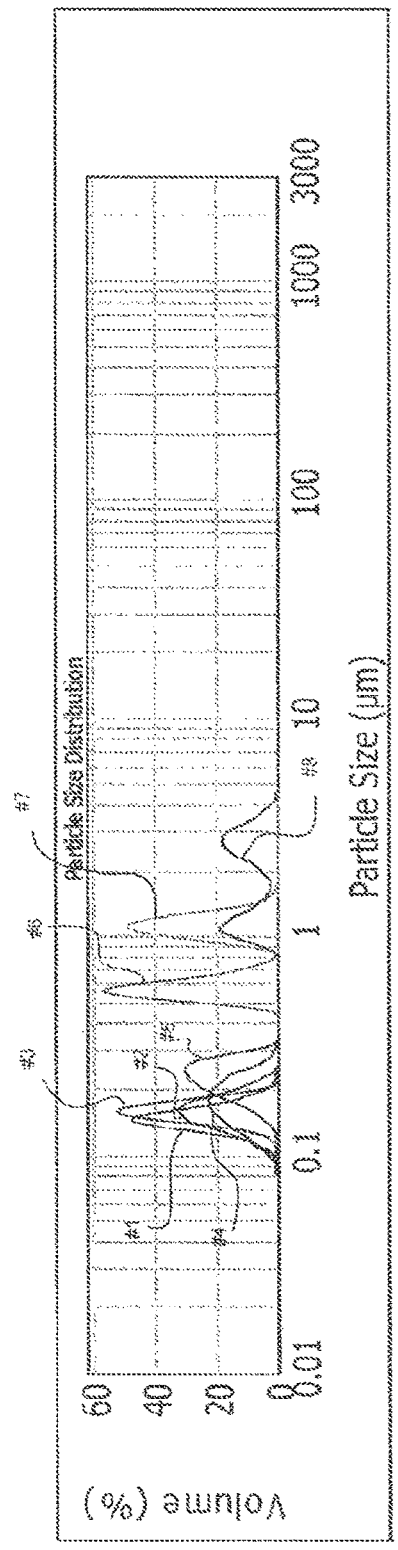
FIG. 25 is a graph plotting the particle size distribution for ABRAXANE® (ABX) dissolved in Bevacizumab (BEV) as determined using a Mastersizer 2000E (Malvern Instruments Ltd., Worcestershire, England). ABX (10 mg/mL) was reconstituted in 1 mL of the indicated amount of BEV, and the mixtures were incubated at room temperature for 30 minutes.

ABRAXANE® was incubated with various increasing concentrations of AVASTIN® to form ABRAXANE®/AVASTIN® complexes of increasing diameter. Ten milligrams of ABRAXANE® was reconstituted in 1 mL of AVASTIN® at 0, 2, 4, 6, 8, 10, 15, and 25 mg/mL, and the mixture was incubated at room temperature for 30 minutes. After incubation, the distributions of particle sizes were determined with the Mastersizer 2000. The median particle size ranged from 0.146 µm to 2.166 µm for 0 and 25 mg/mL AVASTIN®, respectively (FIG. 25). It appeared that as AVASTIN® concentrations increased, the particles formed singlets, doublets, and tetramers. These results demonstrate that the antibody concentration in which ABRAXANE® is incubated impacts the size of the nanoparticle. As demonstrated herein, manipulating the size of the particles can change the pharmacokinetics of the drug complex as well as its bio-distribution, which in turn can improve the clinical efficacy of the drug complex.

Example 12—Making ABRAXANE®/Rituxan® Complexes

Figure 26:
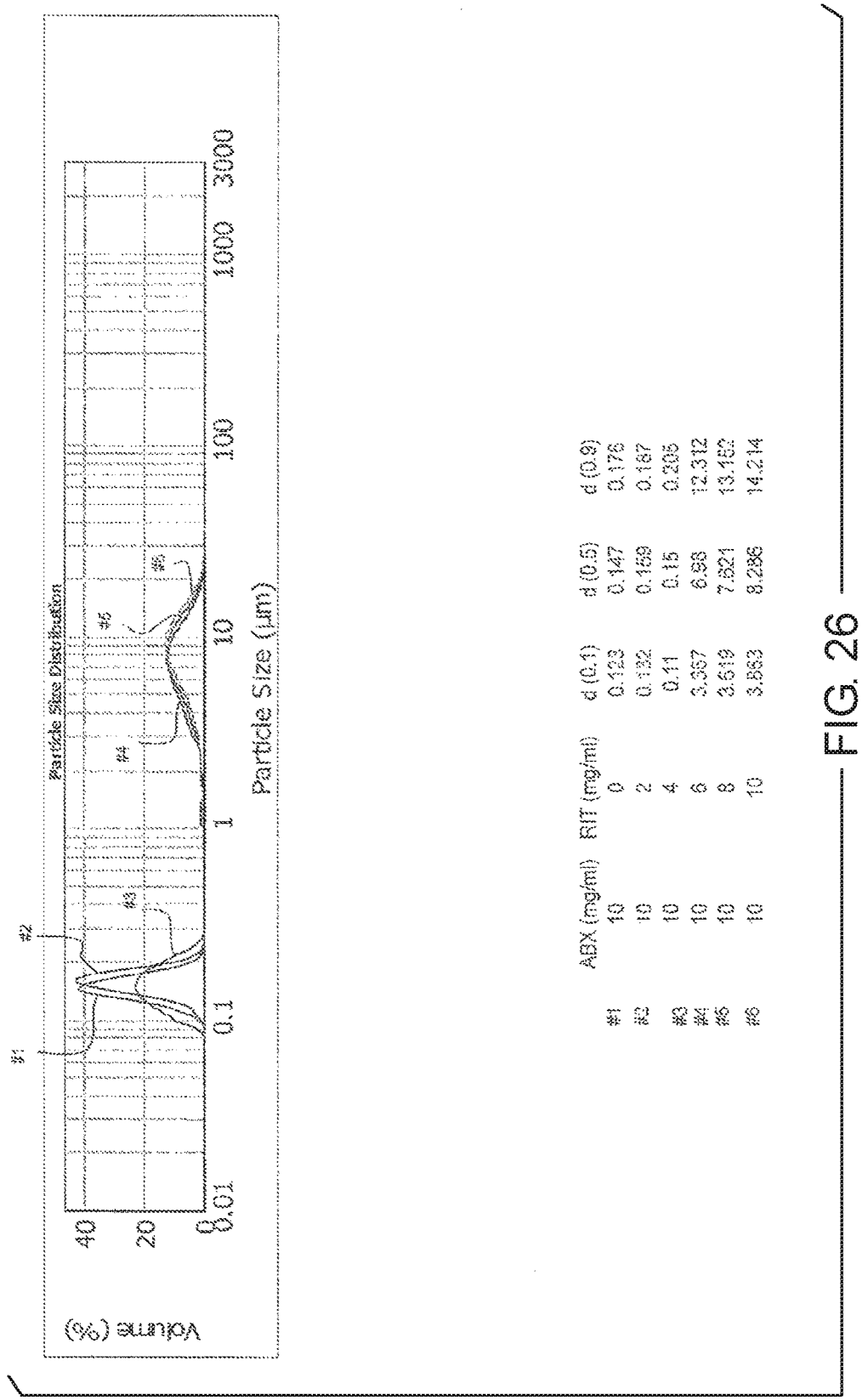
FIG. 26 is a graph plotting the particle size distribution for ABRAXANE® (ABX) dissolved in Rituxan (RIT) as determined using a Mastersizer 2000E (Malvern Instruments Ltd., Worcestershire, England). ABX (10 mg/mL) was reconstituted in 1 mL of the indicated amount of RIT, and the mixtures were incubated at room temperature for 30 minutes.

ABRAXANE® was incubated with various increasing concentrations of Rituxan® (rituximab) to form ABRAXANE®/Rituxan® complexes of increasing diameter. Ten milligrams of ABRAXANE® was reconstituted in 1 mL of Rituxan® at 0, 2, 4, 6, 8, and 10 mg/mL, and the mixture was incubated at room temperature for 30 minutes. After incubation, the distributions of particle sizes were determined with the Mastersizer 2000. The median particle size ranged from 0.147 µm to 8.286 µm for 0 and 10 mg/mL Rituxan®, respectively (FIG. 26). These results demonstrate that the antibody concentration in which ABRAXANE® is incubated impacts the size of the nanoparticle. These results also demonstrate that different humanized therapeutic antibodies can result in different particle sizes when mixed with ABRAXANE® at the same concentration. As demonstrated herein, manipulating the size of the particles can change the pharmacokinetics of the drug complex as well as its bio-distribution, which in turn can improve the clinical efficacy of the drug complex.

Example 13—Making ABRAXANE®/Herceptin® Complexes

Figure 27:
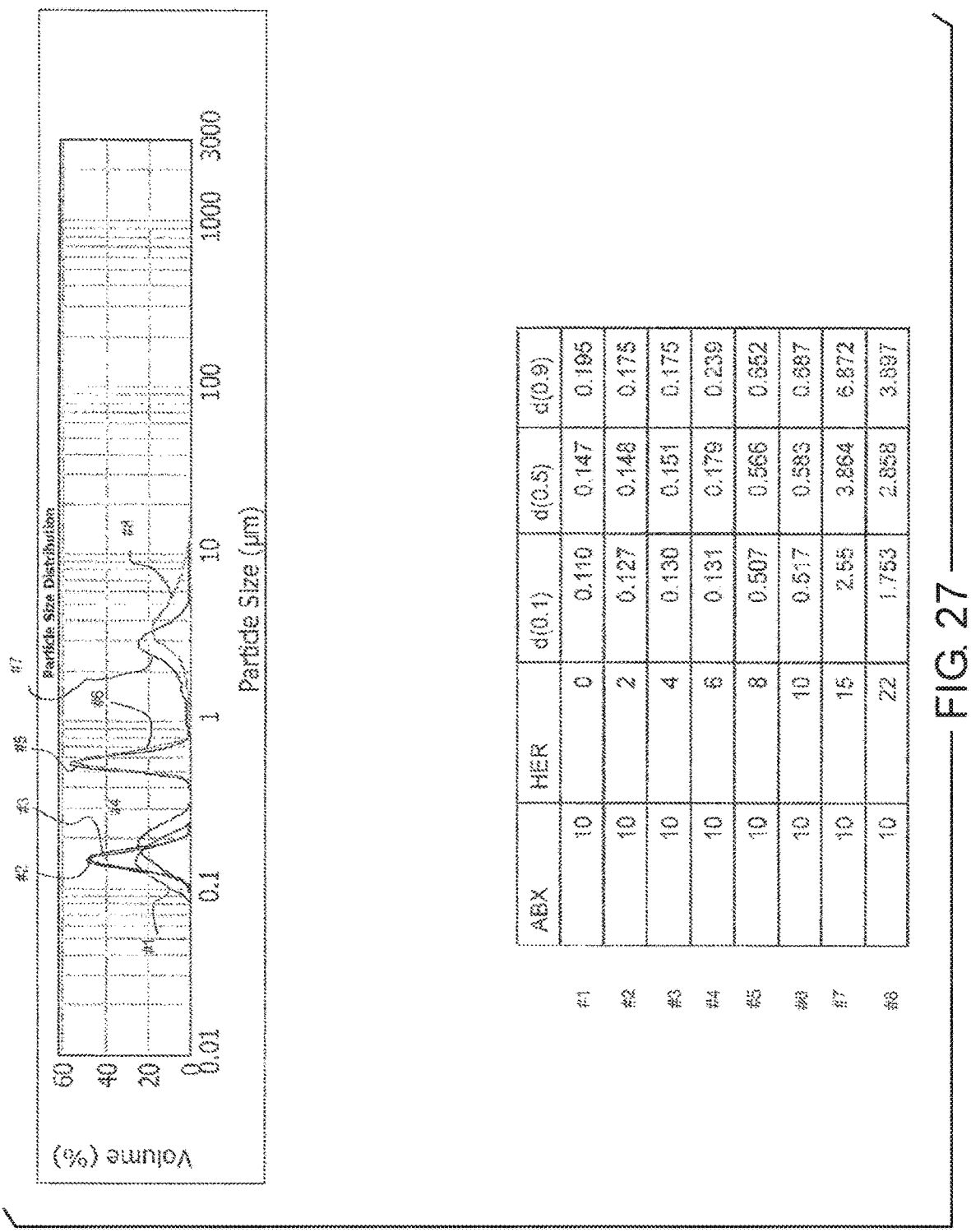
FIG. 27 is a graph plotting the particle size distribution for ABRAXANE® (ABX) dissolved in Herceptin (HER) as determined using a Mastersizer 2000E (Malvern Instruments Ltd., Worcestershire, England). ABX (10 mg/mL) was reconstituted in 1 mL of the indicated amount of HER, and the mixtures were incubated at room temperature for 30 minutes.

ABRAXANE® was incubated with various increasing concentrations of Herceptin® (also referred to as rituximab or trastuzumab) to form ABRAXANE®/Herceptin® complexes of increasing diameter. Ten milligrams of ABRAXANE® was reconstituted in 1 mL of Herceptin® at 0, 2, 4, 6, 8, 10, 15, and 22 mg/mL, and the mixture was incubated at room temperature for 30 minutes. After incubation, the distributions of particle sizes were determined with the Mastersizer 2000. The median particle size ranged from 0.147 µm to 2.858 µm for 0 and 22 mg/mL Herceptin®, respectively (FIG. 27). These results demonstrate that the antibody concentration in which ABRAXANE® is incubated impacts the size of the nanoparticle. These results also demonstrate that different humanized therapeutic antibodies can result in different particle sizes when mixed with ABRAXANE® at the same concentration. As demonstrated herein, manipulating the size of the particles can change the pharmacokinetics of the drug complex as well as its bio-distribution, which in turn can improve the clinical efficacy of the drug complex.

Example 14—Dissociation Constants

The association and dissociation of AVASTIN® with human serum albumin and ABRAXANE® were determined. In this experiment, biotinylated AVASTIN® was bound to a streptavidin sensor. After AVASTIN® loading to the sensor, the sensor was exposed to either 1 mg/mL of human serum albumin or 1 mg/mL of ABRAXANE®. This experiment demonstrated that AVASTIN® binds to both human serum albumin and ABRAXANE®. The dissociation constants were calculated to be $6.2 \times 10^{-6}$ and $5.873 \times 10^{-7}$ for human serum albumin and ABRAXANE®, respectively.

The association and dissociation of albumin with AVASTIN® and AVASTIN® with ABRAXANE® were determined. In this experiment, biotinylated AVASTIN® or biotinylated Albumin® was bound to a streptavidin sensor. After albumin or AVASTIN® loading to the sensor, the sensor was exposed to 1 mg/mL of AVASTIN® or 1 mg/mL of ABRAXANE®, respectively. This experiment demonstrated that albumin binds to AVASTIN® and AVASTIN® binds to ABRAXANE®. The dissociation constant calculated for albumin and AVASTIN® was $6.588 \times 10^{-10}$. The dissociation constant calculated for AVASTIN® and ABRAXANE® in this experiment was $1.698 \times 10^{-5}$.

Figure 33:
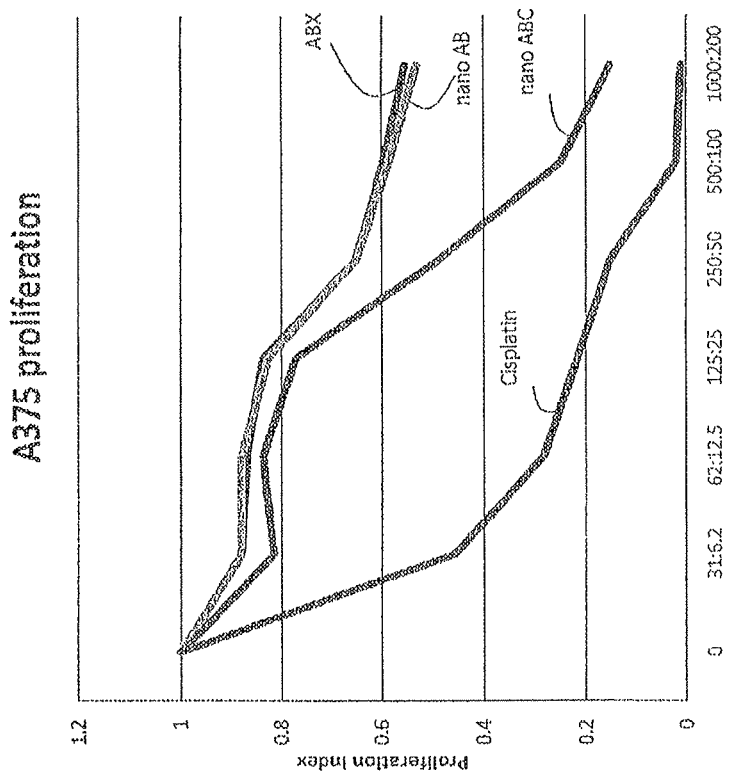
FIG. 33 is a graph plotting the proliferation (proliferation index) of A375 melanoma tumor cells treated in vitro with ABRAXANE® (ABX) 0-1000 µg/mL, nanoAB (ABX:BEV) 0-1000 µg/mL, Cisplatin 0-200 µg/mL, or nanoABC (0-1000 µg/mL ABX, 4 mg/mL BEV, and 0-200 µg/mL Cisplatin).

Example 15—ABRAXANE®/AVASTIN®/Cisplatin Complexes Inhibit Tumor Cell Proliferation Proliferation of A375 melanoma tumor cells in vitro following exposure to various treatments was assessed. Briefly, cells were exposed to increasing concentrations of (a) ABRAXANE® only (ABX; 0-1000 µg/mL), (b) cisplatin only (0-200 µg/mL), (c) ABRAXANE®/AVASTIN® complexes with an average diameter of 0.155 (nanoAB; 0-1000 µg/mL), or ABRAXANE®/AVASTIN®/cisplatin complexes with an average diameter of 0.141. Cisplatin is a chemotherapy drug that is highly effective against tumors, but has such a high toxicity to normal tissue that it is infrequently used in the clinic. One can appreciate the high toxicity of cisplatin alone in that 100% of cells are killed at 100 µg/mL (FIG. 33). With reference to FIG. 33, the complexes were made with an ABRAXANE®: AVASTIN® at a 2.5 to 1 ratio. The x-axis numbers refer to only the paclitaxel and cisplatin concentrations with the higher number being the paclitaxel concentration and the other being cisplatin. The range of doses were different because cisplatin is so toxic. To make the ABRAXANE®/AVASTIN®/cisplatin complexes, ABRAXANE® (10 mg/mL), AVASTIN® (4 mg/mL), and cisplatin (2 mg/mL) were co-incubated at room temperature for 30 minutes. The nanoparticles were spun for 10 minutes at 5000 rpm to remove unbound cisplatin. The nanoparticles were resuspended in 0.9% saline and added to the wells containing 50,000 A375 cells. The cells were incubated overnight at 37° C. The cells were stained with a thymidine analog, EdU, which incorporates into the DNA as cells proliferate. Cells that are actively proliferating stain positive. The proliferation index was calculated as the % positive cells in treated cells/% positive cells in untreated cells. This resulted in an index of the number of proliferating cells for treatment relative to the highest reading of % positive for untreated cells.

Cisplatin was determined to be present in the nanoABC particles due to the increase in drug toxicity relative to ABRAXANE® alone and nanoAB (FIG. 33). The toxicity of nanoABC, however, was not as high as cisplatin only, suggesting that cisplatin may be used in the complex to increase drug toxicity to the tumor while having limited toxicity to normal tissue.

Figure 34:
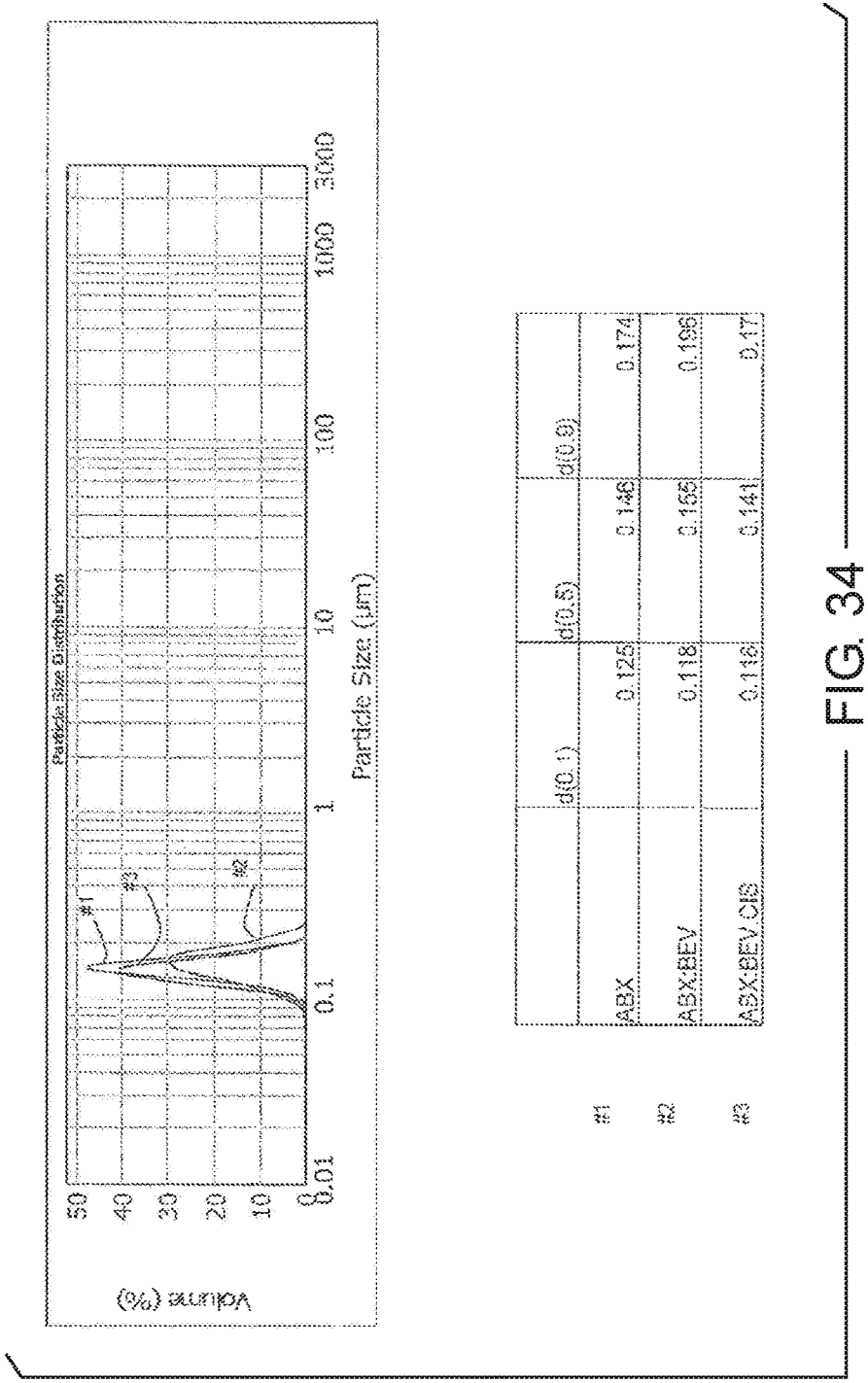
FIG. 34 is a graph plotting the particle size distribution for particles of ABRAXANE® (ABX) only, ABRAXANE® together with Bevacizumab (ABX:BEV), and ABRAXANE® together with Bevacizumab and Cisplatin (ABX:BEV:CIS; or ABC) as determined using a Mastersizer 2000E (Malvern Instruments Ltd., Worcestershire, England).

The particle size distributions for the ABRAXANE® particles, the ABRAXANE®/AVASTIN® complexes (nanoAB), and the ABRAXANE®/AVASTIN®/cisplatin complexes (nanoABC) used above were determined. The median size of the particles was 0.146 μm, 0.155 μm, and 0.141 μm, for ABX, nanoAB, and nanoABC, respectively (FIG. 34). These results demonstrate that particle size when cisplatin is added was not different from the particle size when only ABRAXANE® and AVASTIN® are present.

Example 16—Treating Cancer with ABRAXANE®/AVASTIN®/Cisplatin Complexes

Athymic nude mice were injected with $1\times10^6$ A375 human melanoma tumor cells. The tumors were allowed to grow, and when the tumors were 600 to 1000 mm$^3$, the mice were treated intravenously with PBS, ABRAXANE® (30 mg/kg), cisplatin (2 mg/kg), nanoAB 160 (30 mg/mL ABX and 8 mg/mL BEV), nanoAB160 and cisplatin at the same concentrations as above, and nanoABC (30 mg/kg ABX, 8 mg/kg BEV, and 2 mg/kg Cis). NanoABC was prepared as follows: 10 mg of ABRAXANE® was reconstituted in 4 mg/mL bevacizumab and 2 mg/mL cisplatin and allowed to incubate at room temperature for 30 minutes. Following incubation, the complexes were diluted for mouse injection. Mice were treated once, and tumor growth was monitored for at least 80 days for all mice.

Figure 35:
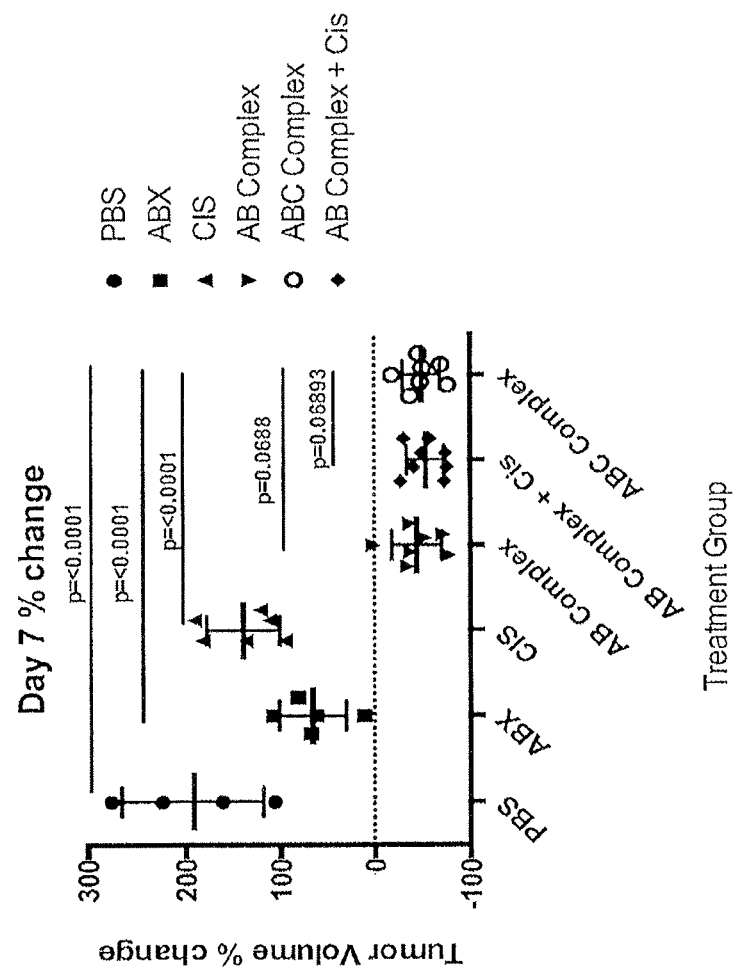
FIG. 35 is a graph plotting percent change at seven days in tumor size from baseline of A375 tumor bearing nude mice treated intravenously with PBS, ABRAXANE® (30 mg/kg), cisplatin (2 mg/kg), nanoAB complexes (30 mg/mL ABX and 8 mg/mL BEV), nanoAB (30 mg/mL ABX and 8 mg/mL BEV) plus cisplatin (2 mg/kg), and nanoABC (30 mg/kg ABX, 8 mg/kg BEV, and 2 mg/kg Cis).
Figure 36:
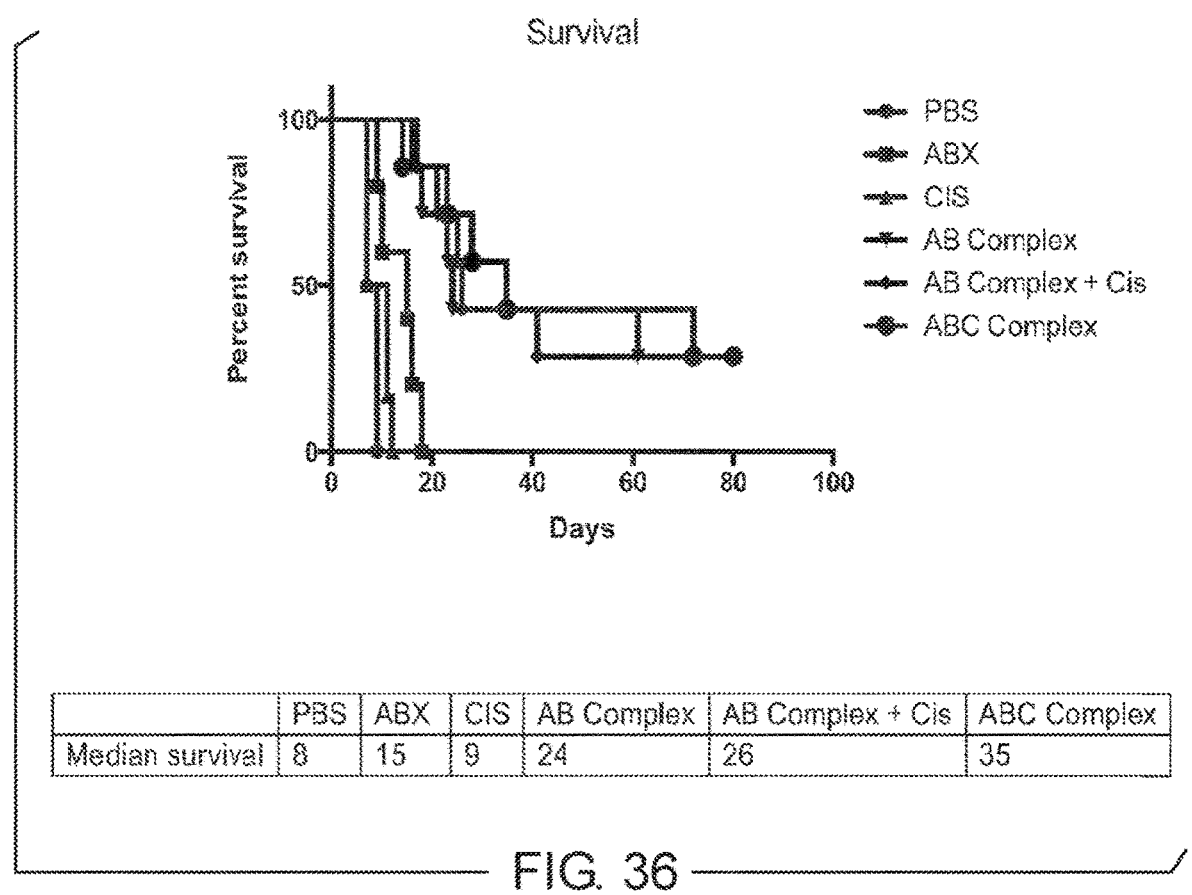
FIG. 36 is a Kaplan Meier graph plotting survival of A375 tumor bearing nude mice treated with PBS, ABRAXANE® (30 mg/kg), cisplatin (2 mg/kg), nanoAB complexes (30 mg/mL ABX and 8 mg/mL BEV), nanoAB (30 mg/mL ABX and 8 mg/mL BEV) plus cisplatin (2 mg/kg), and nanoABC (30 mg/kg ABX, 8 mg/kg BEV, and 2 mg/kg Cis).
Figure 37:
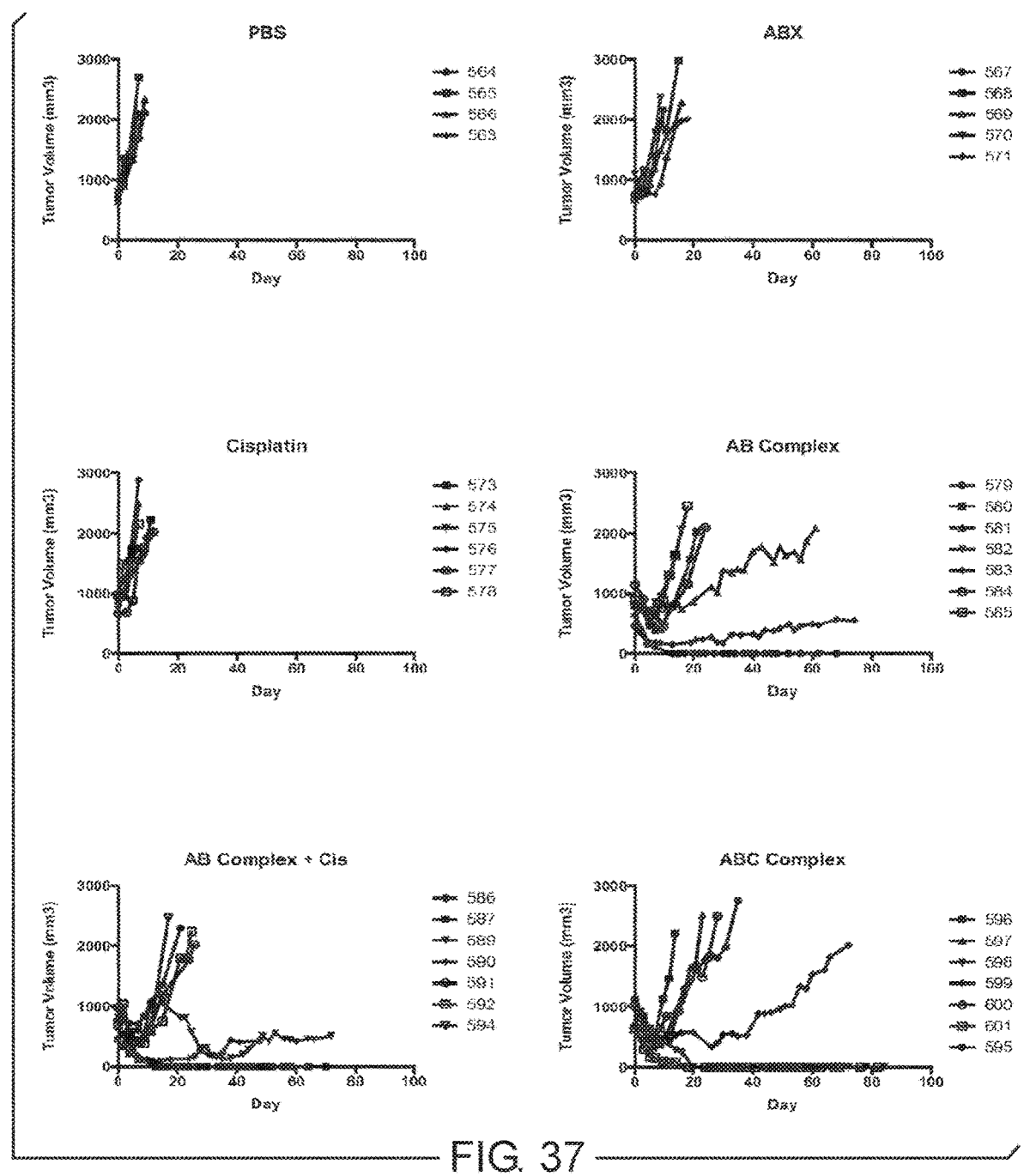
FIG. 37 is a graph plotting tumor size of A375 tumors within nude mice treated intravenously with PBS, ABRAXANE® (30 mg/kg), cisplatin (2 mg/kg), nanoAB complexes (30 mg/mL ABX and 8 mg/mL BEV), nanoAB (30 mg/mL ABX and 8 mg/mL BEV) plus cisplatin (2 mg/kg), and nanoABC (30 mg/kg ABX, 8 mg/kg BEV, and 2 mg/kg Cis).

Tumor growth kinetics among the treatment groups demonstrated delayed tumor growth in three groups: nanoAB 160 (AB Complex), nanoAB 160+Cisplatin, and nanoABC (ABC Complex) (FIGS. 35-37). There was one complete response in each of the nanoAB (1/7, 14%) and nanoAB+ cisplatin (1/7, 14%) groups, and two complete responses in the nanoABC group (2/7, 28.5%). At day 7 post-treatment, 20 of 21 (95%) mice in the three groups receiving a nanoparticle demonstrated a tumor response while 0 of 15 mice had tumor responses in the control groups. The nanoABC group had the highest median survival at 35 days. The other groups median survival was 8, 15, 9, 24, and 26 days for PBS, ABRAXANE®, cisplatin, nanoAB 160, and nanoAB 160 plus cisplatin, respectively.

Example 17—Heat Stability

Figure 38:
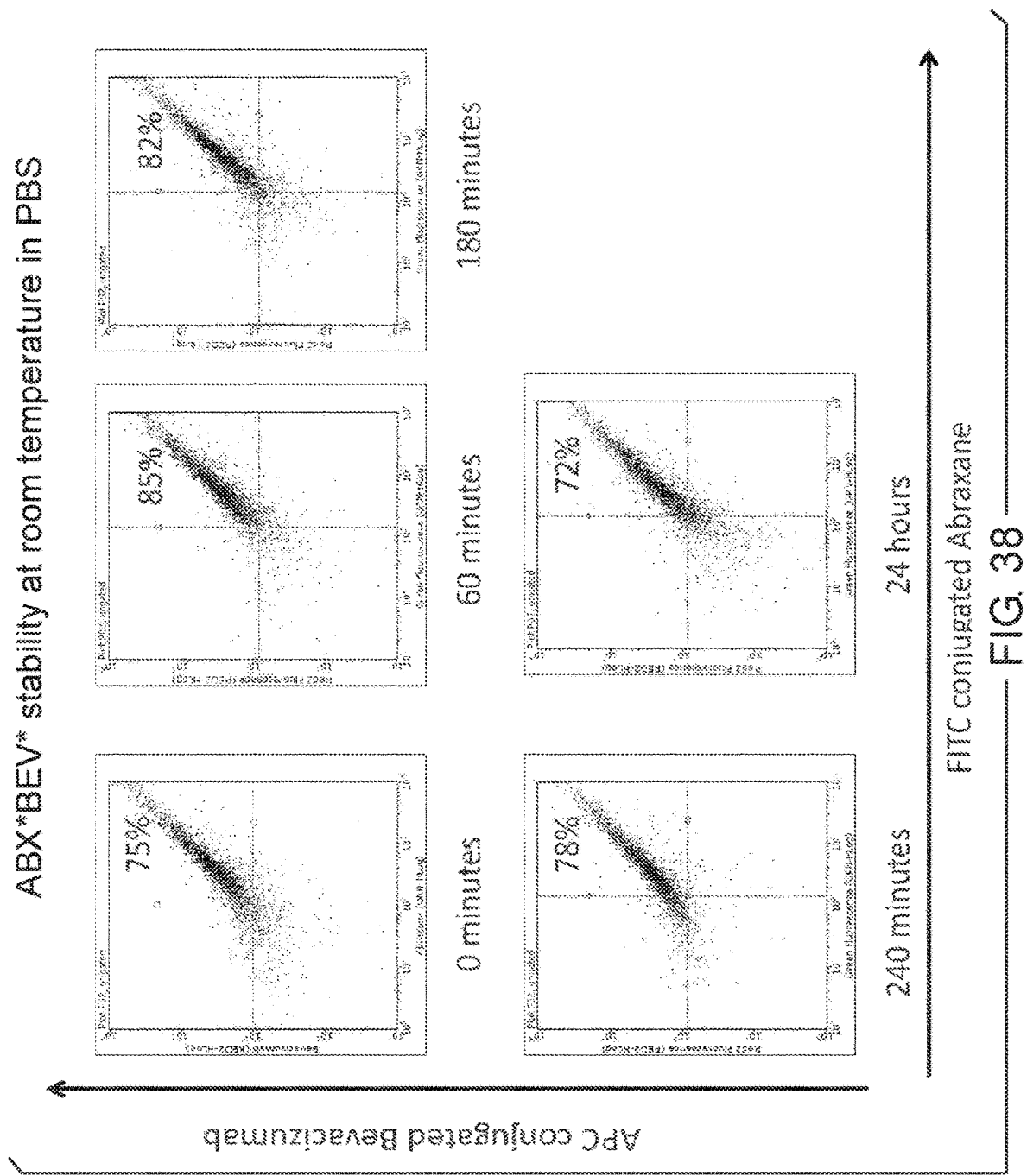
FIG. 38 is a set of flow cytometry results demonstrating the stability of nanoAB complexes incubated at room temperature for the indicated durations.

To measure nanoAB stability, ABRAXANE® and bevacizumab were directly labeled with the fluorescent markers FITC and APC, respectively, as per the manufacturer's instructions (Thermo Scientific). Unincorporated label was removed by size filtration on a sepharose column. Once labeled ABRAXANE® and bevacizumab were incubated together to form complexes as described herein. The complexes were then run on a flow cytometer (Guava, Millipore), and data was analyzed using Guava Incyte software. The stability of the complexes at room temperature in PBS was assessed (FIG. 38). The percentage of complexes double positive for ABRAXANE® and bevacizumab was 75% at time 0, and the percentage at 24 hours was 72%, demonstrating that the complexes were highly stable at room temperature.

Figure 39:
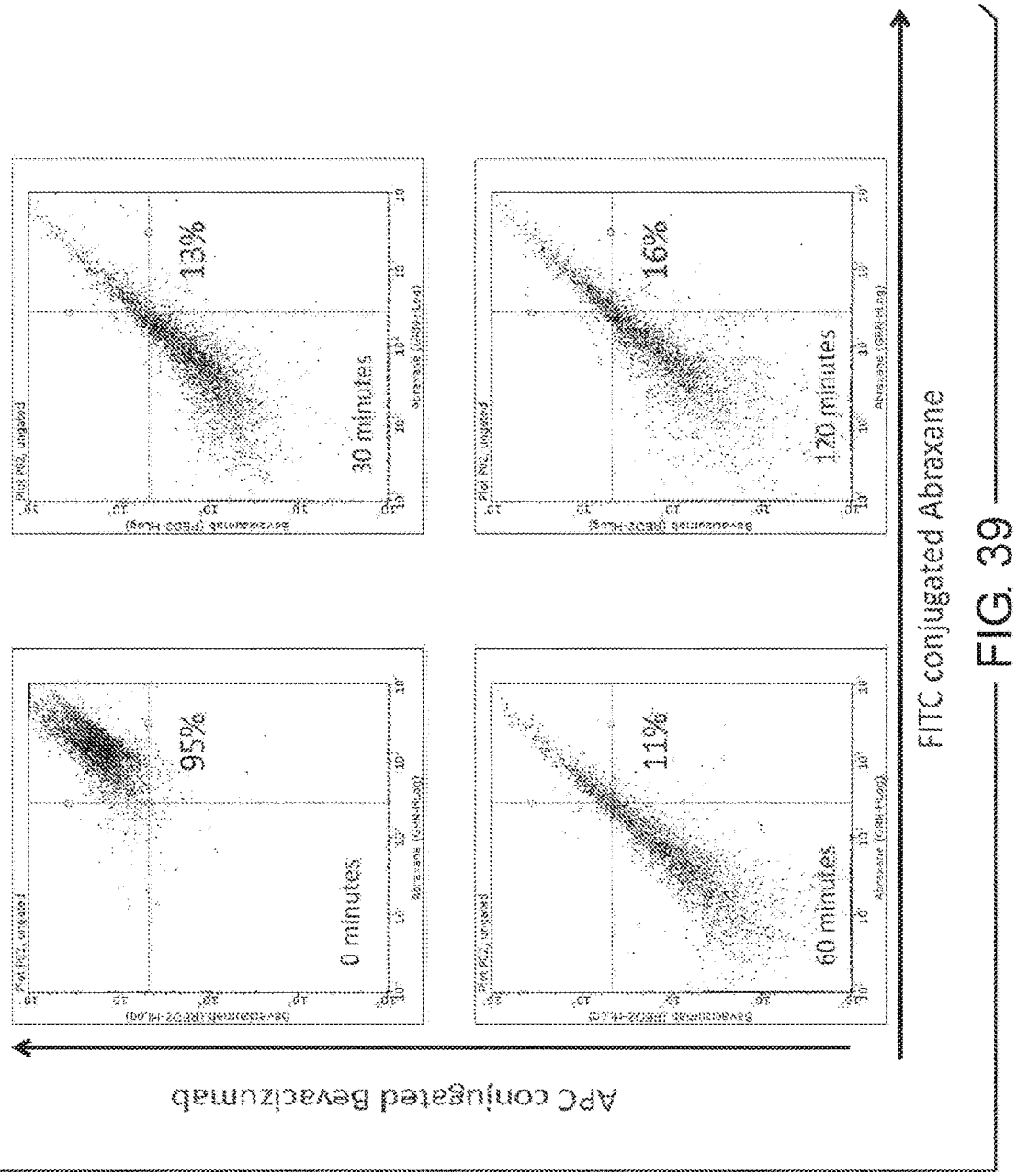
FIG. 39 is a set of flow cytometry results demonstrating the stability of nanoAB complexes incubated at 37° C. in plasma for the indicated durations.
Figure 40:
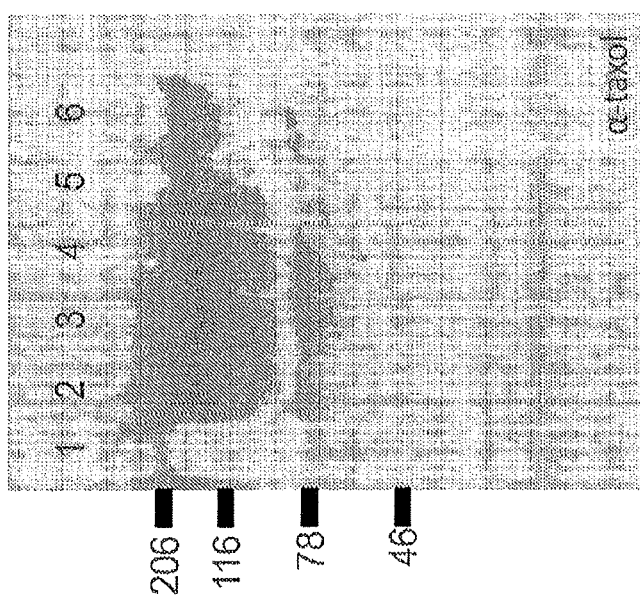
FIG. 40 contains a photograph of a Western blot analysis of nanoAB complexes incubated at 37° C. in plasma for the indicated durations using an anti-taxol antibody.

The complexes also were incubated at 37° C. in human plasma (FIG. 39). The data indicated that the complexes break down within 30 minutes in plasma at 37° C. and only about 13% remains in the large complex. The percentage shown in FIG. 39 are the percentages of complexes staying constant after 30 minutes for at least 2 hours. In a similar experiment, the complexes were incubated at 37° C. for up to 3 hours (FIG. 40). After incubation, the samples were run on a polyacrylamide gel to separate proteins by size and Western blotted with an anti-taxol antibody. These results suggest that while the big complexes break down in human plasma at 37° C., the break down product was about a 200 kD protein that contains albumin, bevacizumab, and paclitaxel.

Example 18—Binding Characteristics

The following was performed to assess protein binding due to deglycosylation of bevacizumab compared to naturally occurring IgG. In order to determine if bevacizumab binding to ABRAXANE® is due to the deglycosylation of the Fc chain of the antibody, the binding kinetics of bevacizumab were compare to naturally produced IgG isolated from human plasma. These experiments suggest that naturally occurring, fully glycosylated IgG exhibited a higher dissociation constant than bevacizumab.

Example 19—Nanoparticles and the Use of Nanoparticles to Treat Cancer

The following provides a summary of selected results from the above Examples, which in some cases may include results from additional studies.

Materials and Methods

AB160 Preparation and Size Estimation:

Ten milligrams of nab-paclitaxel power was reconstituted in 0.9% saline or bevacizumab at the following concentrations; 2, 4, 6, 8, 10, 15, and 25 mg/ml. The 1 ml mixtures were allowed to incubate for 1 hour at room temperature. The size of the particles was measured by light refraction using a Mastersizer 2000 (Malvern Instruments, Worcestershire, UK).

Immunofluorescence Imaging of AB160:

One hundred microliters of nab-paclitaxel was mixed with 100 ul of 0.5, 5, 10 and 25 mg/ml of beacizumab. The mixtures were incubated for 1 hour at room temperature and light microscopy pictures were taken at a magnification of 400×. For confocal and flow cytometry, nab-paclitaxel was directly labeled with FITC and bevacizumab was labeled with APC according to manufacturer's instructions (Thermo Scientific, Rockford, Ill.). Once labeled the nab-paclitaxel and bevacizumab were co-incubated for 30 minutes at room temperature and looked at by confocal microscopy (3LSM Confocal, Carl Zeiss MicroImaging) and flow cytometry (Guava Easycyte 8HT EMD Millipore). Flow cytometry data was analyzed using GuavaSoft software (EMD Millipore, Billerica, Mass.).

Western blotting: Nab-paclitaxel (45 mg/mL) was mixed 1:1 with bevizcumab at a concentration of 10 mg/mL or 1 mg/mL and incubated 4 hours or overnight at room temperature (25° C.). After incubation, the mixture was spun at 13,000 RPM for 10 minutes at 4° C. The supernatant was collected, mixed 1:1 with Laemmli buffer and boiled for 3 minutes prior to being loaded on at 7.5% Tris-HCl criterion gel. The gel was run at 100 volts for 2 hours before it was transferred overnight at 20 volts. 5% milk in TBST was used to block the membrane after transfer and a primary anti-mouse (Fab) IgG-HRP (1:1000) and rabbit anti-taxol (1:500) antibody was used to probe the membrane. Membranes were washed 3 times for 15 minutes. A secondary anti-rabbit IgG-HRP antibody (1:10,000) was used to label the taxol membrane. The membranes were again washed and ECL detection reagent was added to each membrane for 5 minutes. Membranes were developed on a Kodak M35A-M X-OMAT Processor and exposed for 1 second (Taxol) or 1 minute (Bevizcumab).

Bevicuzumab was diluted to a concentration of 0.25 mg/mL and hSA was diluted to a concentration of 0.05 mg/mL. The two were added 1:1 and incubated for 30 minutes at room temperature. Laemmli buffer was added 1:1 with the samples and boiled for 3 minutes without 2ME. The samples were loaded on at 7.5% Tris-HCl criterion gel and run at 100 volts for 2 hours before being transferred overnight at 20 volts. 5% milk in TBST was used to block the membrane after transfer and a primary anti-human albumin (1:10,000) antibody was used to probe the membrane. Membranes were washed 3 times for 15 minutes. A secondary anti-rabbit IgG-HRP antibody (1:10,000) was used to label the hSA membrane. The membranes were again washed and ECL detection reagent was added to the membrane for 5 minutes. The membrane was developed on a Kodak M35A-M X-OMAT Processor and exposed for 1 minute.

In Vitro AB160 Function-Proliferation Assay:

The melanoma cell line, A375, was exposed to nab-paclitaxel alone or AB160 at concentrations from 0 to 200 ug/ml paclitaxel overnight in the presence of EdU, a thymidine analog. After the overnight incubation, the A375 cells were harvested, permeabolized and intracellularly stained with a FITC conjugated anti-EdU antibody. Cell proliferation was determined by DNA synthesis as a percentage of cells, which were FITC positive on a Guava 8HT flow cytometer (Millipore Billerica, Mass.). Data analysis was performed using Gauva Incyte software (Millipore Billerica, Mass.). The proliferation index was calculated by dividing the percentage of proliferating cells in treated wells (FITC positive) by the percentage of cells proliferating in the untreated well.

In Vitro AB160 Function—Ligand Binding of AB160:

High protein binding 96 well plates were coated overnight at 4° C. with 5 mg/ml nab-paclitaxel, 1.25 mg/ml bevacizumab or AB160 containing 5 mg/ml ABRAXANE® plus 1.25 mg/ml bevacizumab. The plates were washed 3 times with PBS+0.5% Tween-20. VEGF was added to the drug coated wells at concentrations from 0 to 4000 µg/ml and incubated at room temperature for 2 hours. After 2 hours the unbound VEGF was removed and measured via standard VEGF ELISA (R and D Systems Minneapolis, Minn.). The percent of drug bound VEGF was calculated by (concentration VEGF after drug exposure/total concentration of VEGF measured from standard curve)*100.

In vitro AB160 function—small animal model: Female athymic nude mice were injected with $1\times10^6$ A375 melanoma cells in the flank. Tumors were allowed to grow, and treatments were administered when tumors were between 600 and 1000 mm$^3$. Mice were treated with (a) 100 µL PBS, (b) bevacizumab (8 mg/kg), (c) nab-paclitaxel (30 mg/kg), (d) bevacizumb (day 0 8 mg/kg) followed by nab-paclitaxel (day 1, 30 mg/kg), (e) AB160 which was produced as follows: 10 mg nab-paclitaxel was reconstituted in 3.6 mg of bevacizumab in 500 µL 0.9% saline and incubated for 1 hour at room temperature. After incubation, AB160 was brought to 1 mL with 0.9% saline. AB160 was further diluted, and 100 µL was administered to mice for a final 8 mg/kg bevacizumab and 30 mg/kg nab-paclitaxel dose. Tumor size was monitored 2-3 times per week. Mice were sacrificed when tumors reached 2000-2500 mm$^3$. Percent change from baseline was calculated by [(tumor size on day 7−tumor size on day of treatment)/tumor size on day of treatment]*100.

Results

Under specific in vitro mixing conditions, the mixing of varying concentrations of clinical grade bevacizumab and nab-paclitaxel creates a range of different size macromolecular complexes as determined by direct visualization with phase contrast light microscopy (FIG. 9) and light scatter size distribution analysis (FIG. 25). Immunofluorescent labeling of bevacizumab and/or nab-paclitaxel demonstrated double-labeling of the macromolecular complexes using immunofluorescence microscopy (FIG. 41A) and flow cytometry (FIG. 41B). These data suggest that in vitro mixing of bevacizumab and nab-paclitaxel in varying relative concentrations results in the creation of macromolecular complexes of different sizes containing both drugs.

Figure 42A:
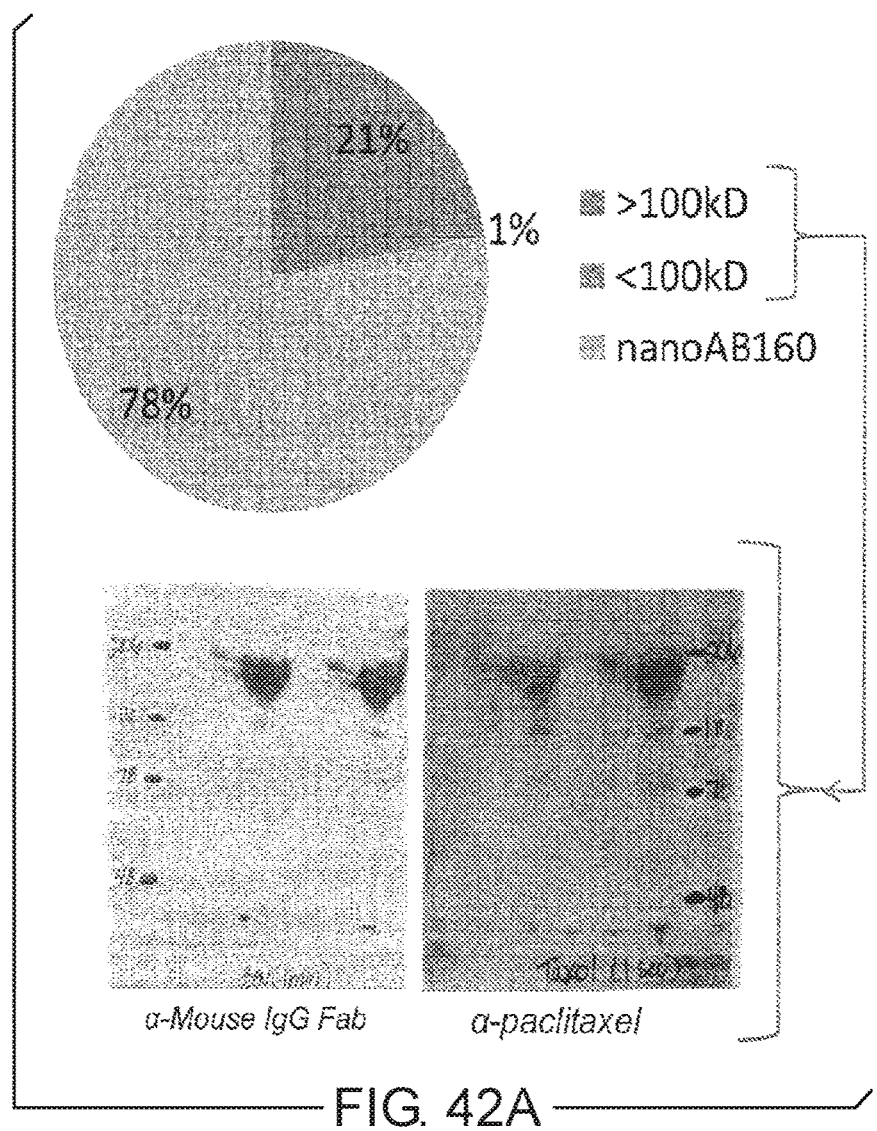
FIG. 42A contains a pie chart (top) demonstrating that 78% of the paclitaxel content can be removed with centrifugation under conditions used to remove particulate ABX. In the remaining supernatant, the majority (21%) of the paclitaxel is of a molecular weight >100 kD, suggesting binding to BEV (140 kD), with a minor fraction (1%) of MW less than 100 kD. Western blot analysis (bottom) demonstrated that the majority of the non-particulate paclitaxel is of a molecular weight in the 200 kD range, suggesting that free paclitaxel/albumin dimers (60 kD) may be binding to excess BEV (140 kD). Gel lanes: (1) ABX supernatant 45 mg/mL after 4 h incubation at room temperature; (2) AB160 supernatant 1 mg/mL, at 4 hours; (3) AB160 supernatant 10 mg/mL, at 4 hours; (4) ABX supernatant overnight (45 mg/mL); (5) AB160 supernatant 1 mg/mL, overnight; (6) AB160 supernatant, 10 mg/mL, overnight.
Figure 42B:
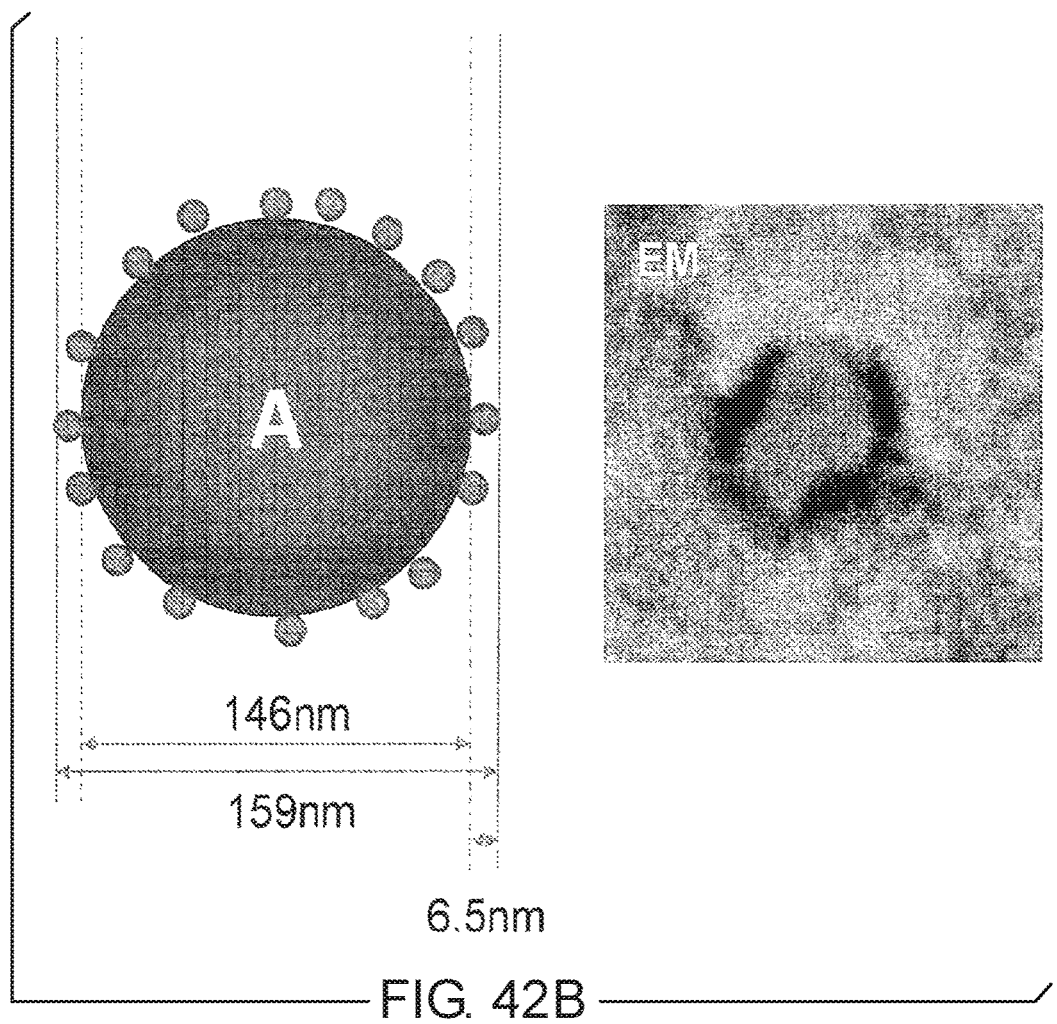
FIG. 42B contains a cartoon (top) and an electron microscopy (EM) image (bottom) obtained by AB160 staining with anti-human-Ig gold conjugate, demonstrating that the median size of the AB160 complexes is in the range of 157 to 159 nm. This suggests a monolayer coating of the ABX nanoparticle by BEV.
Figure 42C:
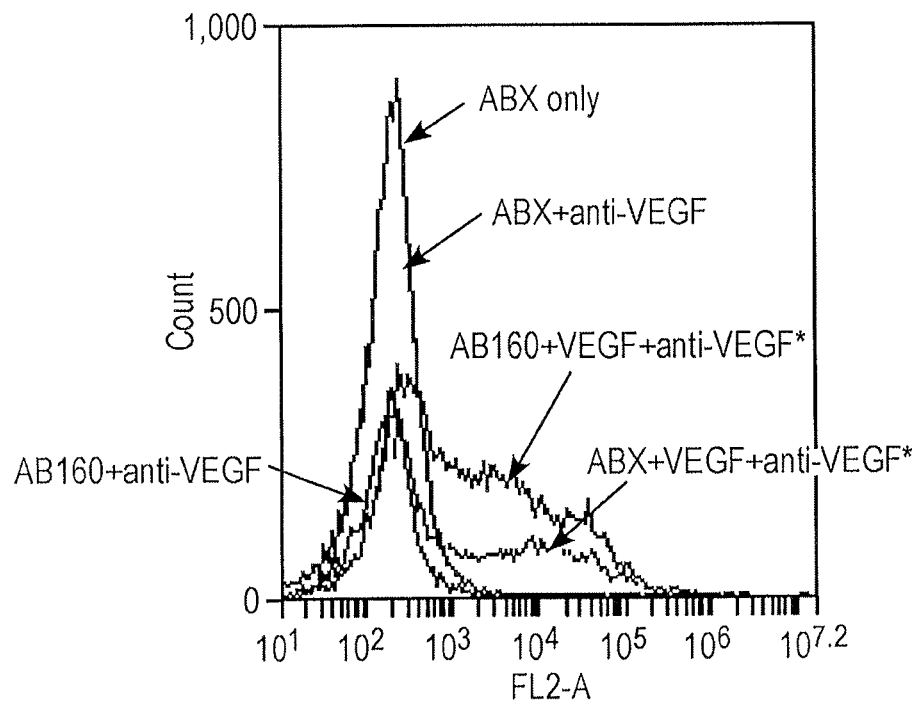
FIG. 42C is a graph plotting cell counts from a flow-cytometry analysis of ABX and AB160 incubated with or without VEGF and an anti-VEGF fluorescinated monoclonal antibody, suggesting maximal VEGF binding to the AB160 complex over that of ABX alone, and indicating that BEV binds to the ABX albumin mantle via its Fc segment, preserving binding affinity for VEGF.
Figure 42D:
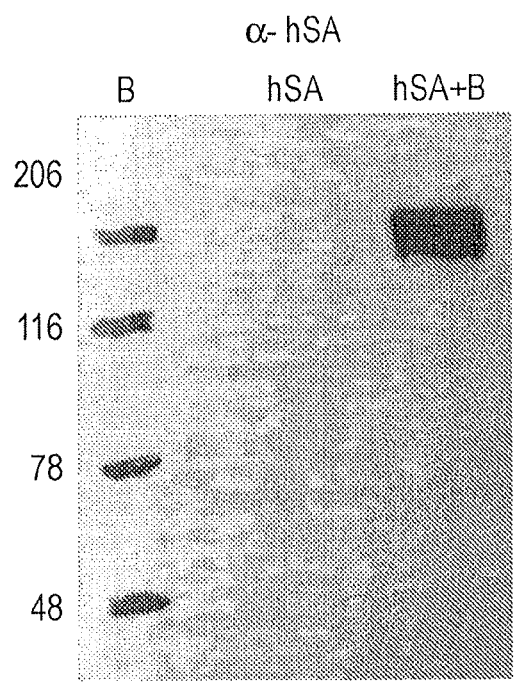
FIG. 42D is a picture of a non-denatured western blot, demonstrating the association of commercial human serum albumin (hSA, MW=60 kD) with bevacizumab (B, MW=140 kD).
Figure 43A:
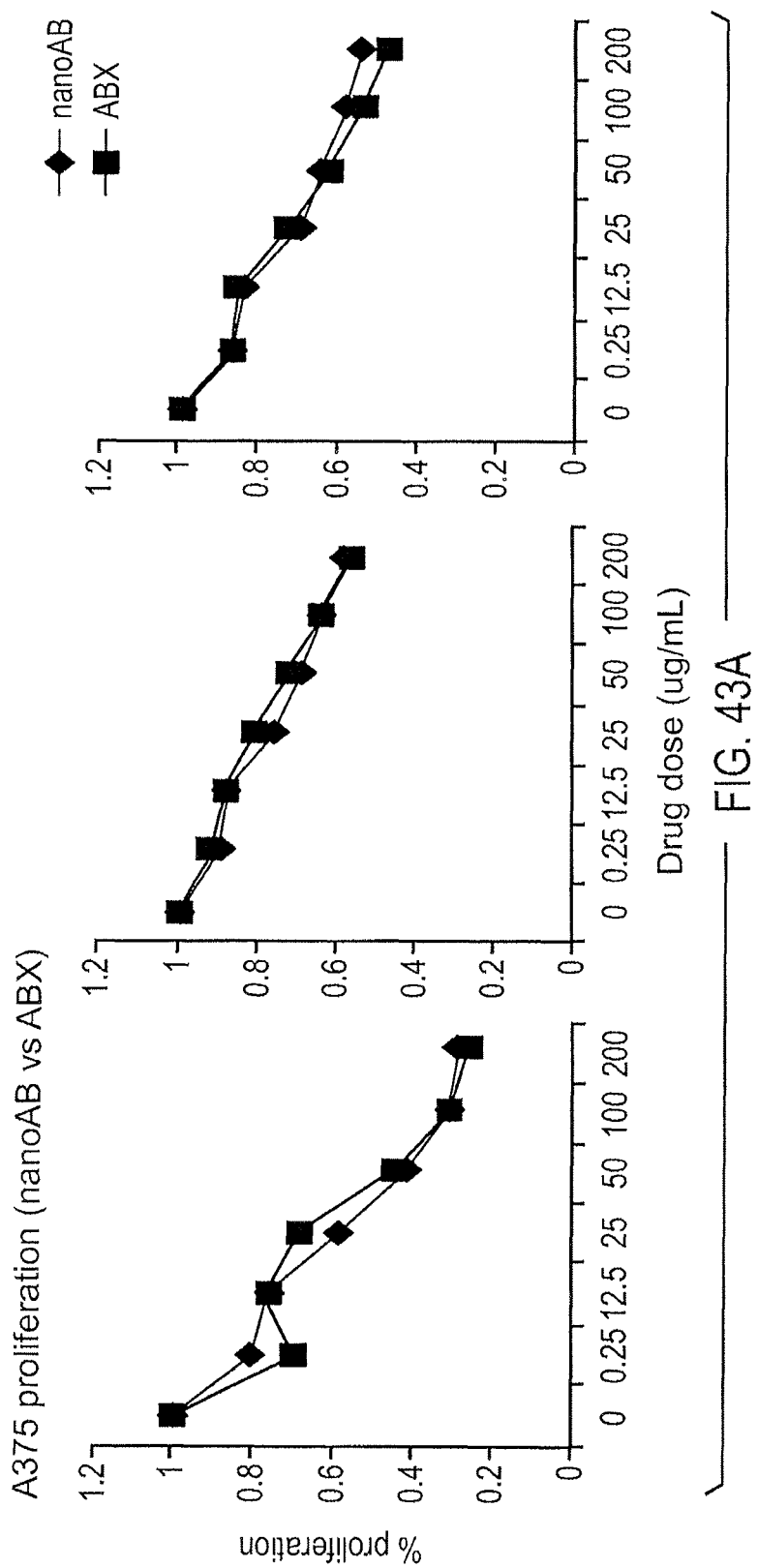
FIGS. 43A and 43B contain a series of graphs plotting proliferation and VEGF binding for AB160 relative to either ABX or BEV, respectively. Under in vitro conditions, AB160 was equally as effective in inhibiting human melanoma proliferation (A375) as was seen with ABX alone (FIG. 43A). In addition, AB160 was equally as efficient in binding soluble human VEGF as was free BEV (FIG. 43B).
Figure 43B:
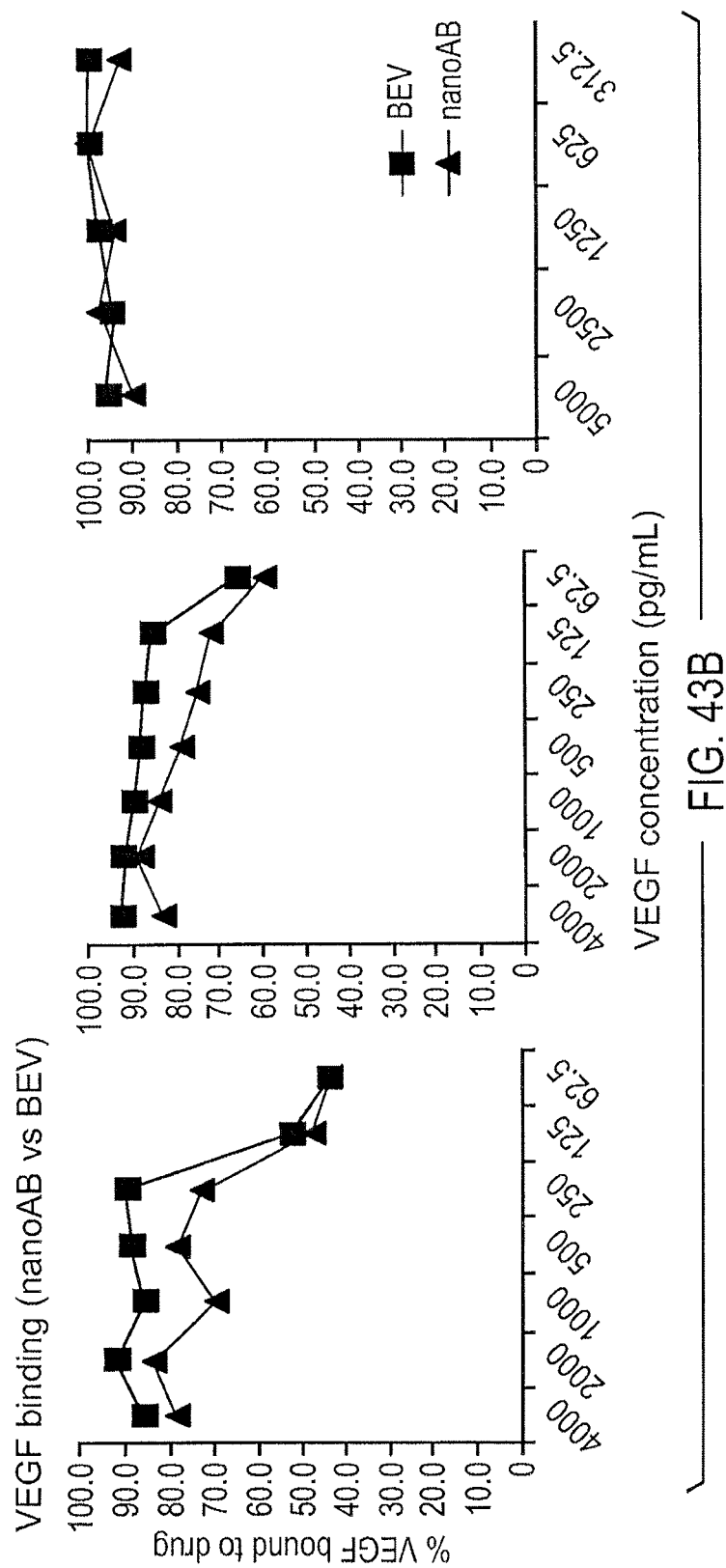
Figures 44C, 44D:
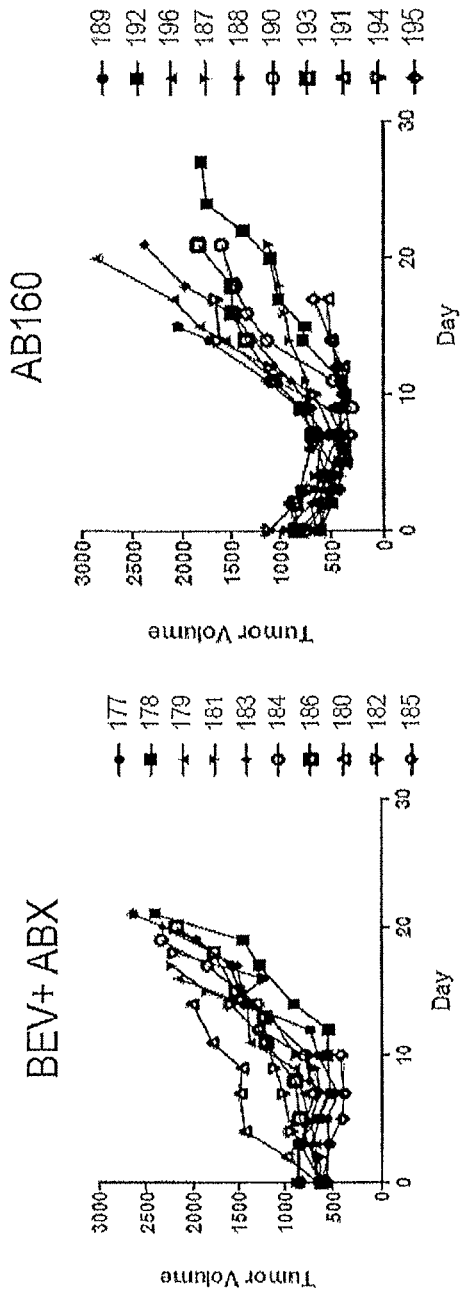
Figure 44F:
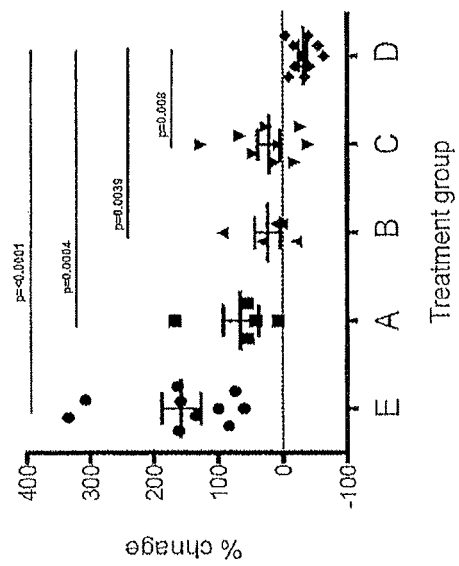
FIG. 44F is a graph plotting the % change in tumor size from baseline, on day 7 following treatment on day 0, for the groups of animals treated as in FIGS. 44A-44E.
Figure 44E:
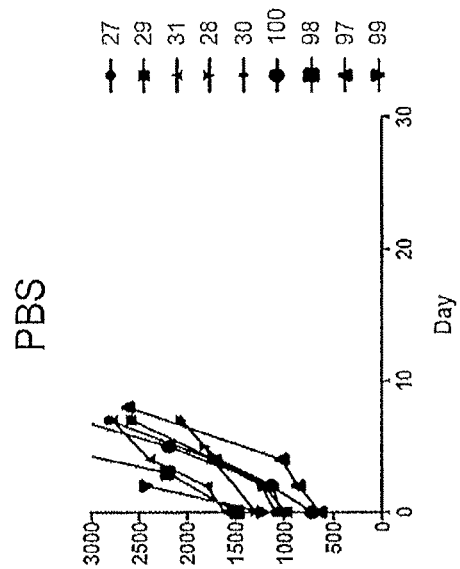
Figure 44G:
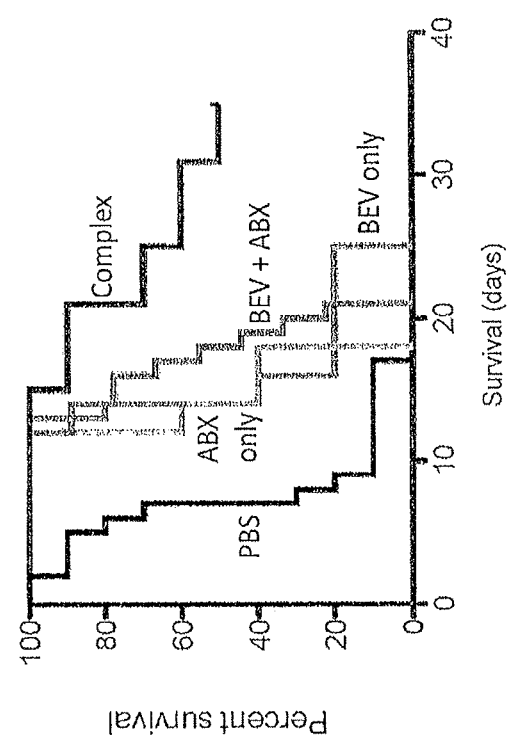
FIG. 44G is a Kaplan-Meier plot for the time from drug delivery until a tumor size of 2500 mm³ was reached (pre euthanasia), as in FIGS. 44A-44E.

With the aim of developing an agent (macromolecular complex) most amenable to rapid clinical translation (minimal alteration of existing FDA approved agents), efforts were concentrated on further characterizing the bevacizumab/nab-paclitaxel complex demonstrating a median particle size of 160 nm (AB160). Under the conditions used, approximately 80% of the complex formed the 160 nm particle, and roughly 20% consisted of 200 kD molecules containing paclitaxel and bevacizumab (FIG. 42A). The 160 nm diameter of the AB160 complex approximated a monolayer coating of nab-paclitaxel by bevacizumab (FIG. 42B; cartoon and EM image of AB160 stained with anti-human-Ig-gold conjugate). Bevacizumab appeared to bind to nab-paclitaxel at the level of the albumin mantle of the nanoparticle via its Fc domain retaining VEGF binding capacity (FIG. 42C). Flow-cytometric analysis of the AB160 particle (versus nab-paclitaxel) demonstrated that maximal fluorescence of the nanoparticles was achieved when a fluorescently labeled anti-VEGF antibody was incubated with the AB160 complex in the presence of VEGF; significantly less anti-VEGF staining was observed for nab-paclitaxel incubated with VEGF alone. This suggested a somewhat unexpected affinity of bevacizumab to albumin that can easily be demonstrated by co-incubating human serum albumin (hSA) and bevacizumab and blotting for albumin (FIG. 42D). Under non-denaturing conditions, the albumin band, in the bevacizumab/albumin mixture, migrated at a MW of approximately 200 Kd, as would be predicted for an albumin/bevacizumab complex (60 kD+140 kD, respectively). Affinity analyses of the bevacizumab/nab-paclitaxel and the bevacizumab/hSA complex dissociation constants (Kd=$5.8\times10^{-7}$, and Kd=$6.2\times10^{-6}$, respectively) suggested that the bevacizumab/albumin interaction is hydrophobic. Additionally, the AB160 complex retained both the antiproliferative properties of nab-paclitaxel as well as the VEGF binding properties of bevacizumab (FIGS. 43A and 43B).

Figure 45A:
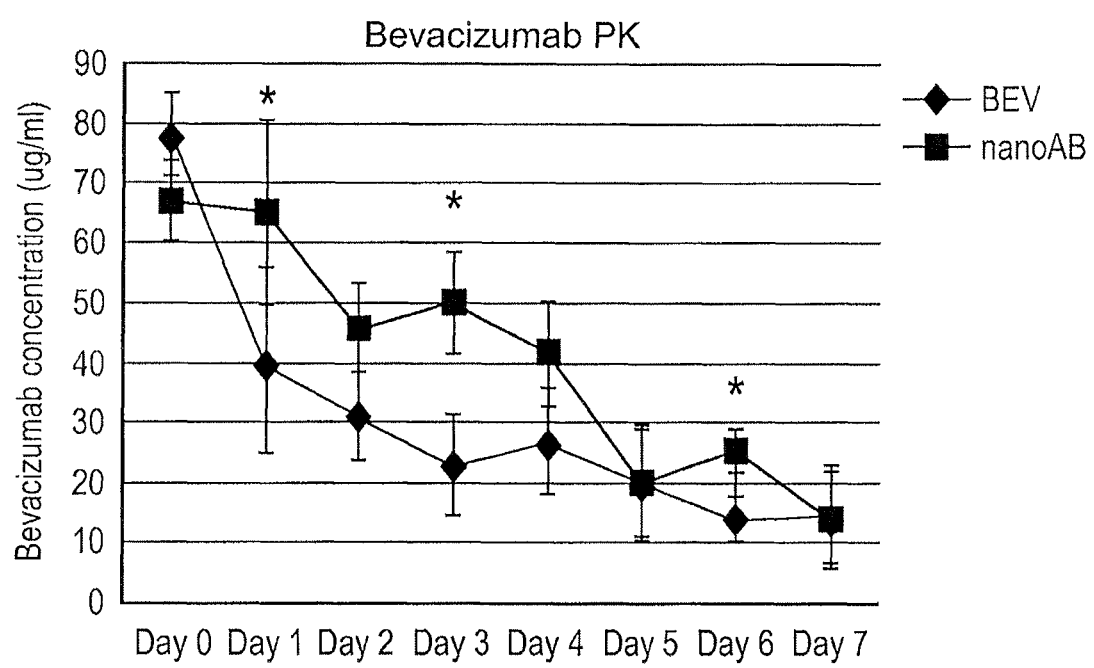
FIGS. 45A-C contain graphs plotting data related to the in vivo biologic activity of AB160.
Figure 45B:
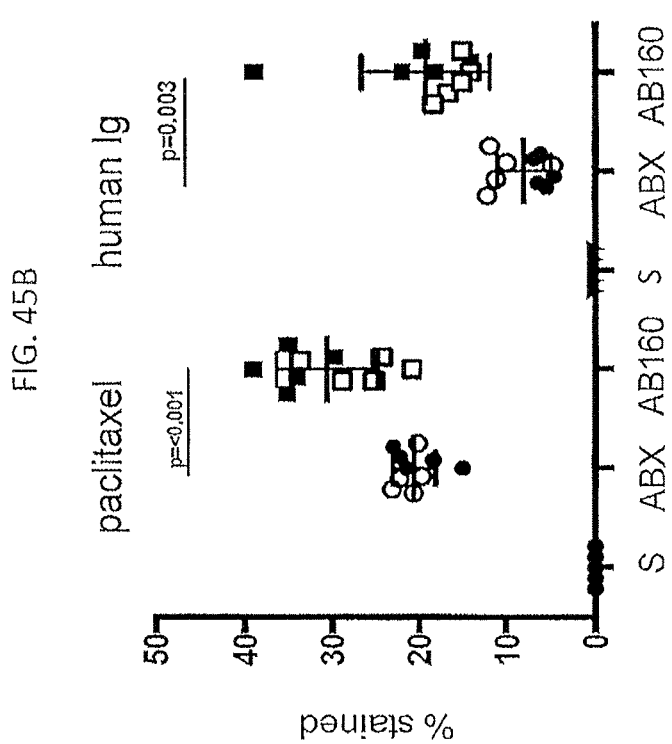
Figure 45C:
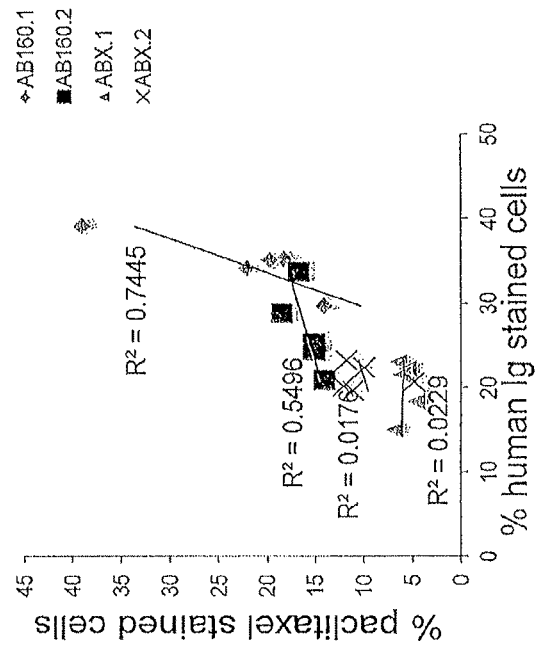

Nude mice implanted with the human A375 melanoma developed tumors with sizes in the range of 1000 mm$^3$ at the time of single IV injection with AB160, bevacizumab, nab-paclitaxel, or sequential infusion of bevacizumab followed by next-day nab-paclitaxel (FIG. 44). Tumor growth kinetics as well as percent change of tumor size following the single injection of drug demonstrated that the most favorable outcomes were observed in the AB160 cohort. Pharmacokinetic analysis of peripheral blood and tumors following a single injection of either AB160, nab-paclitaxel or bevacizumab, demonstrated: (a) prolongation of the plasma elimination of bevacizumab in AB160 versus that of bevacizumab alone (FIG. 45A); and (b) significantly increased percentage of tumor cells demonstrating intracellular paclitaxel (by IHC) in the AB160 cohort relative to that of nab-paclitaxel alone or saline treated controls (FIG. 45B). Of note, there appeared to be a correlation between tissue sections that stained positive with paclitaxel and those staining positive for human immune globulin (detecting bevacizumab, FIG. 45C, R values of 0.7445 and 0.5496). No such correlations were detected in nab-paclitaxel (ABX) alone treated mice (R values of 0.0176 and 0.0229).

Collectively, these data suggest that the AB160 formulation of nab-paclitaxel allows for prolonged circulation and increased delivery of paclitaxel at the VEGF expressing tumor site, likely responsible for the observed "clinical" benefit. In effect, the AB160 macromolecule seems to increase the efficiency of paclitaxel delivery into the VEGF expressing malignancy. Ongoing data further support this observation by describing the in vivo AB160 dissociation subunits as hetero-trimers consisting of bevacizumab-albumin-paclitaxel. This is further supported by the observed improved clinical benefit of larger AB complexes in similar in vivo A375 mouse xenograft experiments.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody-albumin nanoparticle complex, the nanoparticle complex comprising albumin, a rituximab antibody, and paclitaxel, wherein the nanoparticle complex has been pre-formed in vitro by mixing an aqueous albumin-paclitaxel nanoparticle with the antibody under conditions to form the nanoparticle complex, such that the nanoparticle complex has CD20 binding specificity, said complex having a diameter of between 0.1 µm and 1 µm.

2. The antibody-albumin nanoparticle complex of claim 1, further comprising an alkylating agent.

3. The antibody-albumin nanoparticle complex of claim 2, wherein said alkylating agent is a platinum compound.

4. The antibody-albumin nanoparticle complex of claim 3, wherein said platinum compound is carboplatin.

5. The antibody-albumin nanoparticle complex of claim 1, said complex having a diameter of between 0.1 µm and 0.9 µm.

6. The antibody-albumin nanoparticle complex of claim 1, said complex having a diameter of between 0.1 µm and 0.3 µm.

7. The antibody-albumin nanoparticle complex of claim 1, wherein the ratio of albumin-paclitaxel nanoparticle to antibody is between 5:1 and 1:2.5.

8. A pharmaceutical composition comprising a pharmaceutically acceptable carrier antibody-albumin nanoparticle complexes, wherein said antibody-albumin nanoparticle complexes comprise albumin, a rituximab antibody, and paclitaxel, wherein the nanoparticle complexes have been pre-formed in vitro by mixing aqueous albumin-paclitaxel nanoparticles with the antibody under conditions to form the nanoparticle complex, such that the nanoparticle complexes have binding specificity, said complexes having an average diameter of between 0.1 µm and 1 µm.

9. The pharmaceutical composition of claim 8, wherein said composition or said antibody-albumin nanoparticle complexes comprise an alkylating agent.

10. The pharmaceutical composition of claim 9, wherein said alkylating agent is a platinum compound.

11. The pharmaceutical composition of claim 10, wherein said platinum compound is carboplatin.

12. The pharmaceutical composition of claim 8, wherein the average diameter of said complexes is between 0.1 µm and 0.9 µm.

13. The pharmaceutical composition of claim 8, wherein the average diameter of said complexes is between 0.1 µm and 0.3 µm.

14. The pharmaceutical composition of claim 8, wherein the ratio of albumin-paclitaxcel nanoparticle to antibody is between 5:1 and 1:2.5.

15. A method of making an antibody-albumin nanoparticle complex, the method comprising mixing in vitro an aqueous albumin-paclitaxel nanoparticle with a rituximab antibody under conditions to form the nanoparticle complex, wherein said complexes have an average diameter of between 0.1 µm and 1 µm.

* * * * *

UNITED STATES PATENT AND TRADEMARK OFFICE
CERTIFICATE OF CORRECTION

Page 1 of 2

PATENT NO. : 10,507,243 B2
APPLICATION NO. : 15/414526
DATED : December 17, 2019
INVENTOR(S) : Markovic et al.

It is certified that error appears in the above-identified patent and that said Letters Patent is hereby corrected as shown below:

On the Title Page

Item (54) Title: Please correct "PACLTAXEL" to read -- PACLITAXEL --

Item (56) References Cited, OTHER PUBLICATIONS, Page 3, Column 2, Line 21, Celts cite: Please correct "Celts" to read -- Celis --

Item (56) References Cited, OTHER PUBLICATIONS, Page 7, Column 1, Line 11: Please correct "U.S. Appl. No. 14/432,979, office action dated Feb. 15, 2016" to read -- U.S. Appl. No. 14/432,979, office action dated Dec. 15, 2016 --

Item (56) References Cited, OTHER PUBLICATIONS, Page 7, Column 1, Line 37: Please correct "U.S. Appl. No. 16/225,428, office action dated Aug. 14, 2018" to read -- U.S. Appl. No. 15/225,428, office action dated Aug. 14, 2018 --

Item (56) References Cited, OTHER PUBLICATIONS, Page 7, Column 1, Line 47: Please correct "U.S. Appl. No. 15/266,024, office action dated Jan. 6, 2017" to read -- U.S. Appl. No. 15/286,024, office action dated Jan. 6, 2017 --

Item (56) References Cited, OTHER PUBLICATIONS, Page 7, Column 1, Line 61: Please correct "U.S. Appl. No. 15/414,633; office action dated Nov. 19, 2018" to read -- U.S. Appl. No. 15/414,533; office action dated Nov. 19, 2018 --

Item (56) References Cited, OTHER PUBLICATIONS, Page 7, Column 1, Line 62: Please correct "U.S. Appl. No. 15/414,530; office action dated Oct. 11, 2018" to read -- U.S. Appl. No. 15/414,536; office action dated Oct. 11, 2018 --

Item (56) References Cited, OTHER PUBLICATIONS, Page 7, Column 1, Line 64: Please correct "U.S. Appl. No. 15/452,569, office action dated Nov. 16, 2017" to read -- U.S. Appl. No. 15/452,669, office action dated Nov. 16, 2017 --

Signed and Sealed this
Twelfth Day of May, 2020

Andrei Iancu
*Director of the United States Patent and Trademark Office*

CERTIFICATE OF CORRECTION (continued)
U.S. Pat. No. 10,507,243 B2

Item (56) References Cited, OTHER PUBLICATIONS, Page 7, Column 2, Line 26: Please correct "European Application No. 16809075.3" to read -- European Application No. 15809075.3 --

Item (56) References Cited, OTHER PUBLICATIONS, Page 7, Column 2, Line 51, Inman cite: Please correct "Afezolizumab" to read -- Atezolizumab --

Item (56) References Cited, OTHER PUBLICATIONS, Page 7, Column 2, Line 64: Please correct "PCT/US2016/026267, dated Apr. 10, 2016." to read -- PCT/US2016/026267, dated Apr. 10, 2018. --

Item (56) References Cited, OTHER PUBLICATIONS, Page 8, Column 2, Line 1, Neval et al. cite: Please correct "Neval" to read -- Nevala --

Item (56) References Cited, OTHER PUBLICATIONS, Page 8, Column 2, Line 54, Volk-Draper et al. cite: Please correct "Sesaloid" to read -- Basaloid --

In the Specification

Column 1, Line 2: Please correct "PACLTAXEL" to read -- PACLITAXEL --

Column 10, Line 31: Please correct "1, stage 11," to read -- I, stage II --

Column 21, Line 20: Please correct "(25 ALL)" to read -- (25 μL) --

Column 25, Line 38: Please correct "ANC≥1500/mm" to read -- ANC≥1500/mm$^3$ --

Column 39, Line 51: Please correct "4000 μg/ml" to read -- 4000 pg/ml --